United States Patent
Du et al.

(10) Patent No.: US 9,676,808 B2
(45) Date of Patent: *Jun. 13, 2017

(54) 2',4'-SUBSTITUTED NUCLEOSIDES AS ANTIVIRAL AGENTS

(71) Applicant: Gilead Pharmasset LLC, Foster City, CA (US)

(72) Inventors: Jinfa Du, Redwood City, CA (US); Michael Joseph Sofia, Doylestown, PA (US)

(73) Assignee: GILEAD PHARMASSET LLC, Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/007,810

(22) Filed: Jan. 27, 2016

(65) Prior Publication Data

US 2016/0280735 A1    Sep. 29, 2016

Related U.S. Application Data

(63) Continuation of application No. 14/265,840, filed on Apr. 30, 2014, now Pat. No. 9,296,777, which is a continuation of application No. 13/324,068, filed on Dec. 13, 2011, now Pat. No. 8,765,710, which is a continuation of application No. 12/271,388, filed on Nov. 14, 2008, now abandoned.

(60) Provisional application No. 60/989,296, filed on Nov. 20, 2007.

(51) Int. Cl.
| | |
|---|---|
| C07H 19/06 | (2006.01) |
| C07H 19/16 | (2006.01) |
| C07H 19/073 | (2006.01) |
| C07H 19/173 | (2006.01) |
| A61K 31/7064 | (2006.01) |
| A61K 31/7068 | (2006.01) |
| A61K 31/7072 | (2006.01) |
| A61K 31/7076 | (2006.01) |
| C07H 19/14 | (2006.01) |

(52) U.S. Cl.
CPC ......... *C07H 19/06* (2013.01); *A61K 31/7064* (2013.01); *A61K 31/7068* (2013.01); *A61K 31/7072* (2013.01); *A61K 31/7076* (2013.01); *C07H 19/073* (2013.01); *C07H 19/14* (2013.01); *C07H 19/16* (2013.01); *C07H 19/173* (2013.01)

(58) Field of Classification Search
None
See application file for complete search history.

(56) References Cited

U.S. PATENT DOCUMENTS

| | | |
|---|---|---|
| 5,856,085 A | 1/1999 | Wang et al. |
| 5,977,325 A | 11/1999 | McCarthy et al. |
| 6,403,568 B1 | 6/2002 | Ohrui et al. |
| 7,094,768 B2 | 8/2006 | Roberts et al. |
| 7,495,006 B2 | 2/2009 | Liotta et al. |
| 7,666,856 B2 | 2/2010 | Johansson et al. |
| 8,318,776 B2 | 11/2012 | Mizuno |
| 8,765,710 B2 | 7/2014 | Sofia et al. |
| 2002/0147160 A1 | 10/2002 | Bhat et al. |
| 2003/0236216 A1 | 12/2003 | Devos et al. |
| 2004/0067901 A1 | 4/2004 | Bhat et al. |
| 2004/0072788 A1 | 4/2004 | Bhat et al. |
| 2005/0272676 A1 | 12/2005 | Bhat et al. |
| 2006/0205686 A1 | 9/2006 | Bhat et al. |
| 2006/0223835 A1 | 10/2006 | Liotta et al. |
| 2006/0264390 A1 | 11/2006 | Eldrup et al. |
| 2007/0004669 A1 | 1/2007 | Carroll et al. |
| 2007/0135363 A1 | 6/2007 | Cook et al. |
| 2007/0275912 A1 | 11/2007 | Bhat et al. |
| 2009/0131415 A1 | 5/2009 | Letavic et al. |
| 2009/0318380 A1 | 12/2009 | Sofia et al. |
| 2010/0234584 A1 | 9/2010 | Chang |
| 2012/0232029 A1 | 9/2012 | Sofia et al. |

FOREIGN PATENT DOCUMENTS

| | | |
|---|---|---|
| WO | WO-97/12033 A1 | 4/1997 |
| WO | WO-01/79246 A2 | 10/2001 |
| WO | WO-02/057287 A2 | 7/2002 |
| WO | WO-02/057425 A2 | 7/2002 |
| WO | WO-02/100415 A2 | 12/2002 |
| WO | WO-2004/000858 A2 | 12/2003 |
| WO | WO-2005/021568 A2 | 3/2005 |
| WO | WO-2006/12078 A2 | 2/2006 |
| WO | WO-2007/038507 A2 | 4/2007 |
| WO | WO-2008/043704 A1 | 4/2008 |
| WO | WO-2008/121634 A2 | 10/2008 |
| WO | WO-2009/009951 A1 | 1/2009 |
| WO | WO-2009/067409 A1 | 5/2009 |

OTHER PUBLICATIONS

Awano, H., et al., (1996), "Synthesis and antiviral activity of 5-substituted (2'S)-2'-deoxy-2'-C-methylcytidines and -uridines", Arch Pharm., 329:66-72.
Bartenschlager, R., (1994), "Kinetic and structural analyses of hepatitis C virus polyprotein processing", J Virol., 68:5045-55.
Bartenschlager, R., et al., (1993), "Nonstructural protein 3 of the hepatitis C virus encodes a serine-type proteinase required for cleavage at the NS3/4 and NS4/5 junctions", J Virol., 67:3835-44.
Bazan, et al., (1989), "Detection of a trypsin-like serine protease domain in flaviviruses and pestiviruses", Virology, 17:637-9.
Beaulieu, P., et al., (2004), "Inhibitors of the HCV NS5B polymerase: new hope for the treatment of hepatitis C infections", Curr Opin Investig Drugs., 5:838-50.
Behrens, S., et al., (1996), "Identification and properties of the RNA-dependent RNA polymerase of hepatitis C virus", EMBO J., 15:12-22.
Byrn, S., et al., (1999), "Hydrates and Solvates", Solid-State Chemistry of Drugs, 2nd Edition, 233-47.
Calisher, C., et al., (1989), "Antigenic relationships between flaviviruses as determined by cross-neutralization tests with polyclonal antisera", J Gen Virol., 70:37-43.

(Continued)

Primary Examiner — Traviss C McIntosh, III

(57) ABSTRACT

Embodiments of the invention are to compounds, methods, and compositions for use in the treatment of viral infections. More specifically embodiments of the invention are 2',4'-substituted nucleoside compounds useful for the treatment of viral infections, such as HIV, HCV, and HBV infections.

1 Claim, No Drawings

(56) References Cited

OTHER PUBLICATIONS

Carroll, S., (2006), "Nucleoside analog inhibitors of hepatitis C virus replication", *Infect Disord Drug Targets.*, 6:17-29.
Eckart, M., et al., (1993), "The hepatitis C virus encodes a serine protease involved in processing of the putative nonstructural proteins from the viral polyprotein precursor", *Biochem Biophys Res Commun.*, 192:399-406.
European Communication—Intent to Grant, dated Jun. 18, 2014, issued in corresponding EP App. No. 12192594.5, 5pp.
European Communication dated Jul. 30, 2013, issued in corresponding EP App. No. 08852934.2, 6pp.
European Communication, dated Nov. 15, 2010, in European App. No. EP 08852934.2,.
European Communication, Extended European Search Report dated Jul. 31, 2013, issued in corresponding EP App. No. 12192594.5, 8pp.
Failla, C., et al., (1994), "Both NS3 and NS4A are required for proteolytic processing of hepatitis C virus nonstructural proteins", *J Virol.*, 68:3753-60.
Final Office Action for U.S. Appl. No. 13/324,068, dated May 21, 2013.
Gorbalenya, A., et al., (1989), "N-terminal domains of putative helicases of flavi- and pestiviruses may be serine proteases", *Nucleic Acids Res.*, 17:3889-97.
Gorbalenya, A., et al., (1988), "A conserved NTP-motif in putative helicases", *Nature*, 333:22.
Grakoui, A., et al., (1993), "A second hepatitis C virus-encoded proteinase", *Proc Natl Acad Sci.*, 90:10583-7.
Grakoui, A., et al., (1993), "Characterization of the hepatitis C virus-encoded serine proteinase: determination of proteinase-dependent polyprotein cleavage sites", *J Virol.*, 67:2832-43.
Griffith, R., et al., (2004), "HCV Anit-viral Agents", *Annual Reports in Medicinal Chemistry*, 39:223-37.
Halstead, S., (1984), "Selective primary health care: strategies for control of disease in the developing world. XI. Dengue", *Rev Infect Dis.*, 6:251-64.
Halstead, S., (1988), "Pathogenesis of dengue: challenges to molecular biology"*Science*, 239:476-81.
Herdewijn, P., (1997), "Structural requirements for antiviral activity in nucleosides", *Drug Discovery Today*, 2:235-42.
Hijikata, M., et al., (1993), "Two distinct proteinase activities required for the processing of a putative nonstructural precursor protein of hepatitis C virus", *J Virol.*, 67:4665-75.
International Preliminary Examination Report, issued in PCT/US2008/083787, mailed May 25, 2010.
International Search Report, issued in PCT/US2008/083787, mailed Mar. 26, 2009.
Ishii, K., et al., (1999), "Expression of hepatitis C virus NS5B protein: characterization of its RNA polymerase activity and RNA binding", *Hepatology*, 29:1227-35.
Jin, Y., et al., (1995), "Synthesis and antiviral activity of fluoro sugar nucleosides 1: Studies on 4'-azido-2'-deoxy-2'-fluoro-arabinofuranosyl nucleosides", *Arch Pharm Res.*, 18:364-5.
Jin, L., et al., (1995), "Expression, isolation, and characterization of the hepatitis C virus ATPase/RNA helicase", *Arch Biochem Biophys.*, 323:47-53.
Kim, D., et al., (1995), "C-terminal domain of the hepatitis C virus NS3 protein contains an RNA helicase activity", *Biochem Biophys Res Commun.*, 215:160-6.
Klumpp, K., et al., (2008), "2'-deoxy-4'-azido nucleoside analogs are highly potent inhibitors of hepatitis C virus replication despite the lack of 2'-alpha-hydroxyl groups", *J Biol Chem.*, 283:2167-75.
Koonin, E., et al., (1993), "Evolution and taxonomy of positive-strand RNA viruses: implications of comparative analysis of amino acid sequences", *Crit Rev Biochem Mol Bio.*, 28:375-430.
Lee, V., (1997), "Hepatitis B virus infection", *N. Engl J Med.*, 337:1733-45.
Lee, W., et al., (2005), "Selective intracellular activation of a novel prodrug of the human immunodeficiency virus reverse transcriptase inhibitor tenofovir leads to preferential distribution and accumulation in lymphatic tissue", *Antibicrob Agents Chemother.*, 49:1898-906.
Lohmann, V., et al., (1997), "Biochemical properties of hepatitis C virus NS5B RNA-dependent RNA polymerase and identification of amino acid sequence motifs essential for enzymatic activity", *J Virol.*, 71:8416-28.
Lohmann, V., et al., (1998), "Biochemical and kinetic analyses of NS5B RNA-dependent RNA polymerase of the hepatitis C virus", *Virology*, 249:108-18.
Meyers, G., et al., (1996), "Molecular characterization of pestiviruses", *Adv Virus Res.*, 47:53- 118.
Moennig, V., et al., (1992), "The pestiviruses", *Adv Virus Res.*, 41:53-98.
Monath, T., (1988), "Japanese encephalitis—a plague of the Orient", *N. Engl J Med.*, 319:641-3.
Monath, T., (1988), "Japanese encephalitis—a plague of the Orient", *N Engl J Med.*, 319:641-3.
Morissette, S., et al., (2004), "High-throughput crystallization: polymorphs, salts, co-crystals and solvates of pharmaceutical solids", *Adv Drug Deliv Rev.*, 56:275-300.
Murakami, E., et al., (2007), "Mechanism of activation of beta-D-2'-deoxy-2'-fluoro-2'-c-methylcytidine and inhibition of hepatitis C virus NS5B RNA polymerase", *Antimicrob Agents Chemother.*, 51:503-9.
New Zealand Examination Report, dated Feb. 1, 2011, issued in New Zealand App. No. 585491,.
Ni, Z., et al., (2004), "Progress and development of small molecule HCV antivirals", *Curr Opin Drug Discov Devel.*, 7:446-59.
Office Action dated Jun. 9, 2013, issued in Chinese App. No. 20088012524.5, 2pp.
Office Action dated Oct. 8, 2012, issued in Chinese App. No. 200880125124.5, 3pp.
Opposition filed Jan. 25, 2010, in corresponding Chilean App. No. 3431-2008.
Rando, R., et al., (2000), "Development of novel nucleoside analogues for use against drug resistant strains of HIV-1", *Drug Discov Today*, 5:465-76.
Rice, C., (1996), "Flaviviridae: The Viruses and Their Replication", *Fields Virology* 3rd Edition, 1:931-58.
Shortnacy-Fowler, A., et al., (2001), "Synthesis and biological activity of 4'-C-hydroxymethy1-2'-fluoro-D-arabinofuranosylpurine nucleosides", *Nuclosides Nucleotides Nucleic Acids*, 20:747-50.
Shortnacy-Fowler, A., et al., (2001), "Synthesis and biological activity of 4'-C-hydroxymethy1-2'-fluro-D-arabinofuranosylpurine nucleosides", *Nucleosides Nucleotides Nucleic Acids*, 20:1583-98.
Sofia, M., et al., (2012), "Nucleoside, nucleotide, and non-nucleoside inhibitors of hepatitis C virus NS5B RNA-dependent RNA-polymerase", *J Med Chem.*, 55:2481-531.
Tan, S., (2002), "Hepatitis C therapeutics: current status and emerging strategies", *Nat Rev Drug Discov.*, 1:867-81.
Technical Examiner's Report dated Nov. 15, 2011, issued in corresponding Chilean App. No. 3431-2008, 18pp.
Technical Examiner's Report, dated Apr. 16, 2012, issued in Chilean App. No. 3431-2008, 18pp.
Technical Examiner's Report, issued in corresponding Peruvian App. No. 001947-2008/DIN, 19pp.
Tomei, L., et al., (1993), "NS3 is a serine protease required for processing of hepatitis C virus polyprotein", *J Virol.*, 67:4017-26.
Walker, M., et al., (2003), "Promising candidates for the treatment of chronic hepatitis C", *Expert Opin Investig Drugs*, 12:1269-80.
Warrener, P., et al., (1995), "Pestivirus NS3 (p80) protein possesses RNA helicase activity", *J Virol.*, 69:1720-6.
Wiskerchen, M., et al., (1991), "Pestivirus gene expression: protein p80 of bovine viral diarrhea virus is a proteinase involved in polyprotein processing", *Virology* 184:341-50.
Written Opinion of the International Searching Authority issued in PCT/US2008/083787 mailed Mar. 26, 2009.
Wu, J., et al., (2003), "Targeting NS5B RNA-dependent RNA polymerase for anti-HCV chemotherapy", *Drug Targets Infect Disord.*, 3:207-19.

(56) References Cited

OTHER PUBLICATIONS

Xu, J., et al., (1997), "Bovine viral diarrhea virus NS3 serine proteinase: polyprotein cleavage sites, cofactor requirements, and molecular model of an enzyme essential for pestivirus replication", *J Virol.*, 7:5312-22.
Yuan, Z., et al., (1997), "Expression, purification, and partial characterization of HCV RNA polymerase", *Biochem Biophys Res Commun.*, 232:231-5.
Zhong, W., et al., (1998), "Identification and characterization of an RNA-dependent RNA polymerase activity within the nonstructural protein 5B region of bovine viral diarrhea virus", *J Virol.*, 72:9365-9.

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: HBV DNA Forward Primer (1125nM forward primer)

<400> SEQUENCE: 1
ggacccctgc tcgtgttaca                                                    20

<210> SEQ ID NO 2
<211> LENGTH: 25
<212> TYPE: DNA
<213> ORGANISM: Artificial Sequence
<220> FEATURE:
<223> OTHER INFORMATION: HBV DNA Reverse Primer (1125nM reverse primer)

<400> SEQUENCE: 2
gagagaagtc caccacgagt ctaga                                              25

<210> SEQ ID NO 3
<211> LENGTH: 27
<212> TYPE: DNA
<213> ORGANISM: Artificial Sequence
<220> FEATURE:
<223> OTHER INFORMATION: HBV DNA Probe (250nM probe; including 5'-FAM
      label)

<400> SEQUENCE: 3
tgttgacaag aatcctcaca ataccac                                            27

<210> SEQ ID NO 4
<211> LENGTH: 23
<212> TYPE: DNA
<213> ORGANISM: Artificial Sequence
<220> FEATURE:
```

```
<223> OTHER INFORMATION: HCV DNA Sense Primer

<400> SEQUENCE: 4
agccatggcg ttagtatgag tgt                                           23

<210> SEQ ID NO 5
<211> LENGTH: 18
<212> TYPE: DNA
<213> ORGANISM: Artificial Sequence
<220> FEATURE:
<223> OTHER INFORMATION: HCV DNA Antisense Primer

<400> SEQUENCE: 5
ttccgcagac cactatgg                                                 18

<210> SEQ ID NO 6
<211> LENGTH: 20
<212> TYPE: DNA
<213> ORGANISM: Artificial Sequence
<220> FEATURE:
<223> OTHER INFORMATION: HCV DNA Probe (including 5'-FAM label and
      3'-TAMRA label)

<400> SEQUENCE: 6
cctccaggac cccccctccc                                               20
```

2',4'-SUBSTITUTED NUCLEOSIDES AS ANTIVIRAL AGENTS

FIELD

Embodiments of the invention are directed to compounds, methods, and compositions for use in the treatment of viral infections. More specifically embodiments of the invention are 2',4'-substituted nucleoside compounds useful for the treatment of viral infections, such as HIV, HCV, and HBV infections.

BACKGROUND

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 4.5 million infected people in the United States alone, according to the U.S. Center for Disease Control. According to the World Health Organization, there are more than 200 million infected individuals worldwide, with at least 3 to 4 million people being infected each year. Once infected, about 20% of people clear the virus, but the rest can harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their offspring. Current treatments for HCV infection, which are restricted to immunotherapy with recombinant interferon-α alone or in combination with the nucleoside analog ribavirin, are of limited clinical benefit as resistance develops rapidly. Moreover, there is no established vaccine for HCV. Consequently, there is an urgent need for improved therapeutic agents that effectively combat chronic HCV infection.

The HCV virion is an enveloped positive-strand RNA virus with a single oligoribonucleotide genomic sequence of about 9600 bases which encodes a polyprotein of about 3,010 amino acids. The protein products of the HCV gene consist of the structural proteins C, E1, and E2, and the nonstructural proteins NS2, NS3, NS4A and NS4B, and NS5A and NS5B. The nonstructural (NS) proteins are believed to provide the catalytic machinery for viral replication. The NS3 protease releases NS5B, the RNA-dependent RNA polymerase from the polyprotein chain. HCV NS5B polymerase is required for the synthesis of a double-stranded RNA from a single-stranded viral RNA that serves as a template in the replication cycle of HCV. Therefore, NS5B polymerase is considered to be an essential component in the HCV replication complex (K. Ishi, et al, Heptology, 1999, 29: 1227-1235; V. Lohmann, et al., Virology, 1998, 249: 108-118). Inhibition of HCV NS5B polymerase prevents formation of the double-stranded HCV RNA and therefore constitutes an attractive approach to the development of HCV-specific antiviral therapies.

HCV belongs to a much larger family of viruses that share many common features.

Flaviviridae Viruses

The Flaviviridae family of viruses comprises at least three distinct genera: pestiviruses, which cause disease in cattle and pigs; flaviviruses, which are the primary cause of diseases such as dengue fever and yellow fever; and hepaciviruses, whose sole member is HCV. The flavivirus genus includes more than 68 members separated into groups on the basis of serological relatedness (Calisher et al., J. Gen. Virol, 1993, 70, 37-43). Clinical symptoms very and include fever, encephalitis and hemorrhagic fever (Fields Virology, Editors: Fields, B. N., Knipe, D. M., and Howley, P. M., Lippincott-Raven Publishers, Philadelphia, Pa., 1996, Chapter 31, 931-959). Flaviviruses of global concern that are associated with human disease include the Dengue Hemorrhagic Fever viruses (DHF), yellow fever virus, shock syndrome and Japanese encephalitis virus (Halstead, S. B., Rev. Infect. Dis., 1984, 6, 251-264; Halstead, S. B., Science, 239: 476-481, 1988; Monath, T. P., New Eng. J. Med. 1988, 319, 641-643).

The pestivirus genus includes bovine viral diarrhea virus (BVDV), classical swine fever virus (CSFV, also called hog cholera virus) and border disease virus (BDV) of sheep (Moennig, V. et al. Adv. Vir. Res. 1992, 41, 53-98). Pestivirus infections of domesticated livestock (cattle, pigs, and sheep) cause significant economic losses worldwide. BVDV causes mucosal disease in cattle and is of significant economic importance to the livestock industry (Meyers, G. and Thiel, H. J., Advances in Virus Research, 1996, 47, 53-118; Moennig V., et al., Adv. Vir. Res. 1992, 41, 53-98). Human pestiviruses have not been as extensively characterized as the animal pestiviruses. However, serological surveys indicate considerable pestivirus exposure in humans.

Pestiviruses and hepaciviruses are closely related virus groups within the Flaviviridae family. Other closely related viruses in this family include GB virus A, GB virus A-like agents, GB virus-B and GB virus-C (also called hepatitis G virus, HGV). The hepacivirus group (hepatitis C virus; HCV) consists of a number of closely related but genotypically distinguishable viruses that infect humans. There are at least 6 HCV genotypes and more than 50 subtypes. Due to the similarities between pestiviruses and hepaciviruses, combined with the poor ability of hepaciviruses to grow efficiently in cell culture, bovine viral diarrhea virus (BVDV) is often used as a surrogate to study the HCV virus.

The genetic organization of pestiviruses and hepaciviruses is very similar. These positive stranded RNA viruses possess a single large open reading frame (ORF) encoding all the viral proteins necessary for virus replication. These proteins are expressed as a poly protein that is a co- and post-translationally processed by both cellular and virus-encoded proteinases to yield the mature viral proteins. The viral proteins responsible for the replication of the viral genome RNA are located within approximately the carboxy-terminal. Two-thirds of the ORF are termed non (NS) proteins. The genetic organization and polyprotein processing of the nonstructural protein portion of the ORF for pestiviruses and hepaciviruses is very similar. For both the pestiviruses and hepaciviruses, the mature nonstructural (NS proteins, in sequential order from the amino-terminus of the nonstructural protein coding region to the carboxy-terminus of the ORF, consist of p7, NS2, NS3, NS4A, NS4B, NS5A, and NS5B.

The NS proteins of pestiviruses and hepaciviruses share sequence domains that are characteristic of specific protein functions. For example, the NS3 proteins of viruses in both groups possess amino acid sequence motifs characteristic of serine proteinases and of helicases (Gorbalenya, et al., Nature, 1988, 333, 22; Bazan and Fletterick, Virology, 1989, 171, 637-639; Gorbalenyl, et al., Nucleic Acid Res., 1989, 17, 3889-3897). Similarly, the NS5B proteins of pestiviruses and hepaciviruses have the motifs characteristic of RNA-directed RNA polymerases (Koonin, E. V. and Dolja, V. V., Crit. Rev. Biochem. Molec. Biol., 1993, 28, 375-430).

The actual roles and functions of the NS proteins of pestiviruses and hepaciviruses in the lifecycle of the viruses are directly analogous. In both cases, the NS3 serine proteinase is responsible for all proteolytic processing of polyprotein precursors down stream of its position in the ORF (Wiskerchen and Collett, Virology, 1991, 184, 341-350; Bartenschlager et al., J. Virol. 1993, 67, 3835-3844; Eckart et al., Biochem. Biophys. Res. Comm. 1993, 192, 399-406; Grakoui et al., J. Virol. 1993, 67, 2832-2843; Grakoui et al., Proc. Natl. Acad. Aci. USA, 1993, 909, 10583-10587; Hijikata et al., J. Virol. 1993, 67, 4665-4675; Tome et al., J. Virol., 1993, 67, 4017-4026). The NS4A protein, in both cases, acts as a cofactor with the NS3 serine protease (Bartenschlager et al., J. Virol. 1994, 68, 5045-5055; failla et al., J. Virol., 1994, 68, 3753-3760; Xu et al., J. Virol., 1997, 71, 5312-5322). The NS3 protein of both viruses also functions as a helicase (Kim et al., Biochem Biophys. Res. Comm., 1995, 215, '160-166; Jin and Peterson, Arch. Biochem. Biophys., 1995, 323, 47-53; Warrener and Collett, J. Virol., 1995, 69, 1720-1726). Finally, the NS5B proteins of pestiviruses and hepaciviruses have the predicted RNA-directed RNA polymerase activity (Behrens et al., EMBO, 1996, 15, 12-22; Lechmann et al., J. Virol., 1997, 71, 8416-8428; Yuan et al., Biochem. Biophys. Res. Comm. 1997, 232, 231-235; Hagedorn PCT WO 97/12033; Zhong et al., J. Virol., 1998, 72, 9365-9369).

Currently, there are limited treatment options for individuals infected with hepatitis C virus. The current approved therapeutic option is the use of immunotherapy with recombinant interferon-α alone or in combination with the nucleoside analog ribavirin. This therapy is limited in its clinical effectiveness and only 50% of treated patients respond to therapy. Therefore, there is significant need for more effective and novel therapies to address the unmet medical need posed by HCV infection.

A number of potential molecular targets for drug development of direct acting antivirals for anti-HCV therapeutics have now been identified including, but not limited to, the NS2-NS3 autoprotease, the N3 protease, the N3 helicase and the NS5B polymerase. The RNA-dependent RNA polymerase is absolutely essential for replication of the single-stranded, positive sense, RNA genome and this enzyme has elicited significant interest among medicinal chemists.

Inhibitors of HCV NS5B as potential therapies for HCV infection have been reviewed: Tan, S. L., et al., Nature Rev. Drug Discov., 2002, 1, 867-881; Walker, M. P. et al., Exp. Opin. Investigational Drugs, 2003, 12, 1269-1280; Ni, Z-J., et al., Current Opinion in Drug Discovery and Development, 2004, 7, 446-459; Beaulieu, P. L., et al., Current Opinion in Investigational Drugs, 2004, 5, 838-850; Wu, J., et al., Current Drug Targets-Infectious Disorders, 2003, 3, 207-219; Griffith, R. C., et al., Annual Reports in Medicinal Chemistry, 2004, 39, 223-237; Carrol, S., et al., Infectious Disorders-Drug Targets, 20-06, 6, 17-29. The potential for the emergence of resistant HCV strains and the need to identify agents with broad genotype coverage supports the need for continuing efforts to identify novel and more effective nucleosides as HCV NS5B inhibitors. Nucleoside inhibitors of NS5b polymerase can act either as a non-natural substrate that results in chain termination or as a competitive inhibitor which competes with nucleotide binding to the polymerase. To function as a chain terminator the nucleoside analog must be taken up by the cell and converted in vivo to a triphosphate to compete for the polymerase nucleotide binding site. This conversion to the triphosphate is commonly mediated by cellular kinases which imparts additional structural requirements on a potential nucleoside polymerase inhibitor.

Despite the existence of efficient vaccines, hepatitis B virus (HBV) infection remains a major public health problem worldwide with 400 million chronic carriers. These infected patients are exposed to a risk of developing liver cirrhosis and hepatocellular carcinoma (Lee, W. M. 1997, N. Eng. J. Med., 337, 1733-1745). Currently, there are believed to be approximately 1.25 million chronic hepatitis B carriers just in the United States, with 200,000 people newly infected each year by contact with blood or body fluids.

Hepatitis B virus is second to tobacco as a cause of human cancer. The mechanism by which HBV induces cancer is unknown, although it is postulated that may directly trigger tumor development, or indirectly trigger tumor development through chronic inflammation, cirrhosis, and cell regeneration associated with the infection.

Hepatitis B virus has reached epidemic levels worldwide. After a two to six month incubation period in which the host is unaware of the infection, HBV infection can lead to acute hepatitis and liver damage, that causes abdominal pain, jaundice, and elevated blood levels of certain enzymes. HBV can cause fulminant hepatitis, a rapidly progressive, often fatal form of the disease in which massive sections of the liver are destroyed. Patients typically recover from acute viral hepatitis. In some patients, however, high levels of viral antigen persist in the blood for an extended, or indefinite, period, causing a chronic infection. Chronic infections can lead to chronic persistent hepatitis. Patients infected with chronic persistent HBV are most common in developing countries. By mid-1991, there were approximately 225 million chronic carriers of HBV in Asia alone, and worldwide, almost 300 million carriers. Chronic persistent hepatitis can cause fatigue, cirrhosis of the liver, and hepatocellular carcinoma, a primary liver cancer.

In western industrialized countries, high risk groups for HBV infection include those in contact with HBV carriers or their blood samples. The epidemiology of HBV is in fact very similar to that of HIV, which accounts for why HBV infection is common among patients with AIDS or HIV-associated infections. However, HBV is more contagious than HIV.

As is well known, acquired immune deficiency syndrome (AIDS) is a disease that severely compromises the human immune system, and that leads to death. The cause of AIDS has been determined to be the human immunodeficiency virus (HIV). To ameliorate suffering and to prolong the lives of infected hosts new compounds and methods of treating AIDS and attacking the HIV virus continue to be sought.

The preceding references and all other references cited in the present specification are hereby incorporated herein by reference.

SUMMARY

Embodiments of the invention are directed to novel 2',4'-substituted nucleoside derivatives for the treatment of viral infections in mammals. Thus, in one aspect, an antivirally effective nucleoside is a 2',4'-disubstituted 2'-deoxy-nucleoside (β-D or β-L), its 5'-mono-phosphate, its 5',3'-cyclic phosphate, its 5'-diphosphate and its 5'-triphosphate or its pharmaceutically acceptable salt (acidic or basic addition salt), hydrate, solvate, crystalline form or prodrug thereof of the general formula:

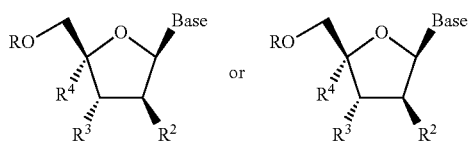

wherein (a) $R^2$ is independently $CH_3$, $CH_2F$, $CHF_2$, $CF_3$, F, CN, $C_{2-4}$ alkenyl, $C_{2-4}$ alkynyl, or $C_{1-4}$ alkyl optionally substituted with amino, hydroxy, or 1 to 3 fluorine atoms;

(b) R is H, phosphate, including 5'-monophosphate, 5',3'-cyclic phosphate, diphosphate, triphosphate, or a stabilized phosphate prodrug, H-phosphonate, including stabilized H-phosphonates, acyl, including optionally substituted phenyl and lower acyl, alkyl, including lower alkyl, O-substituted carboxyalkylamino or its peptide derivatives, sulfonate ester, including alkyl or arylalkyl sulfonyl, including methanesulfonyl and benzyl, wherein the phenyl group is optionally substituted, a lipid, including a phospholipid, an L or D-amino acid, a carbohydrate, a peptide, a cholesterol, or other pharmaceutically acceptable leaving group which when administered in vivo;

(c) $R^3$ is independently OH, H, $C_{1-4}$ alkyl, $C_{2-4}$ alkenyl, $C_{2-4}$ alkynyl, vinyl, $N_3$, CN, Cl, Br, F, I, $NO_2$, $C(O)O(C_{1-4}$ alkyl), $C(O)O(C_{1-4}$ alkyl), $C(O)O(C_{2-4}$ alkynyl), $C(O)O(C_{2-4}$ alkenyl), $O(C_{1-10}$ acyl), $O(C_{1-4}$ alkyl), $O(C_{2-4}$ alkenyl), SH, $S(C_{1-4}$ acyl), $S(C_{1-4}$ alkyl), $S(C_{2-4}$ alkynyl), $S(C_{2-4}$ alkenyl), $SO(C_{1-4}$ acyl), $SO(C_{1-4}$ alkyl), $SO(C_{2-4}$ alkynyl), $SO(C_{2-4}$ alkenyl), $SO_2(C_{1-4}$ acyl), $SO_2(C_{1-4}$ alkyl), $SO_2(C_{2-4}$ alkynyl), $SO_2(C_{2-4}$ alkenyl), $OS(O)_2(C_{1-4}$ acyl), $OS(O)_2(C_{1-4}$ alkyl), $OS(O)_2(C_{2-4}$ alkenyl), $NH_2$, $NH(C_{1-4}$ alkyl), $NH(C_{2-4}$ alkenyl), $NH(C_{2-4}$ alkynyl), $NH(C_{1-4}$ acyl), $N(C_{1-4}$ alkyl)$_2$, $N(C_{1-18}$ acyl)$_2$, wherein alkyl, alkynyl, alkenyl and vinyl are optionally substituted by $N_3$, CN, one to three halogen (Cl, Br, F, I), $NO_2$, $C(O)O(C_{1-4}$ alkyl), $C(O)O(C_{1-4}$ alkyl), $C(O)O(C_{2-4}$ alkynyl), $C(O)O(C_{2-4}$ alkenyl), $O(C_{1-4}$ acyl), $O(C_{1-4}$ alkyl), $O(C_{2-4}$ alkenyl), SH, $S(C_{1-4}$ acyl), $S(C_{1-4}$ alkyl), $S(C_{2-4}$ alkynyl), $S(C_{2-4}$ alkenyl), $SO(C_{1-4}$ acyl), $SO(C_{1-4}$ alkyl), $SO(C_{2-4}$ alkynyl), $SO(C_{2-4}$ alkenyl), $SO_2(C_{1-4}$ acyl), $SO_2(C_{1-4}$ alkyl), $SO_2(C_{2-4}$ alkynyl), $SO_2(C_{2-4}$ alkenyl), $OS(O)_2(C_{1-4}$ acyl), $OS(O)_2(C_{1-4}$ alkyl), $OS(O)_2(C_{2-4}$ alkenyl), $NH_2$, $NH(C_{1-4}$ alkyl), $NH(C_{2-4}$ alkenyl), $NH(C_{2-4}$ alkynyl), $NH(C_{1-4}$ acyl), $N(C_{1-4}$ alkyl)$_2$, $N(C_{1-4}$ acyl)$_2$;

(d) $R^4$ is independently H, a lower alkyl, CN, vinyl, O-(lower alkyl), hydroxyl lower alkyl, i.e., $—(CH_2)_pOH$, where p is 1-6, including hydroxyl methyl ($CH_2OH$), $CH_2F$, $N_3$, $CH_2CN$, $CH_2NH_2$, $CH_2NHCH_3$, $CH_2N(CH_3)_2$, ethynyl alkyne (optionally substituted), or halogen, including F, Cl, Br, or I, alkenyl, alkynyl, Br-vinyl, hydroxy, O-alkenyl, $NO_2$, amino, loweralkylamino, or di(loweralkyl)amino;

(e) R and $R^3$ can together form 5',3'-cyclic phosphate including stabilized prodrugs thereof;

(f) Base (B) is a naturally occurring or modified purine or pyrimidine base represented by the following structures:

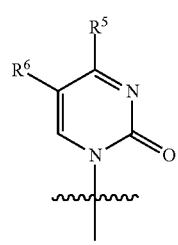

a

-continued

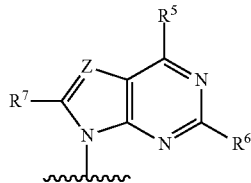

b wherein for a and b

Z is N or $CR^8$;

$R^5$, $R^6$, and $R^7$ are independently H, F, Cl, Br, I, OH, OR', SH, SR', $NH_2$, NHR', $NR'_2$ (two R' can form saturated or unsaturated rings, or saturated or unsaturated heterocyclic rings), lower alkyl of $C_1$-$C_6$, halogenated (F, Cl, Br, I) lower alkyl of $C_1$-$C_6$, lower alkenyl of $C_2$-$C_6$, halogenated (F, Cl, Br, I) lower alkenyl of $C_2$-$C_6$, lower alkynyl of $C_2$-$C_6$ such as $C≡CH$, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, $CH=CHCO_2H$, or $CH=CHCO_2R'$, wherein R' is an optionally substituted alkyl, which includes, but is not limited to, an optionally substituted $C_{1-20}$ alkyl, an optionally substituted $C_{1-10}$ alkyl, an optionally substituted lower alkyl; an optionally substituted cycloalkyl; an optionally substituted alkynyl of $C_2$-$C_6$, an optionally substituted lower alkenyl of $C_2$-$C_6$, or optionally substituted acyl, which includes but is not limited to C(O)alkyl, $C(O)(C_{1-20}$ alkyl), $C(O)(C_{1-10}$ alkyl), or C(O)(lower alkyl), optionally substituted aryl, optionally substituted $C_1$-$C_4$ alkyl-aryloxy, heteroaryl, optionally substituted $C_1$-$C_4$ alkyl-heteroaryl, an optionally substituted alkoxy $C_{1-20}$ alkyl, an optionally substituted amino $C_{1-20}$ alkyl, an optionally substituted fluoro $C_{1-20}$ alkyl;

$R^8$ is independently H, halogen (including F, Cl, Br, I), OH, OR', SH, SR', $NH_2$, NHR', $NR'_2$ (two R' can form saturated or unsaturated rings, or saturated or unsaturated heterocyclic rings), $NO_2$, lower alkyl of $C_1$-$C_6$, halogenated (F, Cl, Br, I) lower alkyl of $C_1$-$C_6$, lower alkenyl of $C_2$-$C_6$, halogenated (F, Cl, Br, I) lower alkenyl of $C_2$-$C_6$, lower alkynyl of $C_2$-$C_6$, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, $CH=CHCO_2H$, or $CH=CHCO_2R'$ wherein R' is an optionally substituted alkyl, which includes, but is not limited to, an optionally substituted $C_{1-20}$ alkyl, an optionally substituted $C_{1-10}$ alkyl, an optionally substituted lower alkyl; an optionally substituted cycloalkyl; an optionally substituted alkynyl of $C_2$-$C_6$, an optionally substituted lower alkenyl of $C_2$-$C_6$, or optionally substituted acyl, which includes but is not limited to C(O) alkyl, $C(O)(C_{1-20}$ alkyl), $C(O)(C_{1-10}$ alkyl), or C(O)(lower alkyl), optionally substituted aryl, optionally substituted $C_1$-$C_4$ alkyl-aryloxy, heteroaryl, optionally substituted $C_1$-$C_4$ alkyl-heteroaryl, an optionally substituted alkoxy $C_{1-20}$ alkyl, an optionally substituted amino $C_{1-20}$ alkyl, an optionally substituted fluoro $C_{1-20}$ alkyl; or base (B) may be selected from a group of formula c

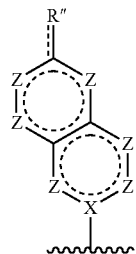

c wherein for structure c,
if Z is a participant in a pi bond (double bond), Z is independently selected from N or C-G; or, if Z is not a participant in a pi bond (double bond), Z is independently selected from O, S, Se, NR, NOR, NNR$_2$, CO, CS, CNR, SO, S(O)$_2$, SeO, Se(O)$_2$, or C(G)$_2$;
each G is independently selected from the group consisting of H, halogen, OR, SR, NR$_2$, NROR, N$_3$, COOR, CN, CONR$_2$, C(S)NR$_2$, C(=NR)NR$_2$, and R; and where any two adjacent Z are not both selected from O, S, and Se, or not both selected from CO, CS, CNNR, SO, S(O)$_2$, SeO and Se(O)$_2$;
wherein, if X is a participant in a pi bond (double bond), X is C; or if X is not a participant in a pi bond (double bond), X is CR or N;
wherein, if R″ is a participant in a pi bond (double bond), R″ is O, S, Se, NR, NOR or NNR$_2$; or if R″ is not a participant in a pi bond (double bond), R″ is OR, SR, F, Cl, R, or SeR; and
dashed lines (---) indicate a possible pi or double bond;
each R is independently selected from the group consisting of H, CF$_3$, optionally substituted alkyl, optionally substituted alkenyl, optionally substituted alkynyl, optionally substituted aryl, optionally substituted acyl, optionally substituted cycloalkyl, optionally substituted cycloalkenyl, optionally substituted heteroaryl, optionally substituted heterocyclyl, and optionally substituted arylalkyl; or
base (B) may be a structure selected from the group consisting of structures d-n

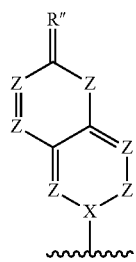

d

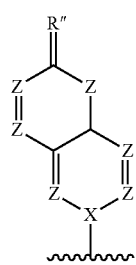

e

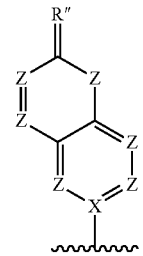

f

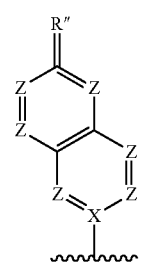

g

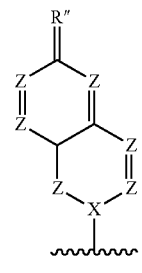

h

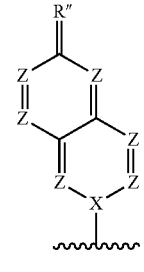

i

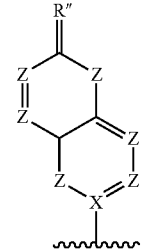

j

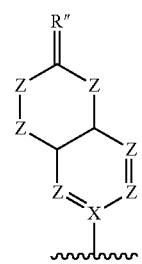

k l
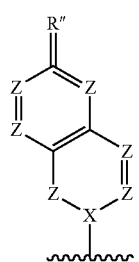
m
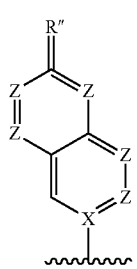
n
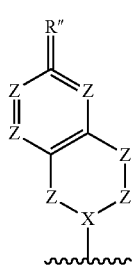
wherein Z, X, and R" are defined as in structure c;
base may be a structure selected from the group consisting of structures o-ff
o
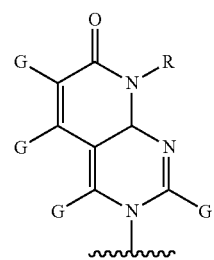
p
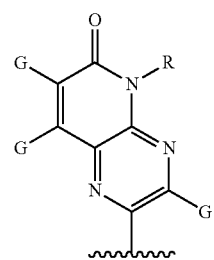
q
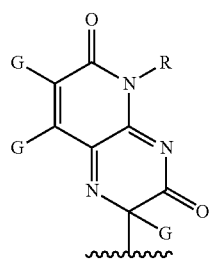
r
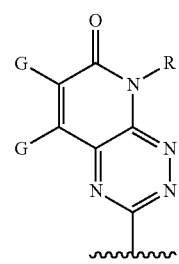
s
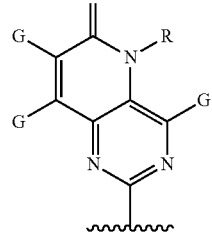
t
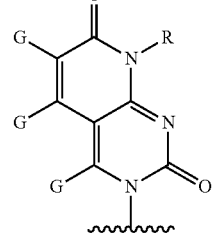
u
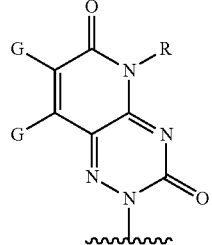
v
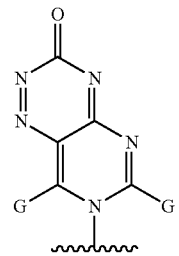

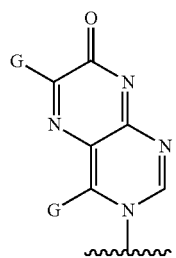
w
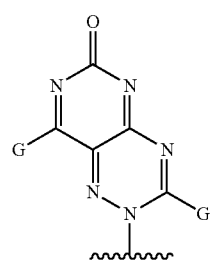
x
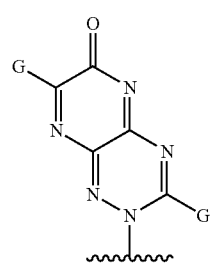
y
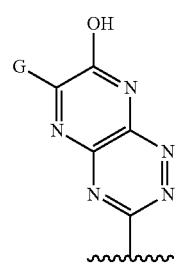
z
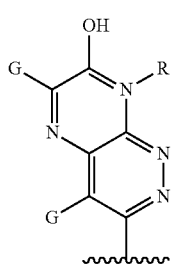
aa
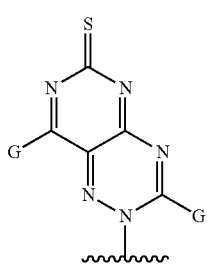
bb
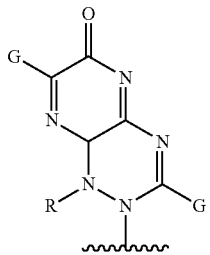
cc
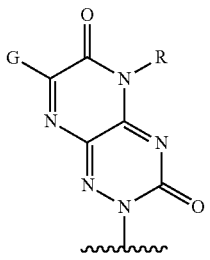
dd
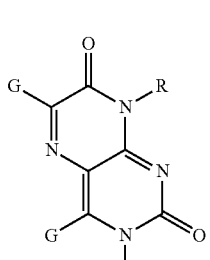
ee
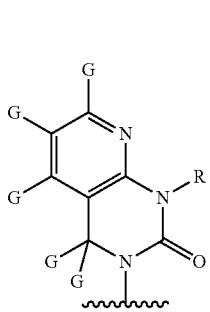
ff
wherein G and R are defined as in structure c;
base (B) may be a structure gg
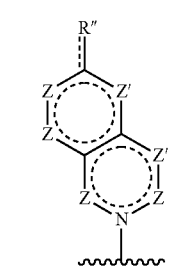
gg wherein each Z' is independently N (if a participant in a pi bond) or NR (if not a participant in a pi bond) and R", R, and Z are defined as in structure c;

base (B) may be a structure hh

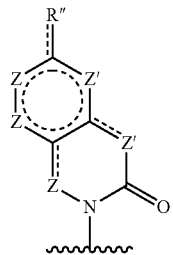

wherein each Z' is independently N (if a participant in a pi bond) or NR (if not a participant in a pi bond), and each Z in independently CG (if a participant in a pi bond) or >C(G)2 (if not a participant in a pi bond), wherein R" and G are defined as in structure c;

base (B) may be a structure ii

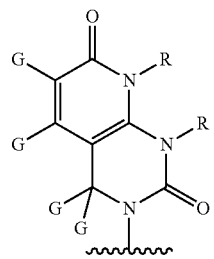

wherein R and G are defined as in structure c;
base may be a structure jj

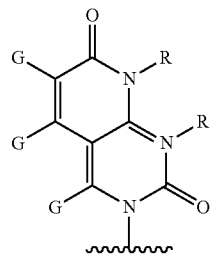

wherein R and G are defined as in structure c; or
base may be a structure kk

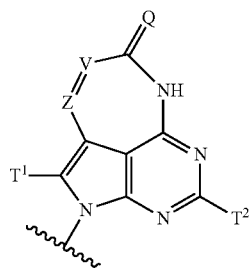

wherein for structure kk:
R is selected from the group consisting of hydrogen and $C_1$-$C_3$ alkyl;

X is selected from the group consisting of hydrogen, halo, and $OW^2$;

Y is selected from the group consisting of a bond, O, and $CH_2$;

Q is absent or is selected from the group consisting of O, S, and NH, provided that when Q is absent, V and NH are both attached to a $CH_2$ group;

V is selected from the group consisting of N and C-G;

Z is selected from the group consisting of N and C-G;

G and G' are independently selected from the group consisting of hydrogen, amino, aminocarbonyl, methylamino, dimethylamino, acylamino, alkoxyamino, —$SO_3H$, —$SO_2NH_2$, aminocarbonylamino, oxycarbonylamino, HR'NCHR"C(O)NH—, azido, cyano, halo, hydroxyamino, and hydrazino, where R' is hydrogen and R" is a side-chain of an amino acid or where R' and R" together with the nitrogen and carbon bound to each group respectively form a pyrrolidinyl group;

provided that V and Z are not identical;

provided that when V is C—H, Z is N;

$T^1$ and $T^2$ are independently selected from the group consisting of hydrogen, hydroxyl, $C_1$-$C_4$-alkoxy, $C_1$-$C_4$-thioalkoxy, amino, substituted amino, and halo; and each of W, $W^1$, and $W^2$ is independently selected from the group consisting of hydrogen, $C_1$-$C_4$ alkyl, and a prodrug group; or base may be a structure ll

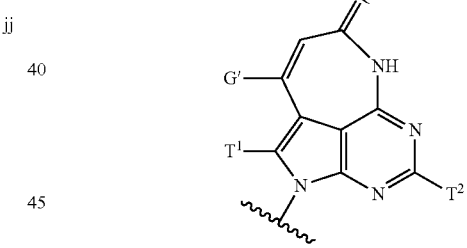

wherein for structure ll:
R is $C_1$-$C_3$ alkyl;
X is selected from the group consisting of hydrogen, halo, and $OW^2$;
Q' is selected from the group consisting of NH, O, and S;
G' is selected from the group consisting of amino, aminocarbonyl, methylamino, dimethylamino, acylamino, —$SO_3H$, —$SO_2NH_2$, alkoxyamino, aminocarbonylamino, oxycarbonylamino, HR'NCHR"C(O)NH—, azido, cyano, halo, hydroxyamino, and hydrazino, where R' is hydrogen and R" is a side-chain of an amino acid or where R' and R" together with the nitrogen and carbon bound to each group respectively form a pyrrolidinyl group; Y is selected from the group consisting of a bond, O, and $CH_2$; and each of W, $W^1$, and $W^2$ is independently selected from the group consisting of hydrogen, $C_1$-$C_4$ alkyl, and a prodrug group; or base may be a structure mm

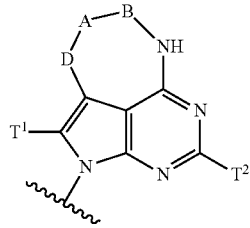

where in for structure mm

Q is as defined for structure kk

A and B are independently selected from the group consisting of C=Q, NH, and methylene optionally substituted with 1 to 2 halo groups, provided that A and B are not both NH;

D is NH, or -D-A-B— together form a —N=CH—NH—, —(C=Q)-$CH_2$—(C=Q)-, —(C=Q)-NH—(C=Q)-, —(CX')=(CX')—(C=Q)-, or —CH=CH—NH— group where X' is halo;

each Q is independently selected from the group consisting of O, S, and NH; R is selected from the group consisting of hydrogen and $C_1$-$C_3$ alkyl;

X is selected from the group consisting of hydrogen, halo, and $OW^2$;

$T^1$ and $T^2$ are independently selected from the group consisting of hydrogen, hydroxyl, $C_1$-$C_4$-alkoxy, $C_1$-$C_4$-thioalkoxy, amino, substituted amino, and halo;

Y is selected from the group consisting of a bond, O, and $CH_2$; and each of W, $W^1$, and $W^2$ is independently selected from the group consisting of hydrogen, $C_1$-$C_4$ alkyl, and a prodrug group;

and pharmaceutically acceptable salts, tautomers, pharmaceutically acceptable salts of tautomers, salts (acidic or basic addition salts), hydrates, solvates, crystalline forms thereof; optionally in combination with one or more antiviral, antibacterial, or antiproliferative agents.

It is an object of embodiments of the invention to provide a compound, method, and composition for the treatment or prevention of HIV, HBV, or HCV infection in a host. It is a further object of embodiments of the invention to provide a compound, method, and composition for the treatment or prevention of HIV, HBV, or HCV when the host is a human, or when the host is an animal.

DETAILED DESCRIPTION

Embodiments of the invention are directed to novel 2',4'-substituted nucleoside derivatives for the treatment is viral infections in mammals, comprised of one or more compounds of the formula:

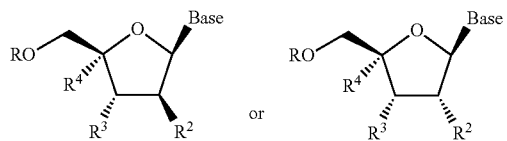

wherein (a) $R^2$ is independently $CH_3$, $CH_2F$, $CHF_2$, $CF_3$, F, CN, $C_{2-4}$ alkenyl, $C_{2-4}$ alkynyl, or $C_{1-4}$ alkyl optionally substituted with amino, hydroxy, or 1 to 3 fluorine atoms;

(b) R is H, phosphate, including 5'-monophosphate, 5',3'-cyclic phosphate, diphosphate, triphosphate, or a stabilized phosphate prodrug, H-phosphonate, including stabilized H-phosphonates, acyl, including optionally substituted phenyl and lower acyl, alkyl, including lower alkyl, O-substituted carboxyalkylamino or its peptide derivatives, sulfonate ester, including alkyl or arylalkyl sulfonyl, including methanesulfonyl and benzyl, wherein the phenyl group is optionally substituted, a lipid, including a phospholipid, an L or D-amino acid, a carbohydrate, a peptide, a cholesterol, or other pharmaceutically acceptable leaving group which when administered in vivo;

(c) $R^3$ is independently OH, H, $C_{1-4}$ alkyl, $C_{2-4}$ alkenyl, $C_{2-4}$ alkynyl, vinyl, $N_3$, CN, Cl, Br, F, I, $NO_2$, $C(O)O(C_{1-4}$ alkyl), $C(O)O(C_{1-4}$ alkyl), $C(O)O(C_{2-4}$ alkynyl), $C(O)O(C_{2-4}$ alkenyl), $O(C_{1-10}$ acyl), $O(C_{1-4}$ alkyl), $O(C_{2-4}$ alkenyl), SH, $S(C_{1-4}$ acyl), $S(C_{1-4}$ alkyl), $S(C_{2-4}$ alkynyl), $S(C_{2-4}$ alkenyl), $SO(C_{1-4}$ acyl), $SO(C_{1-4}$ alkyl), $SO(C_{2-4}$ alkynyl), $SO(C_{2-4}$ alkenyl), $SO_2(C_{1-4}$ acyl), $SO_2(C_{1-4}$ alkyl), $SO_2(C_{2-4}$ alkynyl), $SO_2(C_{2-4}$ alkenyl), $OS(O)_2(C_{1-4}$ acyl), $OS(O)_2(C_{1-4}$ alkyl), $OS(O)_2(C_{2-4}$ alkenyl), $NH_2$, $NH(C_{1-4}$ alkyl), $NH(C_{2-4}$ alkenyl), $NH(C_{2-4}$ alkynyl), $NH(C_{1-4}$ acyl), $N(C_{1-4}$ alkyl)$_2$, $N(C_{1-18}$ acyl)$_2$, wherein alkyl, alkynyl, alkenyl and vinyl are optionally substituted by $N_3$, CN, one to three halogen (Cl, Br, F, I), $NO_2$, $C(O)O(C_{1-4}$ alkyl), $C(O)O(C_{1-4}$ alkyl), $C(O)O(C_{2-4}$ alkynyl), $C(O)O(C_{2-4}$ alkenyl), $O(C_{1-4}$ acyl), $O(C_{1-4}$ alkyl), $O(C_{2-4}$ alkenyl), SH, $S(C_{1-4}$ acyl), $S(C_{1-4}$ alkyl), $S(C_{2-4}$ alkynyl), $S(C_{2-4}$ alkenyl), $SO(C_{1-4}$ acyl), $SO(C_{1-4}$ alkyl), $SO(C_{2-4}$ alkynyl), $SO(C_{2-4}$ alkenyl), $SO_2(C_{1-4}$ acyl), $SO_2(C_{1-4}$ alkyl), $SO_2(C_{2-4}$ alkynyl), $SO_2(C_{2-4}$ alkenyl), $OS(O)_2(C_{1-4}$ acyl), $OS(O)_2(C_{1-4}$ alkyl), $OS(O)_2(C_{2-4}$ alkenyl), $NH_2$, $NH(C_{1-4}$ alkyl), $NH(C_{2-4}$ alkenyl), $NH(C_{2-4}$ alkynyl), $NH(C_{1-4}$ acyl), $N(C_{1-4}$ alkyl)$_2$, $N(C_{1-4}$ acyl)$_2$;

(d) $R^4$ is independently H, a lower alkyl, CN, vinyl, O-(lower alkyl), hydroxyl lower alkyl, i.e., —$(CH_2)_pOH$, where p is 1-6, including hydroxyl methyl ($CH_2OH$), $CH_2F$, $N_3$, $CH_2CN$, $CH_2NH_2$, $CH_2NHCH_3$, $CH_2N(CH_3)_2$, ethynyl alkyne (optionally substituted), or halogen, including F, Cl, Br, or I, alkenyl, alkynyl, Br-vinyl, hydroxy, O-alkenyl, $NO_2$, amino, loweralkylamino, or di(loweralkyl)amino;

(e) R and $R^3$ can together form 5',3'-cyclic phosphate including stabilized prodrugs thereof;

(f) Base is a naturally occurring or modified purine or pyrimidine base represented by the following structures:

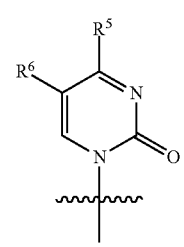

a

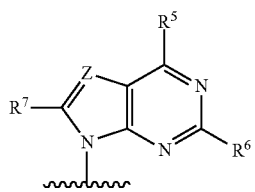

b wherein for a and b

Z is N or CR$^8$;

R$^5$, R$^6$, and R$^7$ are independently H, F, Cl, Br, I, OH, OR', SH, SR', NH$_2$, NHR', NR'$_2$ (two R' can form saturated or unsaturated rings, or saturated or unsaturated heterocyclic rings), lower alkyl of C$_1$-C$_6$, halogenated (F, Cl, Br, I) lower alkyl of C$_1$-C$_6$, lower alkenyl of C$_2$-C$_6$, halogenated (F, Cl, Br, I) lower alkenyl of C$_2$-C$_6$, lower alkynyl of C$_2$-C$_6$ such as C≡CH, halogenated (F, Cl, Br, I) lower alkynyl of C$_2$-C$_6$, lower alkoxy of C$_1$-C$_6$, halogenated (F, Cl, Br, I) lower alkoxy of C$_1$-C$_6$, CO$_2$H, CO$_2$R', CONH$_2$, CONHR', CONR'$_2$, CH=CHCO$_2$H, or CH=CHCO$_2$R' wherein R' is an optionally substituted alkyl, which includes, but is not limited to, an optionally substituted C$_{1-20}$ alkyl, an optionally substituted C$_{1-10}$ alkyl, an optionally substituted lower alkyl; an optionally substituted cycloalkyl; an optionally substituted alkynyl of C$_2$-C$_6$, an optionally substituted lower alkenyl of C$_2$-C$_6$, or optionally substituted acyl, which includes but is not limited to C(O) alkyl, C(O)(C$_{1-20}$ alkyl), C(O)(C$_{1-10}$ alkyl), or C(O)(lower alkyl), optionally substituted aryl, optionally substituted C$_1$-C$_4$ alkyl-aryloxy, heteroaryl, optionally substituted C$_1$-C$_4$ alkyl-heteroaryl, an optionally substituted alkoxy C$_{1-20}$ alkyl, an optionally substituted amino C$_{1-20}$ alkyl, an optionally substituted fluoro C$_{1-20}$ alkyl;

R$^8$ is independently H, halogen (including F, Cl, Br, I), OH, OR', SH, SR', NH$_2$, NHR', NR'$_2$ (two R' can form saturated or unsaturated rings, or saturated or unsaturated heterocyclic rings), NO$_2$, lower alkyl of C$_1$-C$_6$, halogenated (F, Cl, Br, I) lower alkyl of C$_1$-C$_6$, lower alkenyl of C$_2$-C$_6$, halogenated (F, Cl, Br, I) lower alkenyl of C$_2$-C$_6$, lower alkynyl of C$_2$-C$_6$, halogenated (F, Cl, Br, I) lower alkynyl of C$_2$-C$_6$, lower alkoxy of C$_1$-C$_6$, halogenated (F, Cl, Br, I) lower alkoxy of C$_1$-C$_6$, CO$_2$H, CO$_2$R', CONH$_2$, CONHR', CONR'$_2$, CH=CHCO$_2$H, or CH=CHCO$_2$R', wherein R' is an optionally substituted alkyl, which includes, but is not limited to, an optionally substituted C$_{1-20}$ alkyl, an optionally substituted C$_{1-10}$ alkyl, an optionally substituted lower alkyl; an optionally substituted cycloalkyl; an optionally substituted alkynyl of C$_2$-C$_6$, an optionally substituted lower alkenyl of C$_2$-C$_6$, or optionally substituted acyl, which includes but is not limited to C(O) alkyl, C(O)(C$_{1-20}$ alkyl), C(O)(C$_{1-10}$ alkyl), or C(O)(lower alkyl), optionally substituted aryl, optionally substituted C$_1$-C$_4$ alkyl-aryloxy, heteroaryl, optionally substituted C$_1$-C$_4$ alkyl-heteroaryl, an optionally substituted alkoxy C$_{1-20}$ alkyl, an optionally substituted amino C$_{1-20}$ alkyl, an optionally substituted fluoro C$_{1-20}$ alkyl; or base may be selected from a group of formula c

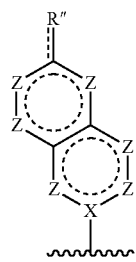

c wherein for structure c, if Z is a participant in a pi bond (double bond), Z is independently selected from N or C-G; or, if Z is not a participant in a pi bond (double bond), Z is independently selected from O, S, Se, NR, NOR, NNR$_2$, CO, CS, CNR, SO, S(O)$_2$, SeO, Se(O)$_2$, or C(G)$_2$;

each G is independently selected from the group consisting of H, halogen, OR, SR, NR$_2$, NROR, N$_3$, COOR, CN, CONR$_2$, C(S)NR$_2$, C(=NR)NR$_2$, and R; and where any two adjacent Z are not both selected from O, S, and Se, or not both selected from CO, CS, CNNR, SO, S(O)$_2$, SeO and Se(O)$_2$;

wherein, if X is a participant in a pi bond (double bond), X is C; or if X is not a participant in a pi bond (double bond), X is CR or N;

wherein, if R" is a participant in a pi bond (double bond), R" is O, S, Se, NR, NOR or NNR$_2$; or if R" is not a participant in a pi bond (double bond), R" is OR, SR, F, Cl, R, or SeR; and dashed lines (---) indicate a possible pi or double bond;

each R is independently selected from the group consisting of H, CF$_3$, optionally substituted alkyl, optionally substituted alkenyl, optionally substituted alkynyl, optionally substituted aryl, optionally substituted acyl, optionally substituted cycloalkyl, optionally substituted cycloalkenyl, optionally substituted heteroaryl, optionally substituted heterocyclyl, and optionally substituted arylalkyl; or base may be a structure selected from the group consisting of structures d-n

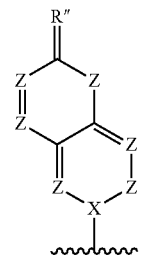

d

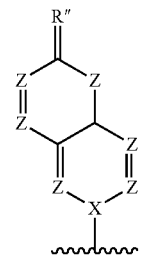

e

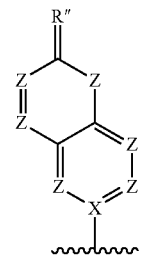

f g 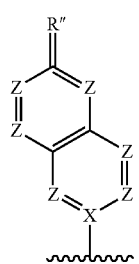
h 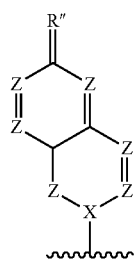
i 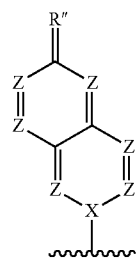
j 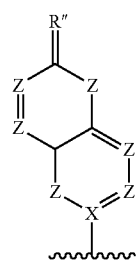
k 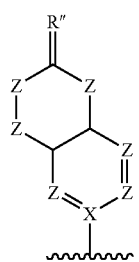
l 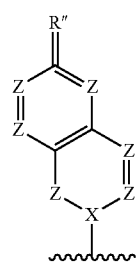
m 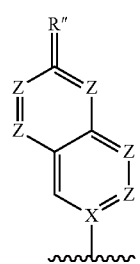
n 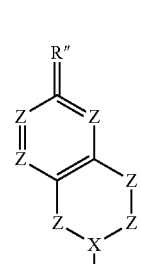
wherein Z, X, and R" are defined as in structure c;
base may be a structure selected from the group consisting of structures o-ff
o 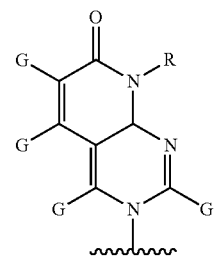
p 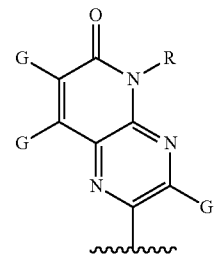
q 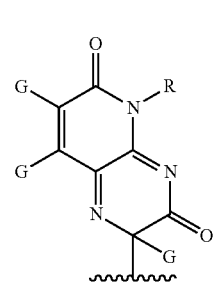

21
-continued
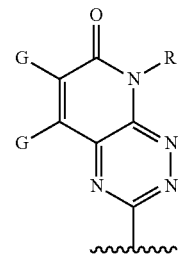
r
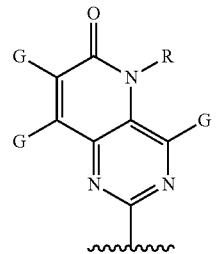
s
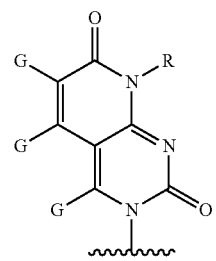
t
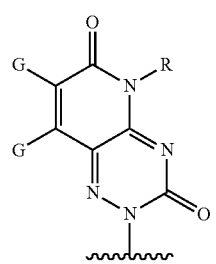
u
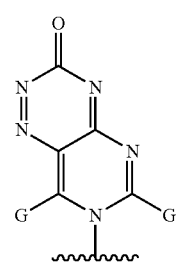
v
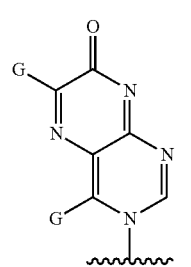
w
22
-continued
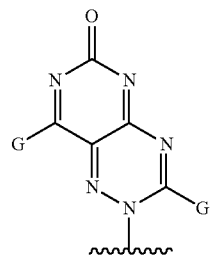
x
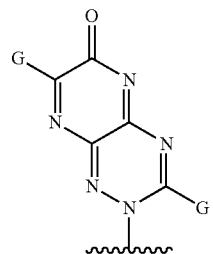
y
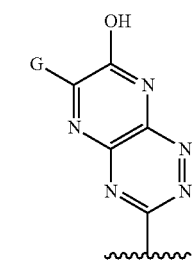
z
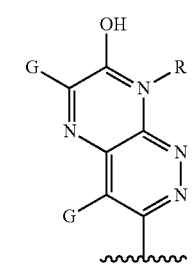
aa
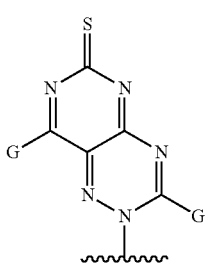
bb
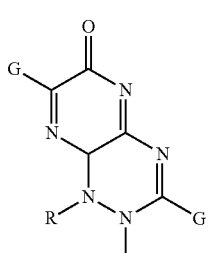
cc -continued

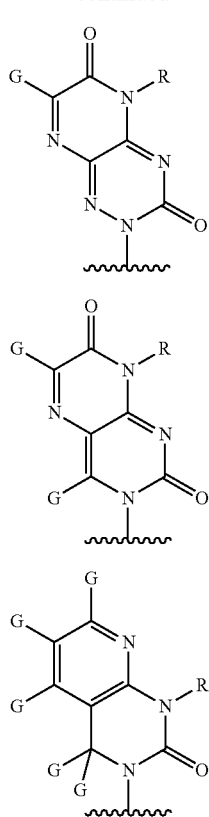

wherein G and R are defined as in structure c;
base may be a structure gg

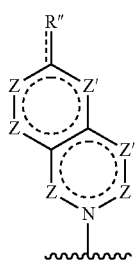

wherein each Z' is independently N (if a participant in a pi bond) or NR (if not a participant in a pi bond) and R", R, and Z are defined as in structure c;
base may be a structure hh

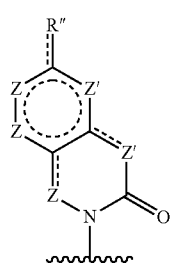

wherein each Z' is independently N (if a participant in a pi bond) or NR (if not a participant in a pi bond), and each Z in independently CG (if a participant in a pi bond) or >C(G)2 (if not a participant in a pi bond), wherein R" and G are defined as in structure c;
base may be a structure ii

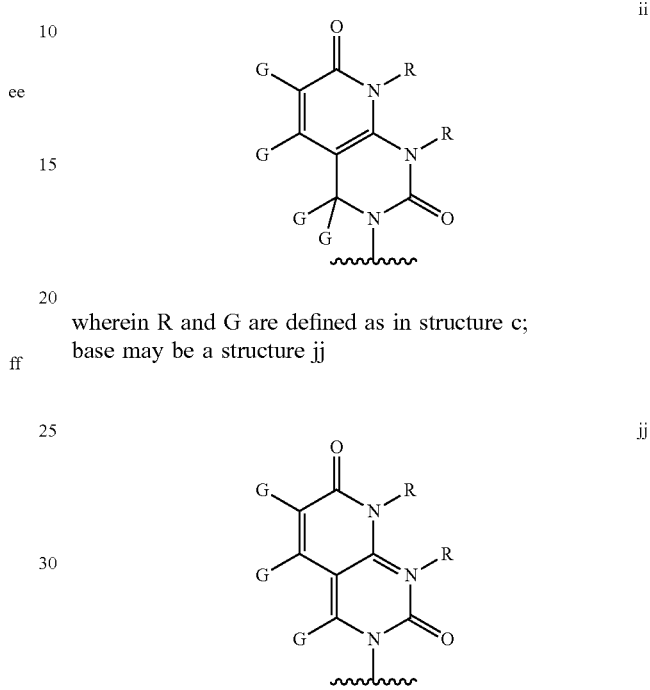

wherein R and G are defined as in structure c;
base may be a structure jj

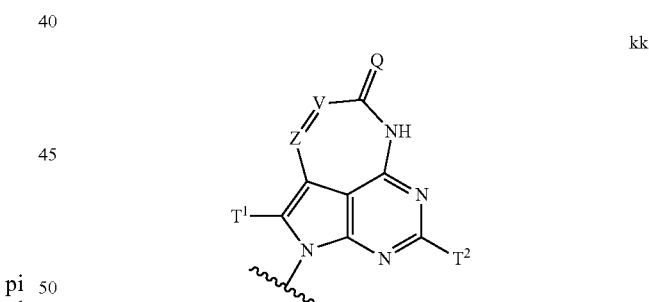

wherein R and G are defined as in structure c; or
base may be a structure kk wherein for structure kk:
R is selected from the group consisting of hydrogen and $C_1$-$C_3$ alkyl;
X is selected from the group consisting of hydrogen, halo, and $OW^2$;
Y is selected from the group consisting of a bond, O, and $CH_2$;
Q is absent or is selected from the group consisting of O, S, and NH, provided that when Q is absent, V and NH are both attached to a $CH_2$ group;
V is selected from the group consisting of N and C-G;
Z is selected from the group consisting of N and C-G;
G and G' are independently selected from the group consisting of hydrogen, amino, aminocarbonyl, methylamino, dimethylamino, acylamino, alkoxyamino, —$SO_3H$, —SO$_2$NH$_2$, aminocarbonylamino, oxycarbonylamino, HR'NCHR"C(O)NH—, azido, cyano, halo, hydroxyamino, and hydrazino, where R' is hydrogen and R" is a side-chain of an amino acid or where R' and R" together with the nitrogen and carbon bound to each group respectively form a pyrrolidinyl group;
provided that V and Z are not identical;
provided that when V is C—H, Z is N;
T$^1$ and T$^2$ are independently selected from the group consisting of hydrogen, hydroxyl, C$_1$-C$_4$-alkoxy, C$_1$-C$_4$-thioalkoxy, amino, substituted amino, and halo; and
each of W, W$^1$, and W$^2$ is independently selected from the group consisting of hydrogen, C$_1$-C$_4$ alkyl, and a prodrug group; or
base may be a structure ll

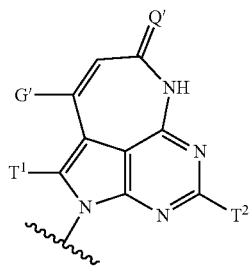

ll wherein for structure ll:
R is C$_1$-C$_3$ alkyl;
X is selected from the group consisting of hydrogen, halo, and OW$^2$;
Q' is selected from the group consisting of NH, O, and S;
G' is selected from the group consisting of amino, aminocarbonyl, methylamino, dimethylamino, acylamino, —SO$_3$H, —SO$_2$NH$_2$, alkoxyamino, aminocarbonylamino, oxycarbonylamino, HR'NCHR"C(O)NH—, azido, cyano, halo, hydroxyamino, and hydrazino, where R' is hydrogen and R" is a side-chain of an amino acid or where R' and R" together with the nitrogen and carbon bound to each group respectively form a pyrrolidinyl group; Y is selected from the group consisting of a bond, O, and CH$_2$; and each of W, W$^1$, and W$^2$ is independently selected from the group consisting of hydrogen, C$_1$-C$_4$ alkyl, and a prodrug group; or
base may be a structure mm

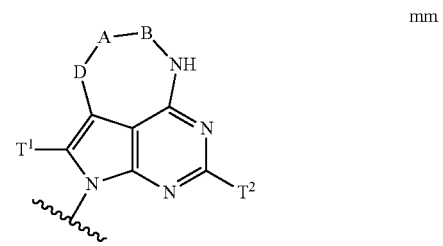

mm where in for structure mm
Q is as defined for structure kk
A and B are independently selected from the group consisting of C=Q, NH, and methylene optionally substituted with 1 to 2 halo groups, provided that A and B are not both NH; D is NH, or -D-A-B— together form a —N=CH—NH—, —(C=Q)-CH$_2$—(C=Q)-, —(C=Q)-NH—(C=Q)-, —(CX')=(CX')—(C=Q)-, or —CH=CH—NH— group where X' is halo;
each Q is independently selected from the group consisting of O, S, and NH; R is selected from the group consisting of hydrogen and C$_1$-C$_3$ alkyl;
X is selected from the group consisting of hydrogen, halo, and OW$^2$;
T$^1$ and T$^2$ are independently selected from the group consisting of hydrogen, hydroxyl, C$_1$-C$_4$-alkoxy, C$_1$-C$_4$-thioalkoxy, amino, substituted amino, and halo;
Y is selected from the group consisting of a bond, O, and CH$_2$; and each of W, W$^1$, and W$^2$ is independently selected from the group consisting of hydrogen, C$_1$-C$_4$ alkyl, and a prodrug group;
and pharmaceutically acceptable salts, tautomers, pharmaceutically acceptable salts of tautomers, salts (acidic or basic addition salts), hydrates, solvates, crystalline forms thereof; optionally in combination with one or more antiviral, antibacterial, or antiproliferative agents.

Particularly preferred embodiments of the invention are listed, but not limited, in Tables I and II below.

TABLE I

| R$^2$ | R$^3$ | R$^4$ | R$^5$ | X | R$^6$ |
|---|---|---|---|---|---|
| CH$_3$ | OH | N$_3$ | NH$_2$, NH—NH$_2$, NH—OH, OH, SH, | O, S | H, CH$_3$, F, Cl, Br, I, NO$_2$, CH=CH$_2$, CH=CHBr, CH=CHCl, C≡CH, CN, NH$_2$, CH$_2$OH |
| CH$_3$ | OH | C≡CH | NH$_2$, NH—NH$_2$, NH—OH, OH, SH, | O, S | H, CH$_3$F, Cl, Br, I, NO$_2$, CH=CH$_2$, CH=CHBr, CH=CHCl, C≡CH, CN, NH$_2$, CH$_2$OH |

TABLE I-continued

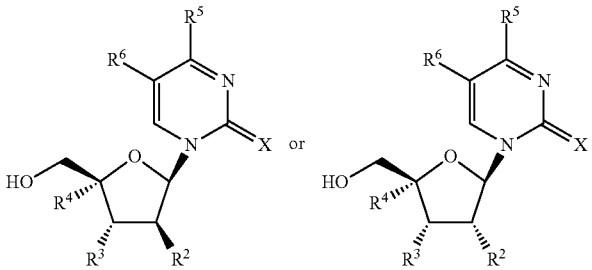

| R² | R³ | R⁴ | R⁵ | X | R⁶ |
|---|---|---|---|---|---|
| $CH_3$ | OH | $CH=CH_2$ | $NH_2$, $NH-NH_2$, $NH-OH$, OH, SH | O, S | H, $CH_3$, F, Cl, Br, I, $NO_2$, $CH=CH_2$, $CH=CHBr$, $CH=CHCl$, $C≡CH$, CN, $NH_2$, $CH_2OH$ |
| $CH_3$ | OH | CN | $NH_2$, $NH-NH_2$, $NH-OH$, OH, SH | O, S | H, $CH_3$, F, Cl, Br, I, $NO_2$, $CH=CH_2$, $CH=CHBr$, $CH=CHCl$, $C≡CH$, CN, $NH_2$, $CH_2OH$ |
| $CH_3$ | OH | OMe | $NH_2$, $NH-NH_2$, $NH-OH$, OH, SH | O, S | H, $CH_3$, F, Cl, Br, I, $NO_2$, $CH=CH_2$, $CH=CHBr$, $CH=CHCl$, $C≡CH$, CN, $NH_2$, $CH_2OH$ |
| $CH_3$ | OH | F | $NH_2$, $NH-NH_2$, $NH-OH$, OH, SH | O, S | H, $CH_3$, F, Cl, Br, I, $NO_2$, $CH=CH_2$, $CH=CHBr$, $CH=CHCl$, $C≡CH$, CN, $NH_2$, $CH_2OH$ |
| $CH_3$ | OH | Me | $NH_2$, $NH-NH_2$, $NH-OH$, OH, SH | O, S | H, $CH_3$, F, Cl, Br, I, $NO_2$, $CH=CH_2$, $CH=CHBr$, $CH=CHCl$, $C≡CH$, CN, $NH_2$, $CH_2OH$ |
| $CH=CH_2$ | OH | $C≡CH$ | $NH_2$, $NH-NH_2$, $NH-OH$, OH, SH | O, S | H, $CH_3$, F, Cl, Br, I, $NO_2$, $CH=CH_2$, $CH=CHBr$, $CH=CHCl$, $C≡CH$, CN, $NH_2$, $CH_2OH$ |
| $CH=CH_2$ | OH | CN | $NH_2$, $NH-NH_2$, $NH-OH$, OH, SH | O, S | H, $CH_3$, F, Cl, Br, I, $NO_2$, $CH=CH_2$, $CH=CHBr$, $CH=CHCl$, $C≡CH$, CN, $NH_2$, $CH_2OH$ |
| $CH=CH_2$ | OH | F | $NH_2$, $NH-NH_2$, $NH-OH$, OH, SH | O, S | H, $CH_3$, F, Cl, Br, I, $NO_2$, $CH=CH_2$, $CH=CHBr$, $CH=CHCl$, $C≡CH$, CN, $NH_2$, $CH_2OH$ |
| $CH=CH_2$ | OH | Me | $NH_2$, $NH-NH_2$, $NH-OH$, OH, SH | O, S | H, $CH_3$, F, Cl, Br, I, $NO_2$, $CH=CH_2$, $CH=CHBr$, $CH=CHCl$, $C≡CH$, CN, $NH_2$, $CH_2OH$ |
| $CH=CH_2$ | OH | $N_3$ | $NH_2$, $NH-NH_2$, $NH-OH$, OH, SH | O, S | H, $CH_3$, F, Cl, Br, I, $NO_2$, $CH=CH_2$, $CH=CHBr$, $CH=CHCl$, $C≡CH$, CN, $NH_2$, $CH_2OH$ |
| $C≡CH$ | OH | $C≡CH$ | $NH_2$, $NH-NH_2$, $NH-OH$, OH, SH | O, S | H, $CH_3$, F, Cl, Br, I, $NO_2$, $CH=CH_2$, $CH=CHBr$, $CH=CHCl$, $C≡CH$, CN, $NH_2$, $CH_2OH$ |
| $C≡CH$ | OH | CN | $NH_2$, $NH-NH_2$, $NH-OH$, OH, SH | O, S | H, $CH_3$, F, Cl, Br, I, $NO_2$, $CH=CH_2$, $CH=CHBr$, $CH=CHCl$, $C≡CH$, CN, $NH_2$, $CH_2OH$ |
| $C≡CH$ | OH | $N_3$ | $NH_2$, $NH-NH_2$, $NH-OH$, OH, SH | O, S | H, $CH_3$, F, Cl, Br, I, $NO_2$, $CH=CH_2$, $CH=CHBr$, $CH=CHCl$, $C≡CH$, CN, $NH_2$, $CH_2OH$ |
| $C≡CH$ | OH | OMe | $NH_2$, $NH-NH_2$, $NH-OH$, OH, SH | O, S | H, $CH_3$, F, Cl, Br, I, $NO_2$, $CH=CH_2$, $CH=CHBr$, $CH=CHCl$, $C≡CH$, CN, $NH_2$, $CH_2OH$ |
| $CH_2F$ | OH | $C≡CH$ | $NH_2$, $NH-NH_2$, $NH-OH$, OH, SH | O, S | H, $CH_3$, F, Cl, Br, I, $NO_2$, $CH=CH_2$, $CH=CHBr$, $CH=CHCl$, $C≡CH$, CN, $NH_2$, $CH_2OH$ |
| $CH_2F$ | OH | CN | $NH_2$, $NH-NH_2$, $NH-OH$, OH, SH | O, S | H, $CH_3$, F, Cl, Br, I, $NO_2$, $CH=CH_2$, $CH=CHBr$, $CH=CHCl$, $C≡CH$, CN, $NH_2$, $CH_2OH$ |

TABLE I-continued

| $R^2$ | $R^3$ | $R^4$ | $R^5$ | X | $R^6$ |
|---|---|---|---|---|---|
| $CH_2F$ | OH | $N_3$ | $NH_2$, $NH-NH_2$, $NH-OH$, OH, SH | O, S | H, $CH_3$, F, Cl, Br, I, $NO_2$, $CH=CH_2$, $CH=CHBr$, $CH=CHCl$, $C\equiv CH$, CN, $NH_2$, $CH_2OH$ |
| $CH_2F$ | OH | $CH=CH_2$ | $NH_2$, $NH-NH_2$, $NH-OH$, OH, SH | O, S | H, $CH_3$, F, Cl, Br, I, $NO_2$, $CH=CH_2$, $CH=CHBr$, $CH=CHCl$, $C\equiv CH$, CN, $NH_2$, $CH_2OH$ |
| CN | OH | $C\equiv CH$ | $NH_2$, $NH-NH_2$, $NH-OH$, OH, SH | O, S | H, $CH_3$, F, Cl, Br, I, $NO_2$, $CH=CH_2$, $CH=CHBr$, $CH=CHCl$, $C\equiv CH$, CN, $NH_2$, $CH_2OH$ |
| CN | OH | CN | $NH_2$, $NH-NH_2$, $NH-OH$, OH, SH | O, S | H, $CH_3$, F, Cl, Br, I, $NO_2$, $CH=CH_2$, $CH=CHBr$, $CH=CHCl$, $C\equiv CH$, CN, $NH_2$, $CH_2OH$ |
| CN | OH | $N_3$ | $NH_2$, $NH-NH_2$, $NH-OH$, OH, SH | O, S | H, $CH_3$, F, Cl, Br, I, $NO_2$, $CH=CH_2$, $CH=CHBr$, $CH=CHCl$, $C\equiv CH$, CN, $NH_2$, $CH_2OH$ |
| CN | OH | $CH=CH_2$ | $NH_2$, $NH-NH_2$, $NH-OH$, OH, SH | O, S | H, $CH_3$, F, Cl, Br, I, $NO_2$, $CH=CH_2$, $CH=CHBr$, $CH=CHCl$, $C\equiv CH$, CN, $NH_2$, $CH_2OH$ |
| $CH_2CH_3$ | OH | $N_3$ | $NH_2$, $NH-NH_2$, $NH-OH$, OH, SH | O, S | H, $CH_3$, F, Cl, Br, I, $NO_2$, $CH=CH_2$, $CH=CHBr$, $CH=CHCl$, $C\equiv CH$, CN, $NH_2$, $CH_2OH$ |
| $CF_3$ | OH | $N_3$ | $NH_2$, $NH-NH_2$, $NH-OH$, OH, SH | O, S | H, $CH_3$, F, Cl, Br, I, $NO_2$, $CH=CH_2$, $CH=CHBr$, $CH=CHCl$, $C\equiv CH$, CN, $NH_2$, $CH_2OH$ |

In which a more preferred embodiment is one that has the following structure, but the same substituent pattern as noted in Table I.

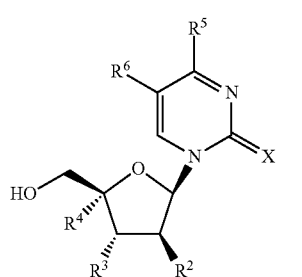

TABLE II

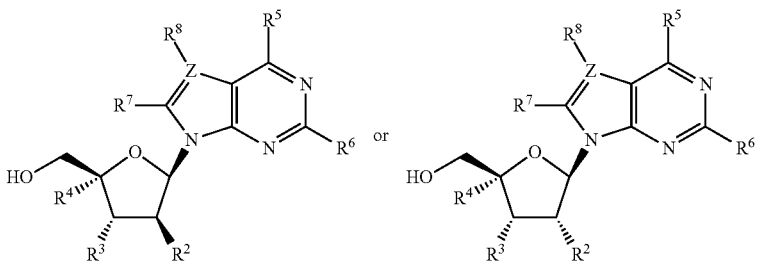

| R² | R³ | R⁴ | R⁶ | R⁵ | Z | R⁸ | R⁷ |
|---|---|---|---|---|---|---|---|
| CH₃ | OH | N₃ | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₃ | OH | N₃ | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CH₃ | OH | N₃ | NH₂ | NH₂, NH—Me, MH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₃ | OH | N₃ | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CH₃ | OH | C≡CH | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₃ | OH | C≡CH | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N-Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CH₃ | OH | C≡CH | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₃ | OH | C≡CH | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CH₃ | OH | CH=CH₂ | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₃ | OH | CH=CH₂ | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CH₃ | OH | CH=CH₂ | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₃ | OH | CH=CH₂ | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂ C≡CH, CN, COOH, CONH₂, COOMe | H |
| CH₃ | OH | CN | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₃ | OH | CN | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |

TABLE II-continued

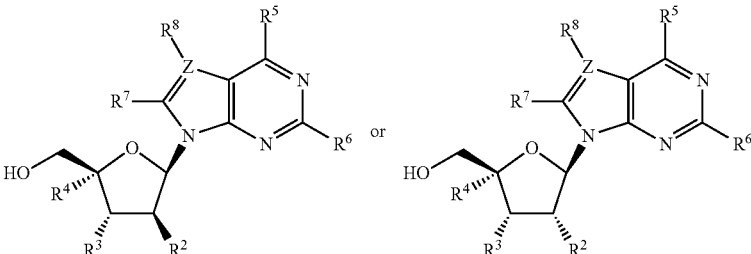

| R² | R³ | R⁴ | R⁶ | R⁵ | Z | R⁸ | R⁷ |
|---|---|---|---|---|---|---|---|
| CH₃ | OH | CN | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₃ | OH | CN | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂ C≡CH, CN, COOH, CONH₂, COOMe | H |
| CH₃ | OH | OMe | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₃ | OH | OMe | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂ C≡CH, CN, COOH, CONH₂, COOMe | H |
| CH₃ | OH | OMe | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₃ | OH | OMe | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂ C≡CH, CN, COOH, CONH₂, COOMe | H |
| CH₃ | OH | F | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₃ | OH | F | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂ C≡CH, CN, COOH, CONH₂, COOMe | H |
| CH₃ | OH | F | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₃ | OH | F | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂ C≡CH, CN, COOH, CONH₂, COOMe | H |
| CH₃ | OH | Me | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₃ | OH | Me | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂ C≡CH, CN, COOH, CONH₂, COOMe | H |
| CH₃ | OH | Me | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₃ | OH | Me | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂ C≡CH, CN, COOH, CONH₂, COOMe | H |

TABLE II-continued

| R² | R³ | R⁴ | R⁶ | R⁵ | Z | R⁸ | R⁷ |
|---|---|---|---|---|---|---|---|
| CH=CH₂ | OH | C≡CH | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH=CH₂ | OH | C≡CH | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂ C≡CH, CN, COOH, CONH₂, COOMe | H |
| CH=CH₂ | OH | C≡CH | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH=CH₂ | OH | C≡CH | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂ C≡CH, CN, COOH, CONH₂, COOMe | H |
| CH=CH₂ | OH | CN | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH=CH₂ | OH | CN | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂ C≡CH, CN, COOH, COOMe | H |
| CH=CH₂ | OH | CN | NH₂ | NH₂, NH—Me, NH—Et, NH-proopyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH=CH₂ | OH | CN | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂ C≡CH, CN, COOH, CONH₂, COOMe | H |
| CH=CH₂ | OH | F | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH=CH₂ | OH | F | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂ C≡CH, CN, COOH, CONH₂, COOMe | H |
| CH=CH₂ | OH | F | NH₂ | NH₂, NH—Me, NH—Et, NH-propyl, heterocycle, NH-cyclopropyl, NH-acetyl, NH-cyclobtuyl, NH-5-butyl, Azetidine, N,N—Me₂, N,N—Et₂, F, Cl, Br, I, OH, OMe, OEt, OBn, SH, SMe, SEt, O-acetyl | N | — | H |
| CH=CH₂ | OH | F | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂ C≡CH, CN, COOH, CONH₂, COOMe | H |
| CH=CH₂ | OH | Me | H | NH₂, NH—Me, NH—Et, NH-propyl, heterocycle, NH-cyclopropyl, NH-acetyl, NH-cyclojbtyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH=CH₂ | OH | Me | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |

TABLE II-continued

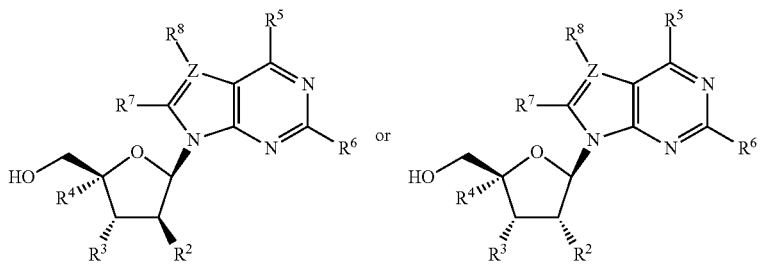

| R² | R³ | R⁴ | R⁶ | R⁵ | Z | R⁸ | R⁷ |
|---|---|---|---|---|---|---|---|
| CH=CH₂ | OH | Me | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH=CH₂ | OH | Me | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, CL, Br, I, NO₂, CH=CH₂, C≡CH, CN, COOH, CONH₂, COOMe | H |
| CH=CH₂ | OH | N₃ | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH=CH₂ | OH | N₃ | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CH=CH₂ | OH | N₃ | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH=CH₂ | OH | N₃ | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| C≡CH | OH | C≡CH | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| C≡CH | OH | C≡CH | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, CL, Br, I, NO₂, CH=CH₂, C≡CH, CN, COOH, CONH₂, COOMe | H |
| C≡CH | OH | C≡CH | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| C≡CH | OH | C≡CH | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| C≡CH | OH | CN | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| C≡CH | OH | CN | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| C≡CH | OH | CN | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| C≡CH | OH | CN | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |

TABLE II-continued

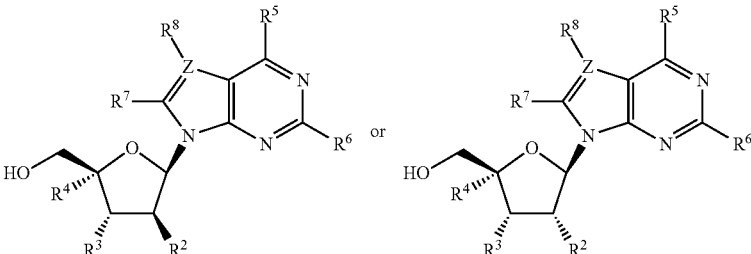

| R² | R³ | R⁴ | R⁶ | R⁵ | Z | R⁸ | R⁷ |
|---|---|---|---|---|---|---|---|
| C≡CH | OH | N₃ | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| C≡CH | OH | N₃ | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| C≡CH | OH | N₃ | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| C≡CH | OH | N₃ | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| C≡CH | OH | OMe | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| C≡CH | OH | OMe | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| C≡CH | OH | OMe | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| C≡CH | OH | OMe | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CH₂F | OH | C≡CH | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₂F | OH | C≡CH | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂ C≡CH, CN, COOH, CONH₂, COOMe | H |
| CH₂F | OH | C≡CH | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₂F | OH | C≡CH | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CH₂F | OH | CN | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₂F | OH | CN | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |

TABLE II-continued

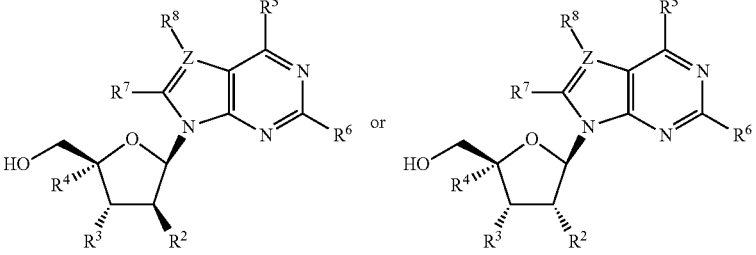

| R² | R³ | R⁴ | R⁶ | R⁵ | Z | R⁸ | R⁷ |
|---|---|---|---|---|---|---|---|
| $CH_2F$ | OH | CN | $NH_2$ | $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, F, Cl, Br, I, OH, OMe, OEt, OBn, SH, SMe, SEt, O-acetyl | N | — | H |
| $CH_2F$ | OH | CN | $NH_2$ | $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, F, Cl, Br, I, OH, OMe, OEt, OBn, SH, SMe, SEt, O-acetyl | C | H, F, Cl, Br, I, $NO_2$, $CH=CH_2$, $C\equiv CH$, CN, COOH, $CONH_2$, COOMe | H |
| $CH_2F$ | OH | $N_3$ | H | $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, F, Cl, Br, I, OH, OMe, OEt, OBn, SH, SMe, SEt, O-acetyl | N | — | H |
| $CH_2F$ | OH | $N_3$ | H | $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, F, Cl, Br, I, OH, OMe, OEt, OBn, SH, SMe, SEt, O-acetyl | C | H, F, Cl, Br, I, $NO_2$, $CH=CH_2$, $C\equiv CH$, CN, COOH, $CONH_2$, COOMe | H |
| $CH_2F$ | OH | $N_3$ | $NH_2$ | $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, F, Cl, Br, I, OH, OMe, OEt, OBn, SH, SMe, SEt, O-acetyl | N | — | H |
| $CH_2F$ | OH | $N_3$ | $NH_2$ | $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, F, Cl, Br, I, OH, OMe, OEt, OBn, SH, SMe, SEt, O-acetyl | C | H, F, Cl, Br, I, $NO_2$, $CH=CH_2$, $C\equiv CH$, CN, COOH, $CONH_2$, COOMe | H |
| $CH_2F$ | OH | $CH=CH_2$ | H | $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, F, Cl, Br, I, OH, OMe, OEt, OBn, SH, SMe, SEt, O-acetyl | N | — | H |
| $CH_2F$ | OH | $CH=CH_2$ | H | $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, F, Cl, Br, I, OH, OMe, OEt, OBn, SH, SMe, SEt, O-acetyl | C | H, F, Cl, Br, I, $NO_2$, $CH=CH_2$, $C\equiv CH$, CN, COOH, $CONH_2$, COOMe | H |
| $CH_2F$ | OH | $CH=CH_2$ | $NH_2$ | $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, F, Cl, Br, I, OH, OMe, OEt, OBn, SH, SMe, SEt, O-acetyl | N | — | H |
| $CH_2F$ | OH | $CH=CH_2$ | $NH_2$ | $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, F, Cl, Br, I, OH, OMe, OEt, OBn, SH, SMe, SEt, O-acetyl | C | H, F, Cl, Br, I, $NO_2$, $CH=CH_2$, $C\equiv CH$, CN, COOH, $CONH_2$, COOMe | H |
| CN | OH | $C\equiv CH$ | H | $NH_2$, NH—Me, NH—Et, NH-propyl, heterocycle, NH-cyclobutyl, NH-t-butyl, Azetidine, N,N—$Me_2$, N,N—$Et_2$, F, Cl, Br, I, OH, OMe, OEt, OBn, SH, SMe, SEt, O-acetyl | N | — | H |
| CN | OH | $C\equiv CH$ | H | $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, F, Cl, Br, I, OH, OMe, OEt, OBn, SH, SMe, SEt, O-acetyl | C | H, F, Cl, Br, I, $NO_2$, $CH=CH_2$, $C\equiv CH$, CN, COOH, $CONH_2$, COOMe | H |
| CN | OH | $C\equiv CH$ | $NH_2$ | $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, F, Cl, Br, I, OH, OMe, OEt, OBn, SH, SMe, SEt, O-acetyl | N | — | H |
| CN | OH | $C\equiv CH$ | $NH_2$ | $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, F, Cl, Br, I, OH, OMe, OEt, OBn, SH, SMe, SEt, O-acetyl | C | H, F, Cl, Br, I, $NO_2$, $CH=CH_2$, $C\equiv CH$, CN, COOH, $CONH_2$, COOMe | H |

TABLE II-continued

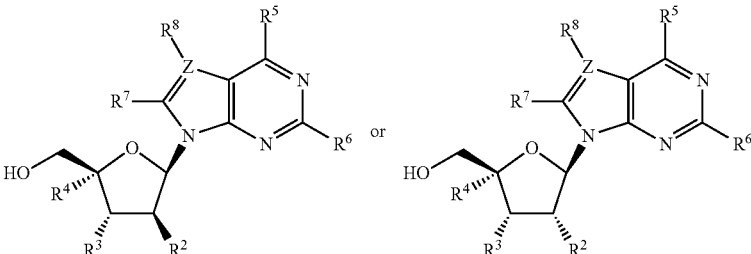

| R² | R³ | R⁴ | R⁶ | R⁵ | Z | R⁸ | R⁷ |
|---|---|---|---|---|---|---|---|
| CN | OH | CN | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CN | OH | CN | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CN | OH | CN | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CN | OH | CN | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CN | OH | N₃ | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CN | OH | N₃ | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CN | OH | N₃ | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, Oet, OBn, SH, SMe, SEt, O-acetyl | N | — | H |
| CN | OH | N₃ | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CN | OH | CH=CH₂ | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CN | OH | CH=CH₂ | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CN | OH | CH=CH₂ | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CN | OH | CH=CH₂ | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CH₂CH₃ | OH | N₃ | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₂CH₃ | OH | N₃ | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |

TABLE II-continued

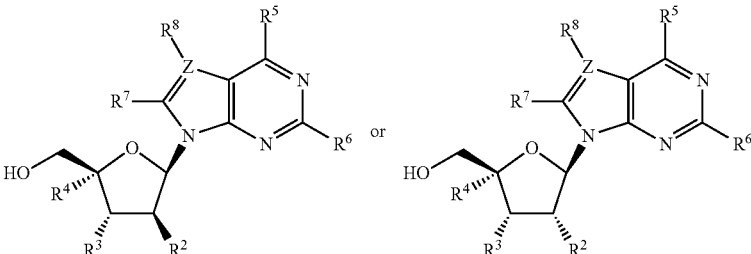

| R² | R³ | R⁴ | R⁶ | R⁵ | Z | R⁸ | R⁷ |
|---|---|---|---|---|---|---|---|
| CH₂CH₃ | OH | N₃ | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₂CH₃ | OH | N₃ | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CF₃ | OH | N₃ | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CF₃ | OH | N₃ | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CF₃ | OH | N₃ | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CF₃ | OH | N₃ | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |

In which a more preferred embodiment is one that has the following structure, but the same substituent pattern as noted in Table II.

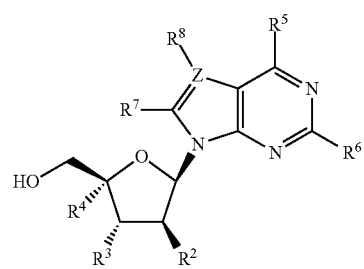

DEFINITIONS

The phrase "a" or "an" entity as used herein refers to one or more of that entity; for example, a compound refers to one or more compounds or at least one compound. As such, the terms "a" or (or "an"), "one or more", and "at least one" can be used interchangeably herein.

The phrase "as defined herein above" refers to the first definition provided in the Summary of the Invention.

The terms "optional" or "optionally" as used herein means that a subsequently described event or circumstance may but need not occur, and that the description includes instances where the event or circumstance occurs and instances in which it does not. For example, "optional bond" means that the bond may or may not be present, and that the description includes single, double, or triple bonds.

The term "independently" is used herein to indicate that a variable is applied in any one instance without regard to the presence or absence of a variable having that same or a different definition within the same compound. Thus, in a compound in which R appears twice and is defined as "independently carbon or nitrogen", both R's can be carbon, both R's can be nitrogen, or one R can be carbon and the other nitrogen.

The term "alkenyl" refers to an unsubstituted hydrocarbon chain radical having from 2 to 10 carbon atoms having one or two olefinic double bonds, preferably one olefinic double bond. The term "$C_{2-N}$ alkenyl" refers to an alkenyl comprising 2 to N carbon atoms where N is an integer having the following values: 3, 4, 5, 6, 7, 8, 9, or 10. The term "$C_{2-10}$ alkenyl" refers to an alkenyl comprising 2 to 10 carbon atoms. Examples include, but are not limited to, vinyl, 1-propenyl, 2-propenyl, (allyl) or 2-butenyl (crotyl).

The term "halogenated alkenyl" refers to an alkenyl comprising at least one of F, Cl, Br, and I.

The term "alkyl" refers to an unbranched or branched chain, saturated, monovalent hydrocarbon residue containing 1 to 30 carbon atoms. The term "$C_{1-N}$ alkyl" refers to an alkyl comprising 1 to N carbon atoms, where N is an integer having the following values: 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30. The term "$C_{1-4}$" alkyl refers to an alkyl contain 1 to 4 carbon atoms. The term "low alkyl" or "lower alkyl" denotes a straight or branched chain hydrocarbon residue comprising 1 to 8 carbon atoms. "$C_{1-20}$ alkyl" as used herein refers to an alkyl comprising 1 to 20 carbon atoms. "$C_{1-10}$ alkyl" as used herein refers to an alkyl comprising 1 to 10 carbon atoms. Examples of alkyl groups include, but are not limited to, methyl, ethyl, propyl, i-propyl, n-butyl, i-butyl, t-butyl, pentyl, isopentyl, neopentyl, hexyl, heptyl, and octyl. The term (ar)alkyl or (heteroaryl)alkyl indicate the alkyl group is optionally substituted by an aryl or a heteroaryl group respectively.

The term "halogenated alkyl" (or "haloalkyl") refers to an unbranched or branched chain alkyl comprising at least one of F, Cl, Br, and I. The term "$C_{1-3}$ haloalkyl" refers to a haloalkyl comprising 1 to 3 carbons and at least one of F, Cl, Br, and I. The term "halogenated lower alkyl" refers to a haloalkyl comprising 1 to 8 carbon atoms and at least one of F, Cl, Br, and I. Examples include, but are not limited to, fluoromethyl, chloromethyl, bromomethyl, iodomethyl, difluoromethyl, dichloromethyl, dibromomethyl, diiodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chhoroethyl, 2-bromoethyl, 2-iodoethyl, 2,2-difluoroethyl, 2,2-dichloroethyl, 2,2-dibromoethyl, 2,2-diiodoethyl, 3-fluoropropyl, 3-chloropropyl, 3-bromopropyl, 3-iodopropyl, 2,2,2-trifluoroethyl, 1,1,2,2, 2-pentafluoroethyl, 1-fluoro-1-chloroethyl, or 1-fluroro-1-chloro-1-bromoethyl.

The term "alkynyl" refers to an unbranched or branched hydrocarbon chain radical having from 2 to 10 carbon atoms, preferably 2 to 5 carbon atoms, and having one triple bond. The term "$C_{2-N}$ alkynyl" refers to an alkynyl comprising 2 to N carbon atoms, where N is an integer having the following values: 2, 3, 4, 5, 6, 7, 8, 9, or 10. The term "$C_{2-4}$ alkynyl" refers to an alkynyl comprising 2 to 4 carbon atoms. The term "$C_{2-10}$ alkynyl" refers to an alkynyl comprising 2 to 10 carbon atoms. Examples include, but are not limited to, ethynyl, 1-propynyl, 2-propynyl, 1-butynyl, 2-butynyl, or 3-butynyl.

The term "halogenated alkynyl" refers to an unbranched or branched hydrocarbon chain radical having from 2 to 10 carbon atoms preferably 2 to 5 carbon atoms, and having one triple bond and at least one of F, Cl, Br, and I.

The term "cycloalkyl" refers to a saturated carbocyclic ring comprising 3 to 8 carbon atoms, i.e. cyclopropyl, cyclobutyl, cyclopentyl, cyclohexyl, cycloheptyl or cyclooctyl. The term "$C_{3-7}$ cycloalkyl" as used herein refers to a cycloalkyl comprising 3 to 7 carbons in the carbocyclic ring.

The term "alkoxy" refers to an —O-alkyl group, wherein alkyl is defined above. Examples include, but are not limited to, methoxy, ethoxy, n-propyloxy, i-propyloxy, n-butyloxy, i-butyloxy, t-butyloxy. "Lower alkoxy" or "low alkoxy" or "low alkoxyl" as used herein denotes an alkoxy group with a "lower alkyl" group as previously defined. "$C_{1-10}$ alkoxy" refers to an —O-alkyl wherein alkyl is $C_{1-10}$.

The term "halogenated alkoxy" refers to an —O-alkyl group in which the alkyl group comprises at least one of F, Cl, Br, and I.

The term "halogenated lower alkoxy" or "halogenated low alkoxy" refers to an —O-(lower alkyl) group in which the lower alkyl group comprises at least one of F, Cl, Br, and I.

The term "substituted", as used herein, means that one or more hydrogens on the designated atom is replaced with a selection from the indicated group, provided that the designated atom's normal valency is not exceeded, and that the substitution results in a stable compound.

The term "protected", as used herein and unless otherwise defined, refers to a group that is added to an oxygen, nitrogen, or phosphorus atom to prevent its further reaction or for other purposes. A wide variety of oxygen and nitrogen protecting groups are known to those skilled in the art of organic synthesis. Non-limiting examples include: C(O)-alkyl, C(O)Ph, C(O)aryl, $CH_3$, $CH_2$-alkyl, $CH_2$-alkenyl, $CH_2$Ph, $CH_2$-aryl, $CH_2$O-alkyl, $CH_2$O-aryl, $SO_2$-alkyl, $SO_2$-aryl, tert-butyldimethylsilyl, tert-butyldiphenylsilyl, and 1,3-(1,1,3,3-tetraisopropyldisiloxanylidene).

The term "halo" as used herein includes fluoro, chloro, bromo, and iodo.

The term "purine" or "pyrimidine" base includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinyulpurine, $N^6$-acetylenic purine, $N^6$-acyl purine, N6-hydroxyalkylpurine, $N^6$-allylaminopurine, $N^6$-thioallcyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and 4-mercaptopyrimidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-aminopyrimidine, $C^5$-cyanopyrimidine, $C^5$-iodopyrimidine, $C^6$-iodo-pyrimidine, $C^5$—Br-vinyl pyrimidine, $C^6$—Br-vinyl pyrimidine, $C^5$-nitropyrimidine, $C^5$-amino-pyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adeninne, hypoxanthine, 2,6-diaminopurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methansulfonyl, and p-toluenesulfonyl.

The term "tautomerism" and "tautomers" have their accepted meanings.

The term "pharmaceutically acceptable salt or prodrug" is used throughout the specification to describe any pharmaceutically acceptable form (such as an ester, phosphate ester, salt of an ester or related group) of a compound which upon administration to a mammal, provides the active compound. Pharmaceutically acceptable salts include those derived from pharmaceutically acceptable inorganic or organic bases and acids. Pharmaceutically acceptable prodrugs refer to a compound that is metabolized, for example hydrolyzed or oxidized, in the host to form a compound of the present invention. Typical examples of prodrugs include compounds that have biologically labile protecting groups on a functional moiety of the selected compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. The compounds of this invention possess antiviral activity against the HIV, HBV and HCV viruses, or are metabolized to a compound that exhibits such activity.

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including sulfate, nitrate, bicarbonate and carbonate salts.

Alternatively, pharmaceutically acceptable salts may be obtained, for example, by reacting a sufficiently basic compound such as an amine with a suitable acid affording a physiologically acceptable anion. Alkali metal (for example, sodium, potassium, or lithium) or alkaline earth metal (for example, calcium and magnesium) salts of, for example, carboxylic acids can also be made.

Any of the compounds described herein can be administered as a prodrug to increase the activity, bioavailability, stability or otherwise alter the properties of the selected compound. A number of prodrug ligands are known.

The term "host" as used herein, refers to a unicellular or multicellular organism in which the virus can replicate, including but not limited to cell lines and animals, and preferably a human. Alternatively, the host can be carrying a part of the viral genome, whose replication or function can be altered by the compounds of the present invention. The term host specifically refers to infected cells, cells transfected with all or part of the viral genome and animals.

The compounds of the present invention may be formulated in a wide variety of oral administration dosage forms and carriers. Oral administration can be in the form of tablets, coated tablets, hard and soft gelatin capsules, solutions, emulsions, syrups, or suspensions. Compounds of the present invention are efficacious when administered by suppository administration, among other routes of administration. The most convenient manner of administration is generally oral using a convenient daily dosing regimen which can be adjusted according to the severity of the disease and the patient's response to the antiviral medication.

A compound or compounds of the present invention, as well as their pharmaceutically acceptable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations or liquids such as suspensions, emulsions, or filled capsules for oral use; or in the form of suppositories for rectal or vaginal administration. A typical preparation will contain from about 5% to about 95% active compound or compounds (w/w). The term "preparation or "dosage form" is intended to include both solid and liquid formulations of the active compound and one skilled in the art will appreciate that an active ingredient can exist in different preparations depending on the desired dose and pharmacokinetic parameters.

The term "excipient" as used herein refers to a compound that is used to prepare a pharmaceutical composition, and is generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

A "pharmaceutically acceptable salt" form of an active ingredient may also initially confer a desirable pharmacokinetic property on the active ingredient which was absent in the non-salt form, and may even positively affect the pharmacodynamics of the active ingredient with respect to its therapeutic activity in the body. The phrase "pharmaceutically acceptable salt" of a compound as used herein means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as glycolic acid, pyruvic acid, lactic acid, malonic acid, maleic acid, fumaric acid, tartaric acid, citric acid, 3-(4-hydroxybenzoyl)benzoic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, lauryl sulfuric acid, gluconic acid, glutamic acid, salicyclic acid, muconic acid, and the like or (2) basic addition salts formed with the conjugate bases of any of the inorganic acids listed above, wherein the conjugate bases comprise a cationic component selected from among $Na^+$, $K^+$, $Mg^{+2}$, $Ca^{+2}$, $NHgR'''4\text{-}g+$, in which $R'''$ is a $C_{1-3}$ alkyl and g is a number selected from among 0, 1, 2, 3, or 4. It should be understood that all references to pharmaceutically acceptable salts include solvent addition forms (solvates), water addition forms (hydrates), or crystal forms (polymorphs) as defined herein, of the same acid additions salts.

Solid form preparations include powders, tablets, pills capsules, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component colorants, flavors, stabilizers, buffers, artificial and natural sweeteners, dispersants, thickeners, solubilizing agents, and the like.

Liquid formulations also are suitable for oral administration include liquid formulations including emulsions, syrups, elixirs and aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool and to solidify.

The compounds of the present invention may be formulated for vaginal administration. Pessaries, tampons, creams, gels, pastes, foams or sprays containing in addition to the active ingredient such carriers as are known in the art to be appropriate.

Suitable formulations along with pharmaceutical carriers, diluents and excipients are described in Remington: The Science and Practice of Pharmacy 1995, edited by E. W. Martin, Mack Publishing Company, 19th Edition, Easton, Pa., which is hereby incorporated by reference. A skilled formulation scientist may modify the formulations within the teachings of the specification to provide numerous formulations for a particular route of administration without rendering the compositions of the present invention unstable or comprising their therapeutic activity.

The modification of the present compounds to render them more soluble in water or other vehicle, for example, may be easily accomplished by minor modifications (e.g., salt formulation), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "medicament" means a substance used in a method of treatment and/or prophylaxis of a subject in need thereof, wherein the substance includes, but is not limited to, a composition, a formulation, a dosage from, and the like, comprising a compound of formula I. It is contemplated that the use of the compound represented by formula I in the manufacture of a medicament for the treatment of any of the antiviral conditions disclosed herein can be any of the compounds contemplated in any of the aspects of the invention, either alone or in combination with other compounds of the present invention.

The term "subject" means a mammal, which includes, but is not limited to, cattle, pigs, sheep, chicken, turkey, buffalo, llama, ostrich, dogs, cats, and humans, preferably the subject is a human.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.1 and about 10 g, including all values in between, such as 0.25, 0.5, 0.75, 1, 1.5, 2, 2.5, 3, 3.5, 4, 4.5, 5, 5.5, 6, 6.5, 7, 7.5, 8, 8.5, 9, and 9.5 g, per day should be appropriate in monotherapy and/or in combination therapy. A preferred daily dosage is between about 0.5 and about 7.5 g per day, a more preferred dosage is between 1.5 and about 6.0 g per day. Generally, treatment is initiated with a large initial "loading dose" to rapidly reduce or eliminate the virus followed by a decreasing of the dose to a level sufficient to prevent resurgence of the infection. One of ordinary skill in treating diseases described herein will be able, without undue experimentation and in reliance on personal knowledge, experience, and the disclosures of this application, to ascertain a therapeutically effective amount of the compounds of the present invention for a given disease and patient.

Therapeutic efficacy in HBV and HCV treatment can be ascertained from tests of liver function including, but not limited to protein levels such as serum proteins (e.g., albumin, clotting factors, alkaline phosphatase, aminotransferases (e.g., alanine transaminase, aspartate transaminase), 5'-nucleosidase, C-glutaminyltranspeptidase, etc.), synthesis of bilirubin, synthesis of cholesterol, and synthesis of bile acids; a liver metabolic function, including, but not limited to, carbohydrate metabolism, amino acid and ammonia metabolism. Alternatively the therapeutic effectiveness may be monitored by measuring HBV or HCV-RNA the results of these tests will allow the dose to be optimized. For HIV, therapeutic efficacy in HIV infection can be ascertained by measuring HIV-RNA levels from plasma samples and measuring levels of CD4 cells.

The disclosed compounds or their pharmaceutically acceptable derivatives or salts or pharmaceutically acceptable formulations containing these compounds are useful in the prevention and treatment of HIV infections and other related conditions such as AIDS-related complex (ARC), persistent generalized lymphadenopathy (PGL), AIDS-related neurological conditions, anti-HIV antibody positive and HIV-positive conditions, Kaposi's sarcoma, thrombocytopenia purpurea and opportunistic infections. In addition, these compounds or formulations can be used prophylactically to prevent or retard the progression of clinical illness in individuals who are anti-HIV antibody or HIV-antigen positive or who have been exposed to HIV.

Another aspect of the present invention comprises administering a therapeutically effective amount of a compound represented by formula I and a therapeutically effective amount of another antiviral agent; wherein the administration is concurrent or alternative or sequential. It is understood that the time between alternative (or sequential) administration can range between 1-24 hours, which includes any sub-range in between including 2, 3, 4, 5, 6, 7, 8, 9, 10, 11, 12, 13, 14, 15, 16, 17, 18, 19, 20, 21, 22, and 23 hours.

It is contemplated that the another antiviral agent includes but is not limited to interferon-α, interferon-B, pegylated interferon-α, ribavirin, levovirin, viramidine, another nucleoside HIV, HBV, or HCV polymerase inhibitor, an HIV, HBV, or HCV non-nucleoside polymerase inhibitor, an HIV, HBV, or HCV protease inhibitor, an HIV, HBV, or HCV helicase inhibitor or an HIV, HBV, or HCV fusion inhibitor. When an active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

In another embodiment for the treatment of HIV infection, the active compound or its prodrug or pharmaceutically acceptable salt can be administered in combination or alternation with another antiviral agent, such as another active anti-HIV agent, including but not limited to those of the formulae above, others listed below or known in the art. In general, in combination therapy, effective dosages of two or more agents are administered together, whereas during alternation therapy, an effective dosage of each agent is administered serially. The dosage will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Nonlimiting examples of antiviral agents that can be used in combination with the compounds disclosed herein include the following: Invirase®, Fortovase®, Norvir®, Crixivan®, Viracept®, Agenerase®, Kaletra®, Retrovir®, Epivir®, Combivir®, Triazivir®, Ziagen®, Hivid®, Videx®, Didex® EC, Zerit®, Viread®, Covincil™, Viramune®, Rescriptor®, Sustiva®, Droxia®, Fuzeon®, Atazanavir®, Proleukin®, Remune®, Procrit®, Darunavir®, and Serostim®.

Experimental Results

It will be understood that references herein to treatment extend to prophylaxis as well as to the treatment of existing conditions. Furthermore, the term "treatment" of a viral infection, as used herein, also includes treatment or prophylaxis of a disease or a condition associated with or mediated by the viral infection, or the clinical symptoms thereof.

Another embodiment is directed to a process for preparing the compound represented by A or A', to the compound A or A' obtained by the process, and to a composition comprising A or A' obtained by the process, the process comprising (1) deoxygenating the 2'-C-position of a compound represented by 1 or 1'

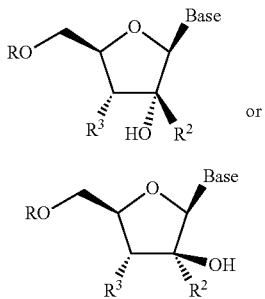

to obtain a compound represented by 2 or 2'

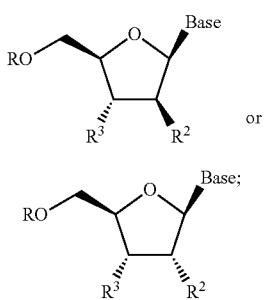

and (2) derivatizing the compound represented by 2 or 2' to obtain a compound represented by A or A'

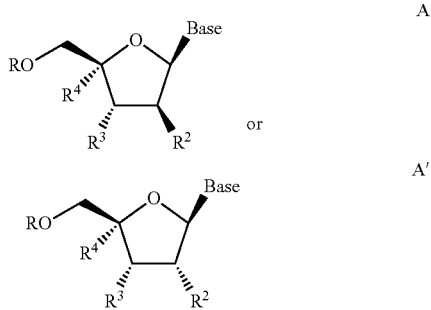

wherein for structures 1, 1', 2, 2', A, and A'

(a) $R^2$ is independently $CH_3$, $CH_2F$, $CHF_2$, $CF_3$, F, CN, $C_{2-4}$ alkenyl, $C_{2-4}$ alkynyl, or $C_{1-4}$ alkyl optionally substituted with amino, hydroxy, or 1 to 3 fluorine atoms;

(b) R is H, phosphate, including 5'-monophosphate, 5',3'-cyclic phosphate, diphosphate, triphosphate, or a stabilized phosphate prodrug, H-phosphonate, including stabilized H-phosphonates, acyl, including optionally substituted phenyl and lower acyl, alkyl, including lower alkyl, O-substituted carboxyalkylamino or its peptide derivatives, sulfonate ester, including alkyl or arylalkyl sulfonyl, including methanesulfonyl and benzyl, wherein the phenyl group is optionally substituted, a lipid, including a phospholipid, an L or D-amino acid, a carbohydrate, a peptide, a cholesterol, or other pharmaceutically acceptable leaving group which when administered in vivo;

(c) $R^3$ is independently OH, H, $C_{1-4}$ alkyl, $C_{2-4}$ alkenyl, $C_{2-4}$ alkynyl, vinyl, $N_3$, CN, Cl, Br, F, I, $NO_2$, $C(O)O(C_{1-4}$ alkyl), $C(O)O(C_{1-4}$ alkyl), $C(O)O(C_{2-4}$ alkynyl), $C(O)O(C_{2-4}$ alkenyl), $O(C_{1-10}$ acyl), $O(C_{1-4}$ alkyl), $O(C_{2-4}$ alkenyl), SH, $S(C_{1-4}$ acyl), $S(C_{1-4}$ alkyl), $S(C_{2-4}$ alkynyl), $S(C_{2-4}$ alkenyl), $SO(C_{1-4}$ acyl), $SO(C_{1-4}$ alkyl), $SO(C_{2-4}$ alkynyl), $SO(C_{2-4}$ alkenyl), $SO_2(C_{1-4}$ acyl), $SO_2(C_{1-4}$ alkyl), $SO_2(C_{2-4}$ alkynyl), $SO_2(C_{2-4}$ alkenyl), $OS(O)_2(C_{1-4}$ acyl), $OS(O)_2(C_{1-4}$ alkyl), $OS(O)_2(C_{2-4}$ alkenyl), $NH_2$, $NH(C_{1-4}$ alkyl), $NH(C_{2-4}$ alkenyl), $NH(C_{2-4}$ alkynyl), $NH(C_{1-4}$ acyl), $N(C_{1-4}$ alkyl)$_2$, $N(C_{1-18}$ acyl)$_2$, wherein alkyl, alkynyl, alkenyl and vinyl are optionally substituted by $N_3$, CN, one to three halogen (Cl, Br, F, I), $NO_2$, $C(O)O(C_{1-4}$ alkyl), $C(O)O(C_{1-4}$ alkyl), $C(O)O(C_{2-4}$ alkynyl), $C(O)O(C_{2-4}$ alkenyl), $O(C_{1-4}$ acyl), $O(C_{1-4}$ alkyl), $O(C_{2-4}$ alkenyl), SH, $S(C_{1-4}$ acyl), $S(C_{1-4}$ alkyl), $S(C_{2-4}$ alkynyl), $S(C_{2-4}$ alkenyl), $SO(C_{1-4}$ acyl), $SO(C_{1-4}$ alkyl), $SO(C_{2-4}$ alkynyl), $SO(C_{2-4}$ alkenyl), $SO_2(C_{1-4}$ acyl), $SO_2(C_{1-4}$ alkyl), $SO_2(C_{2-4}$ alkynyl), $SO_2(C_{2-4}$ alkenyl), $OS(O)_2(C_{1-4}$ acyl), $OS(O)_2(C_{1-4}$ alkyl), $OS(O)_2(C_{2-4}$ alkenyl), $NH_2$, $NH(C_{1-4}$ alkyl), $NH(C_{2-4}$ alkenyl), $NH(C_{2-4}$ alkynyl), $NH(C_{1-4}$ acyl), $N(C_{1-4}$ alkyl)$_2$, $N(C_{1-4}$ acyl)$_2$;

(d) $R^4$ is independently H, a lower alkyl, CN, vinyl, O-(lower alkyl), hydroxyl lower alkyl, i.e., —$(CH_2)_pOH$, where p is 1-6, including hydroxyl methyl ($CH_2OH$), $CH_2F$, $N_3$, $CH_2CN$, $CH_2NH_2$, $CH_2NHCH_3$, $CH_2N(CH_3)_2$, ethynyl alkyne (optionally substituted), or halogen, including F, Cl, Br, or I, alkenyl, alkynyl, Br-vinyl, hydroxy, O-alkenyl, $NO_2$, amino, loweralkylamino, or di(loweralkyl)amino;

(e) R and R3 can together form 5',3'-cyclic phosphate including stabilized prodrugs thereof;

(f) Base is a naturally occurring or modified purine or pyrimidine base represented by the following structures:

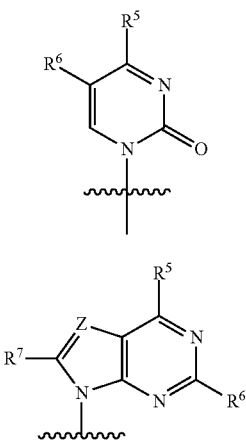

a b wherein for a and b

Z is N or $CR^8$;

$R^5$, $R^6$, and $R^7$ are independently H, F, Cl, Br, I, OH, OR', SH, SR', $NH_2$, NHR', $NR'_2$ (two R' can form saturated or unsaturated rings, or saturated or unsaturated heterocyclic rings), lower alkyl of $C_1$-$C_6$, halogenated (F, Cl, Br, I) lower alkyl of $C_1$-$C_6$, lower alkenyl of $C_2$-$C_6$, halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$ wherein R' is an optionally substituted alkyl, which includes, but is not limited to, an optionally substituted $C_{1-20}$ alkyl, an optionally substituted $C_{1-10}$ alkyl, an optionally substituted lower alkyl; an optionally substituted cycloalkyl; an optionally substituted alkynyl of $C_2$-$C_6$, an optionally substituted lower alkenyl of $C_2$-$C_6$, or optionally substituted acyl, which includes but is not limited to C(O) alkyl, C(O)($C_{1-20}$ alkyl), C(O)($C_{1-10}$ alkyl), or C(O)(lower alkyl), optionally substituted aryl, optionally substituted $C_1$-$C_4$ alkylaryloxy, heteroaryl, optionally substituted $C_1$-$C_4$ alkyl-heteroaryl, an optionally substituted alkoxy $C_{1-20}$ alkyl, an optionally substituted amino $C_{1-20}$ alkyl, an optionally substituted fluoro $C_{1-20}$ alkyl;

$R^8$ is independently H, halogen (including F, Cl, Br, I), OH, OR', SH, SR', $NH_2$, NHR', $NR'_2$ (two R' can form saturated or unsaturated rings, or saturated or unsaturated heterocyclic rings), $NO_2$, lower alkyl of $C_1$-$C_6$, halogenated (F, Cl, Br, I) lower alkyl of $C_1$-$C_6$, lower alkenyl of $C_2$-$C_6$, halogenated (F, Cl, Br, I) lower alkenyl of $C_2$-$C_6$, lower alkynyl of $C_2$-$C_6$, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$, wherein R' is an optionally substituted alkyl, which includes, but is not limited to, an optionally substituted $C_{1-20}$ alkyl, an optionally substituted $C_{1-10}$ alkyl, an optionally substituted lower alkyl; an optionally substituted cycloalkyl; an optionally substituted alkynyl of $C_2$-$C_6$, an optionally substituted lower alkenyl of $C_2$-$C_6$, or optionally substituted acyl, which includes but is not limited to C(O) alkyl, C(O)($C_{1-20}$ alkyl), C(O)($C_{1-10}$ alkyl), or C(O)(lower alkyl), optionally substituted aryl, optionally substituted $C_1$-$C_4$ alkyl-aryloxy, heteroaryl, optionally substituted $C_1$-$C_4$ alkyl-heteroaryl, an optionally substituted alkoxy $C_{1-20}$ alkyl, an optionally substituted amino $C_{1-20}$ alkyl, an optionally substituted fluoro $C_{1-20}$ alkyl; or base may be selected from a group of formula c

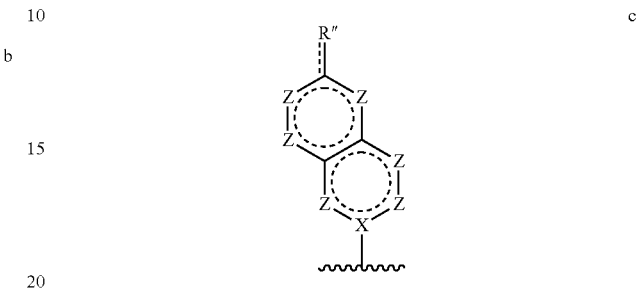

c wherein for structure c, if Z is a participant in a pi bond (double bond), Z is independently selected from N or C-G; or, if Z is not a participant in a pi bond (double bond), Z is independently selected from O, S, Se, NR, NOR, $NNR_2$, CO, CS, CNR, SO, $S(O)_2$, SeO, $Se(O)_2$, or $C(G)_2$;

each G is independently selected from the group consisting of H, halogen, OR, SR, $NR_2$, NROR, $N_3$, COOR, CN, $CONR_2$, $C(S)NR_2$, C(=NR)$NR_2$, and R; and where any two adjacent Z are not both selected from O, S, and Se, or not both selected from CO, CS, CNNR, SO, $S(O)_2$, SeO and $Se(O)_2$;

wherein, if X is a participant in a pi bond (double bond), X is C; or if X is not a participant in a pi bond (double bond), X is CR or N;

wherein, if R" is a participant in a pi bond (double bond), R" is O, S, Se, NR, NOR or $NNR_2$; or if R" is not a participant in a pi bond (double bond), R" is OR, SR, F, Cl, R, or SeR; and dashed lines (---) indicate a possible pi or double bond;

each R is independently selected from the group consisting of H, $CF_3$, optionally substituted alkyl, optionally substituted alkenyl, optionally substituted alkynyl, optionally substituted aryl, optionally substituted acyl, optionally substituted cycloalkyl, optionally substituted cycloalkenyl, optionally substituted heteroaryl, optionally substituted heterocyclyl, and optionally substituted arylalkyl; or base may be a structure selected from the group consisting of structures d-n

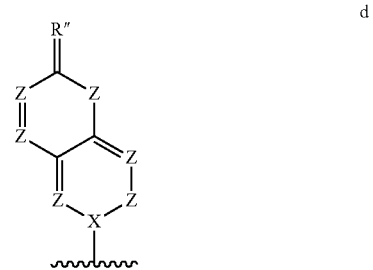

d

-continued
e
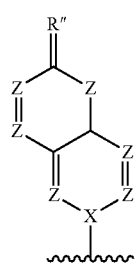
f
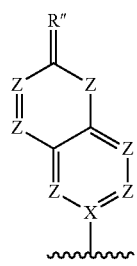
g
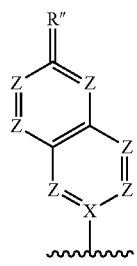
h
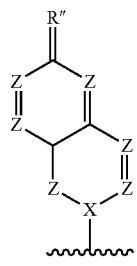
i
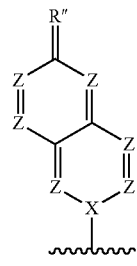
j
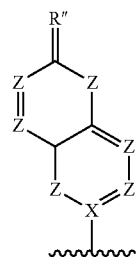
-continued
k
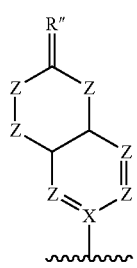
l
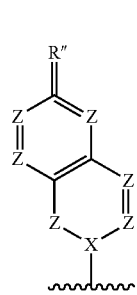
m
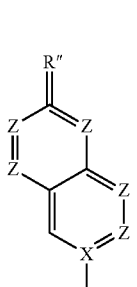
n
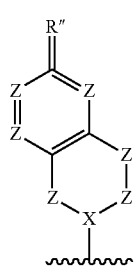
wherein Z, X, and R″ are defined as in structure c;
base may be a structure selected from the group consisting of structures o-ff
o
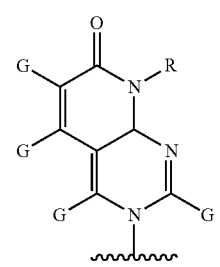

-continued
p
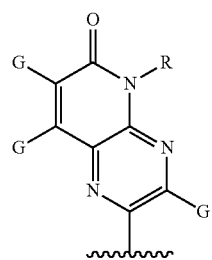
q
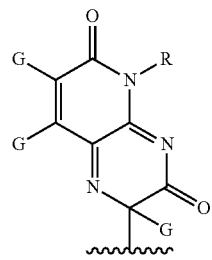
r
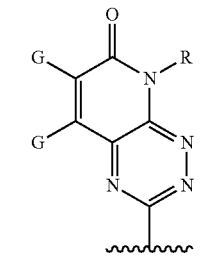
s
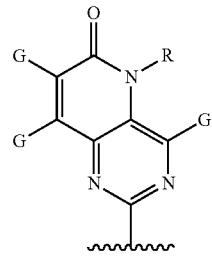
t
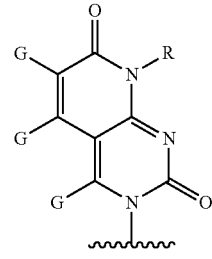
u
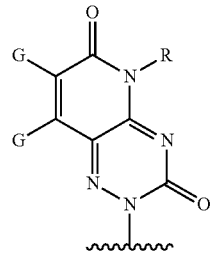
-continued
v
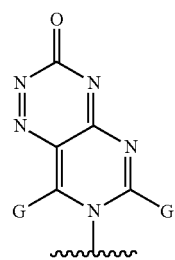
w
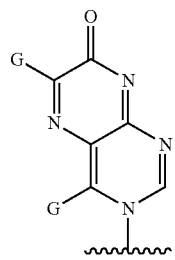
x
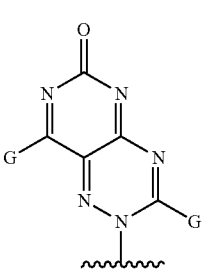
y
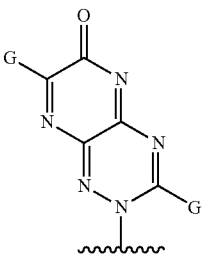
z
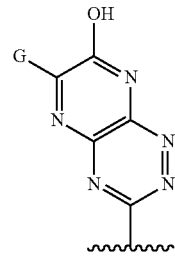
aa
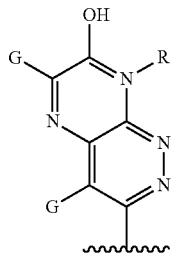

-continued bb
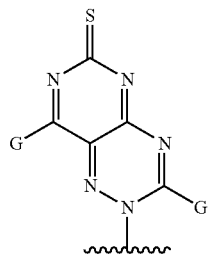

cc
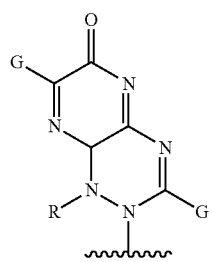

dd
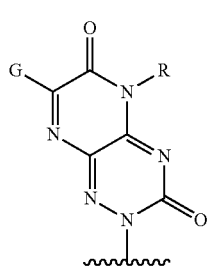

ee
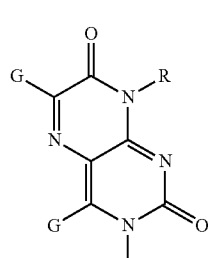

ff
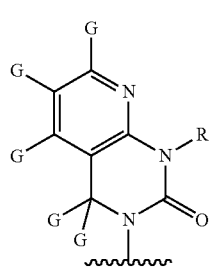

wherein G and R are defined as in structure c;

base may be a structure gg gg
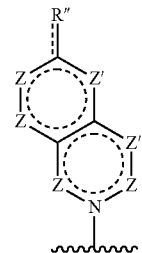

wherein each Z' is independently N (if a participant in a pi bond) or NR (if not a participant in a pi bond) and R", R, and Z are defined as in structure c;

base may be a structure hh hh
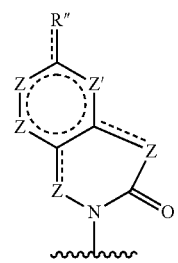

wherein each Z' is independently N (if a participant in a pi bond) or NR (if not a participant in a pi bond), and each Z in independently CG (if a participant in a pi bond) or >C(G)2 (if not a participant in a pi bond), wherein R" and G are defined as in structure c;

base may be a structure ii ii
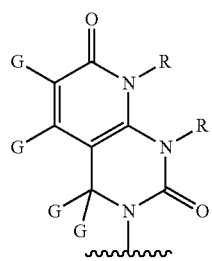

wherein R and G are defined as in structure c;

base may be a structure jj jj
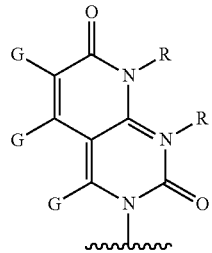

wherein R and G are defined as in structure c; or base may be a structure kk

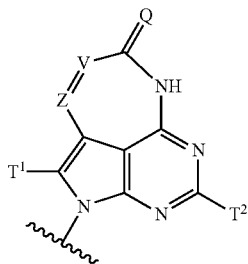

wherein for structure kk:
R is selected from the group consisting of hydrogen and $C_1$-$C_3$ alkyl;
X is selected from the group consisting of hydrogen, halo, and $OW^2$;
Y is selected from the group consisting of a bond, O, and $CH_2$;
Q is absent or is selected from the group consisting of O, S, and NH, provided that when Q is absent, V and NH are both attached to a $CH_2$ group;
V is selected from the group consisting of N and C-G;
Z is selected from the group consisting of N and C-G';
G and G' are independently selected from the group consisting of hydrogen, amino, aminocarbonyl, methylamino, dimethylamino, acylamino, alkoxyamino, —$SO_3H$, —$SO_2NH_2$, aminocarbonylamino, oxycarbonylamino, HR'NCHR"C(O)NH—, azido, cyano, halo, hydroxyamino, and hydrazino, where R' is hydrogen and R" is a side-chain of an amino acid or where R' and R" together with the nitrogen and carbon bound to each group respectively form a pyrrolidinyl group;
provided that V and Z are not identical;
provided that when V is C—H, Z is N;
$T^1$ and $T^2$ are independently selected from the group consisting of hydrogen, hydroxyl, $C_1$-$C_4$-alkoxy, $C_1$-$C_4$-thioalkoxy, amino, substituted amino, and halo; and
each of W, $W^1$, and $W^2$ is independently selected from the group consisting of hydrogen, $C_1$-$C_4$ alkyl, and a prodrug group; or
base may be a structure ll

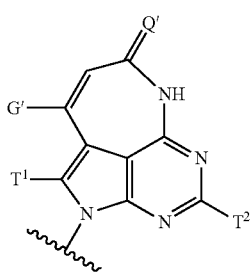

wherein for structure ll:
R is $C_1$-$C_3$ alkyl;
X is selected from the group consisting of hydrogen, halo, and $OW^2$;
Q' is selected from the group consisting of NH, O, and S;
G' is selected from the group consisting of amino, aminocarbonyl, methylamino, dimethylamino, acylamino, —$SO_3H$, —$SO_2NH_2$, alkoxyamino, aminocarbonylamino, oxycarbonylamino, HR'NCHR"C(O)NH—, azido, cyano, halo, hydroxyamino, and hydrazino, where R' is hydrogen and R" is a side-chain of an amino acid or where R' and R" together with the nitrogen and carbon bound to each group respectively form a pyrrolidinyl group; Y is selected from the group consisting of a bond, O, and $CH_2$; and each of W, $W^1$, and $W^2$ is independently selected from the group consisting of hydrogen, $C_1$-$C_4$ alkyl, and a prodrug group; or
base may be a structure mm

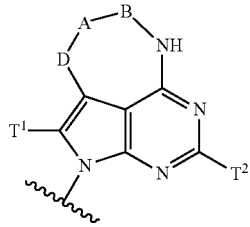

where in for structure mm
Q is as defined for structure kk
A and B are independently selected from the group consisting of C=Q, NH, and methylene optionally substituted with 1 to 2 halo groups, provided that A and B are not both NH; D is NH, or -D-A-B— together form a —N=CH—NH—, —(C=Q)-$CH_2$—(C=Q)-, —(C=Q)-NH—(C=Q)-, —(CX')=(CX')—(C=Q)-, or —CH=CH—NH— group where X' is halo;
each Q is independently selected from the group consisting of O, S, and NH; R is selected from the group consisting of hydrogen and $C_1$-$C_3$ alkyl;
X is selected from the group consisting of hydrogen, halo, and $OW^2$;
$T^1$ and $T^2$ are independently selected from the group consisting of hydrogen, hydroxyl, $C_1$-$C_4$-alkoxy, $C_1$-$C_4$-thioalkoxy, amino, substituted amino, and halo;
Y is selected from the group consisting of a bond, O, and $CH_2$; and each of W, $W^1$, and $W^2$ is independently selected from the group consisting of hydrogen, $C_1$-$C_4$ alkyl, and a prodrug group;
and pharmaceutically acceptable salts, tautomers, pharmaceutically acceptable salts of tautomers, salts (acidic or basic addition salts), hydrates, solvates, crystalline forms thereof; optionally in combination with one or more antiviral, antibacterial, or antiproliferative agents.

Not to be limited by way of example, the following exemplified embodiments are intended to convey information related to methods of making and using the disclosed and claimed compounds.

Compound Preparation

General Preparation of 2'-(R)-2'-C-Methyl-2'-deoxynucleosides

The preparation of 2'-substituted-2'-deoxynucleosides is illustrated in Scheme 1 below. Treatment of compound 1 with TIPDSCl followed by reaction of the resulting intermediate with mono-methyl oxalyl chloride gives compound 3. Treatment of 3 with AIBN/n-$BuSn_3H$ followed by desilylation with TBAF provides 2'-substituted-2'-deoxynucleoside 6. Intermediate 4 also can be prepared by treatment of 2 with PhOCSCl followed by reductive deoxygenation as used for 4 from 3.B and $R^{2'}$ are defined as above.

Scheme 1

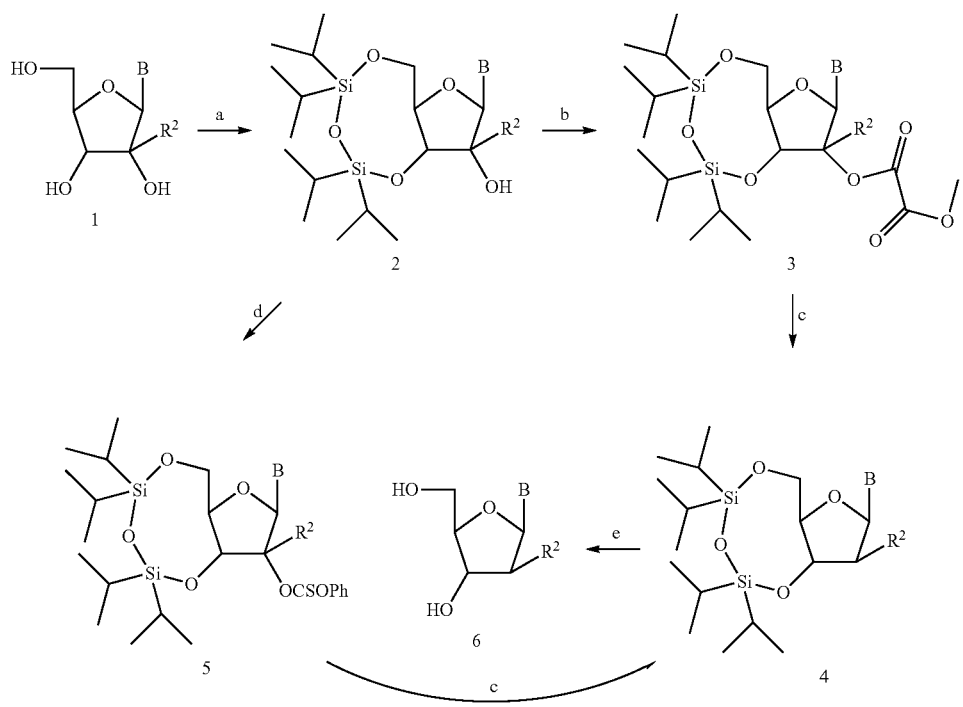

Conditions: a) TIPDSCl/imidazole; b) mono-methyl oxalyl chloride; c) AIBN/n-Bu₃SnH; d) PhOCSCl/DMAP; e) TBAF Preparation of 2'-(R)-2'-C-Methyl-2'-deoxyuridine Above general method for the preparation of 2'-substituted-2'-deoxynucleosides is exemplified in Scheme 2 for the synthesis of 2-(R)-2'-C-methyl-2'-deoxyuridine. Treatment of 2'-C-methyl-uridine with TIPDSCl in pyridine or in the presence of imidazole followed by reaction of the resulting intermediate 8 with mono-methyl oxalyl chloride gave compound 9 in good yield. Deoxygenation of 9 was accomplished by treatment of 9 with AIBN/n-Bu₃SnH to give 10, which upon deprotection gave 2'-(R)-2'-C-methyl-2'-deoxyuridine (11).

Scheme 2

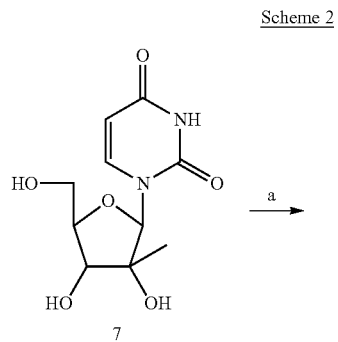

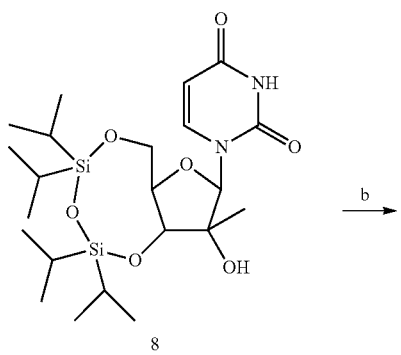

-continued

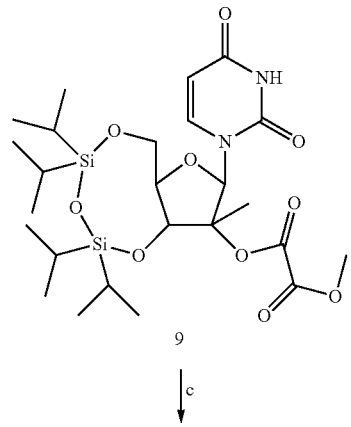

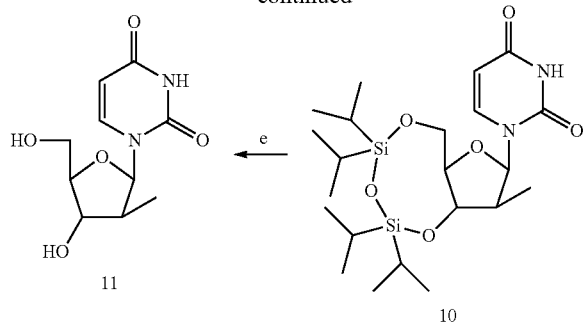
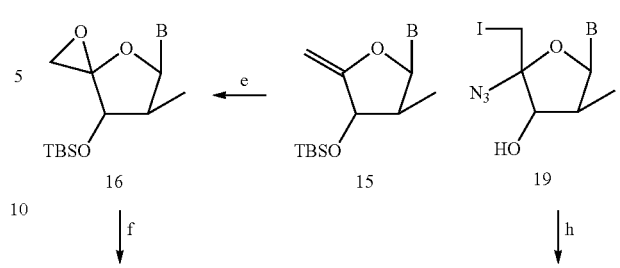

Conditions: a) TIPDSCl/imidazole; b) mono-methyl oxalyl chloride;
c) AIBN/n-Bu₃SnH; d) TBAF;

Conditions: a) I₂/Ph₃P; b) NaOMe or DBU; c) ICl/NaN₃; d) TBSCl;
e) DMDO/acetone; f) TMSN₃/SnCl₄; g) TBAF; h) 1. BzCl; 2. MCPBA/MCBA;
i) NH₃

General Preparation of 2'-(R)-4'-Azido-2'-C-methyl-2'-deoxynucleosides

General synthesis of 2'-(R)-4'-azido-2'-C-methyl-2'-deoxynucleosides is shown in Scheme 3. Treatment of compound 12 with iodine in the presence of triphenylphosphine followed by elimination in the presence of base, such as, NaOMe or DBU or the like, gives 4'-methylene-nucleoside 14. Protection of 3'-OH of 14 by treatment with TBSCl in the presence of imidazole provides compound 15. Epoxidation of 15 followed by ring-opening by treatment of epoxide with TMSN₃ in the presence of SnCl₄ also affords 4'-azido-nucleoside 18 after deprotection of 17 by TBAF. Compound 18 also can be prepared by azizo-iodination of 14. Treatment of 14 with ICl and NaN₃ gives 4'-azido-5'-iodo-nucleoside 19 in good yield. 3'-OH protection with BzCl followed by 5'-iodo-oxidation with m-chloroperbenzoic acid in the presence of m-chlorobenzoic acid provides the protected nucleoside 20. Deprotection of 20 also affords 4'-azido-nucleosides 18.

Preparation of 2'-(R)-4'-Azido-2'-C-methyl-2'-deoxycytidine (Scheme 4)

Scheme 4 illustrated the preparation of 2'-(R)-4'-azido-2'-C-methyl-2'-deoxycytidine. Treatment of compound 11 with iodine in the presence of triphenylphosphine followed by elimination catalyzed by NaOMe in MeOH gave compound 22 in good yield. Reaction of 22 with IN₃ provided intermediate 27. Protection of 3'-OH of 27 by treatment with BzCl in pyridine followed by oxidation of 5'-iodine with mCPBA in the presence of mCBA afforded protected uridine analog 28. The target nucleoside 26 was prepared by treatment of 28 with triisopropylbenzenesulfonyl chloride in the presence of DMAP followed by ammonium hydroxide then methanolic ammonia. Compound 26 can also be prepared through expoxide intermediate 24 by treatment of compound 23 with DMDO/acetone followed by ring-opening with TMSN₃ in the presence of SnCl₄ and conversion of uridine analog to cytidine derivative.

Scheme 3

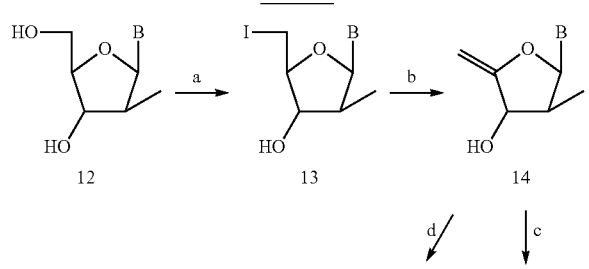

Scheme 4

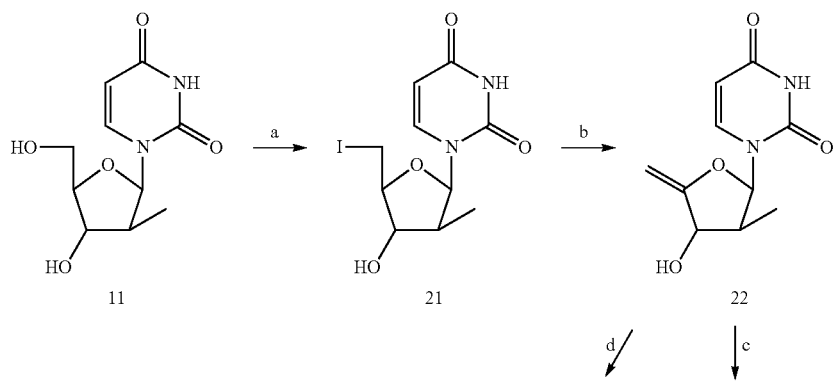

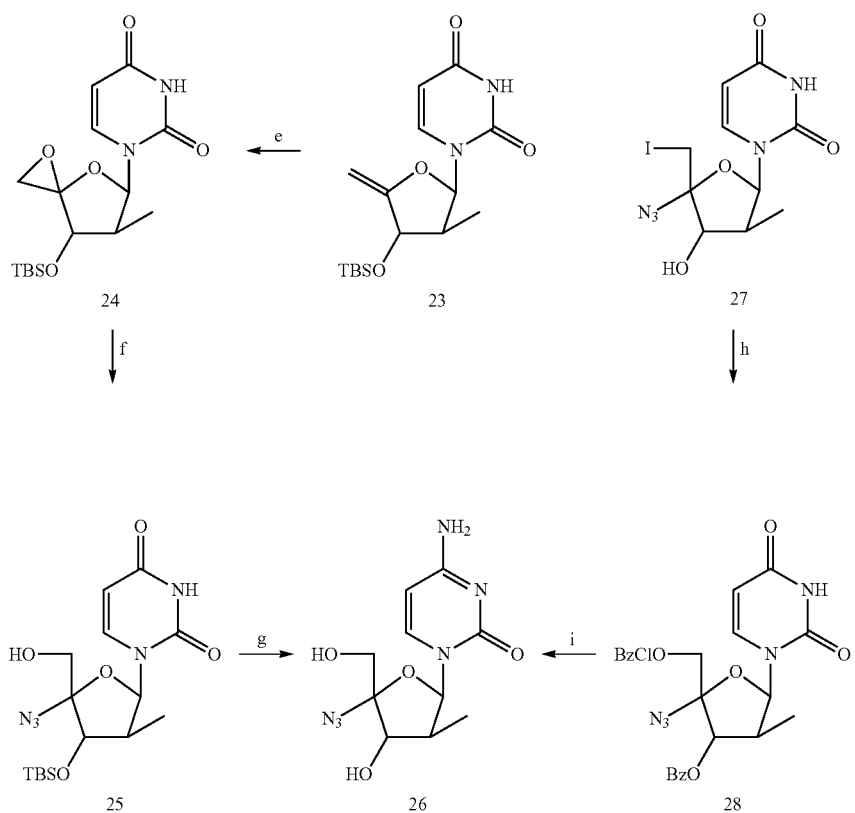

Conditions: a) I₂/Ph₃P; b) NaOMe; c) ICl/NaN₃; d) TBSCl; e) DMDO/acetone; f) TMSN₃/SnCl₄;
g) 1. TBSCl, 2. TIPBSCl/DMAP, 3. TBAF; h) 1. BzCl; 2. mCPBA/mCBA; i) 1. TIPBSCl/DMAP, 2. NH₃

Preparation of Aldehyde Intermediates 49 and 50 (Scheme 5)

Treatment of compound 42 with DMTrCl in pyridine in the presence of DMAP followed by TBSCl/imidazole selectively gave compound 44 in excellent yield. Deoxygentation of compound 44

Scheme 5

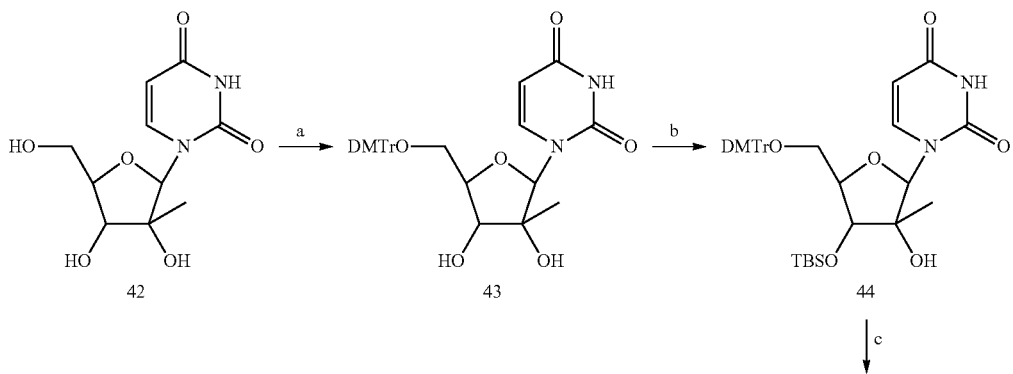

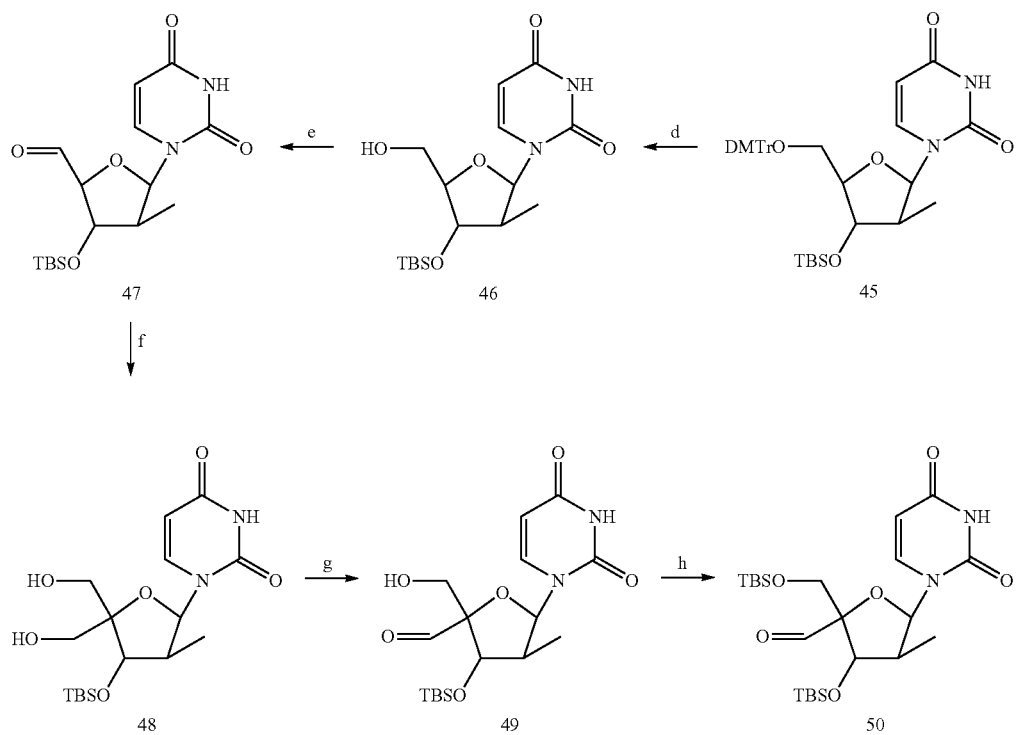

Regents and conditions: a) DMTrCl/DMAP/Pry.; b) TBSCl/imidazole; c) i. ClCOCO₂Me/DMAP/Et₃N, ii. AIBN(TMS)₃SiH; d) TFA; e) Dess-Martin Oxidation; f) i. CH₂O/NaOH, ii. NaBH₄; g) Dess-Martin Oxidation; h) TBSCl/imidazole.

was accomplished by treatment with methyl chlorooxoacetate in the presence of DMAP followed by AIBN/(TMS)₃SiH in toluene to provide 2'-deoxynucleoside intermediate 45. Detritylation of 45 followed by Dess-Martin oxidation afforded aldehyde 47. Compound 47 was subject to Aldol-condesation followed by reduction with NaBH₄ gave diol 48. Selective oxidation of 48 by Dess-Martin reagent provided intermediate 49. 5'-Hydroxy of 49 was protected with silyl to afforded intermediate 50.

Preparation of 4'-C-cyano-2'-methyl-2'-deoxycytidine (Scheme 6)

Treatment of compound 49 with hydroxylamine hydrochloride in pyridine followed by heating with acetic anhydride at 120° C. in the presence of sodium acetate gave compound 52. Amination of compound 52 was accomplished by treatment of 52 with tosyl chloride in the presence of N-methylpiperidine and triethylamine followed by ammonium hydroxide to afford cytidine intermediate 53. Desilylation of 53 with TEAF and acetylation followed by treatment with methanolc ammonia produced compound 55.

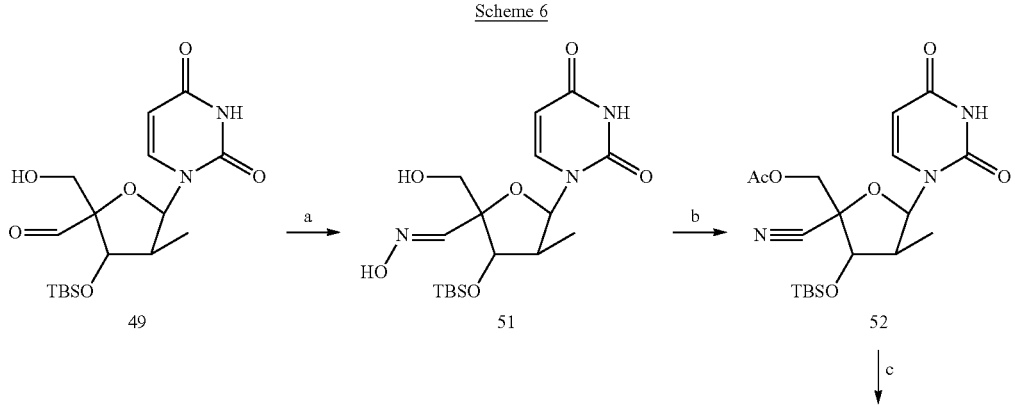

Scheme 6

-continued

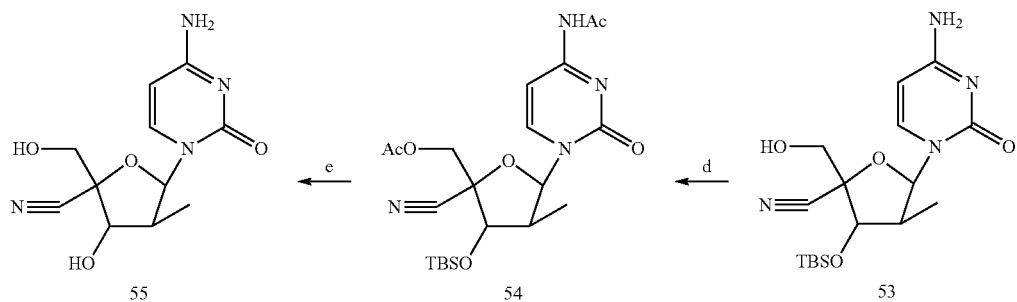

Reagents and conditions: a) NH₂—HCl/Pyr; b) NaOAc/Ac₂O; c) i. TsCl/N-methylpiperidine/Et₃N, ii. NH₄OH; d) i. TEAF, ii. Ac₂O/Pyr.; e) NH₃.

Preparation of 4'-C-vinyl-2'-methyl-2'-deoxycytidine (Scheme 7)

Treatment of aldehyde 50 with methyltriphosphonium chloride in the presence of LiBu gave 4'-C-vinyl intermediate 56. Compound 58 was prepared by similar fashion. Further elimination of 58 to 4'-C-ethynyl analog was accomplished by treatment of 58 with LiBu. Using similar method for preparation of compound 53 from 52, amination of compounds 56 and 59 gave compounds 57 and 60, respectively.

Scheme 7

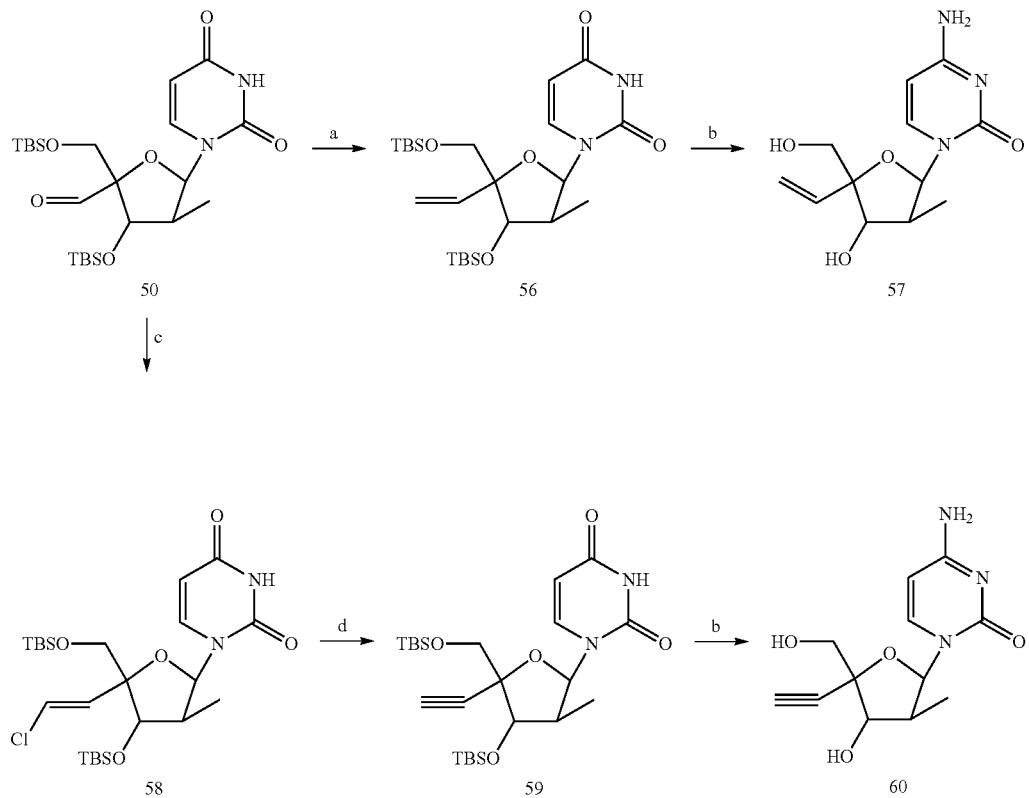

Reagents and conditions: a) methyltriphosphonium chloride/LiBu; b) i. TsCl/N—Me-piperidine/Et₃N, ii. NH₄OH, ii. NH₄F; c) chloromethyltriphosphonium chloride/LiBu; d) LiBu.

Preparation of 4'-C-hydroxymethyl-2'-methyl-2'-deoxycytidine (Scheme 8)

Acetylation of compound 48 with acetyl anhydride gave fully protected intermediate 61. Similarly, amination of 61 followed by deprotection provided 4'-C-hydroxymethyl-2'-methyl-2'-deoxycytidine 62.

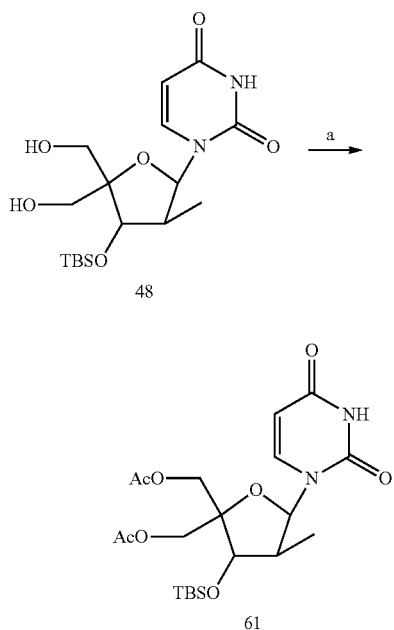

Reagents and conditions: a) Ac₂O/Pry.; b) i. TsCl/N—Me-piperidine/Et₃N, ii. NH₄OH, ii. NH₄F.

Preparation of 4'-C-allyl- and 4'-C-cyano-2'-methyl-thymidine (Scheme 9)

Epoxidation of compound 63 with DMDO followed by treatment of the resulting epoxide by allyltrimethylsilane in the presence of SnCl₄ gave silyl protected intermediate 65. Treatment of 65 with methanolic ammonia followed by ammonium fluoride in MeOH provided 4'-C-allyl-nucleoside 69.

Similarly, compound 70 was prepared from intermediate 64 when trimethylsilyl cyanide was used as nucleophile for the epoxide opening.

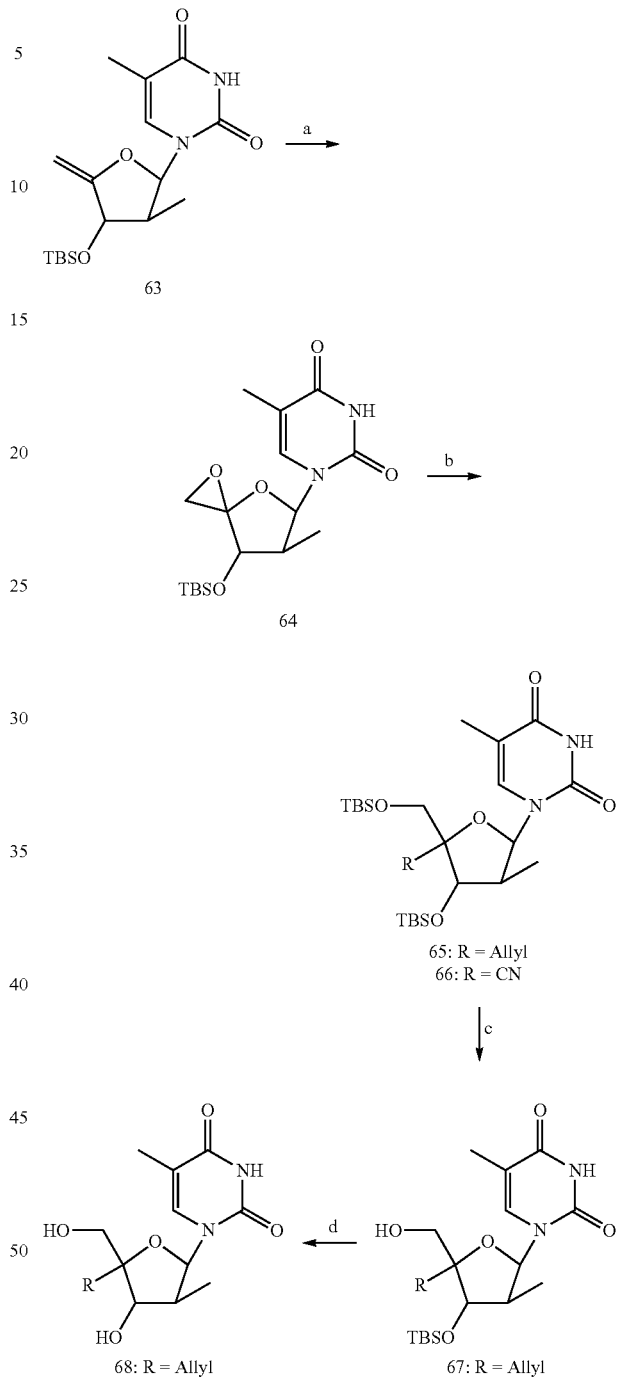

Reagents and conditions: a) DMDO; b) Allyltrimethylsilane/SnCl₄ for 65, timethylsilyl cyanide/SnCl₄ for 66; NH₃/MeOH; NH₄F/MeOH Preparation of 4'-C-ethynyl-2'-methylthymidine (Scheme 10)

Treatment of compound 64 with tri(allyl)alumina followed by desilylation gave products 73 and 74 after separation.

Scheme 10

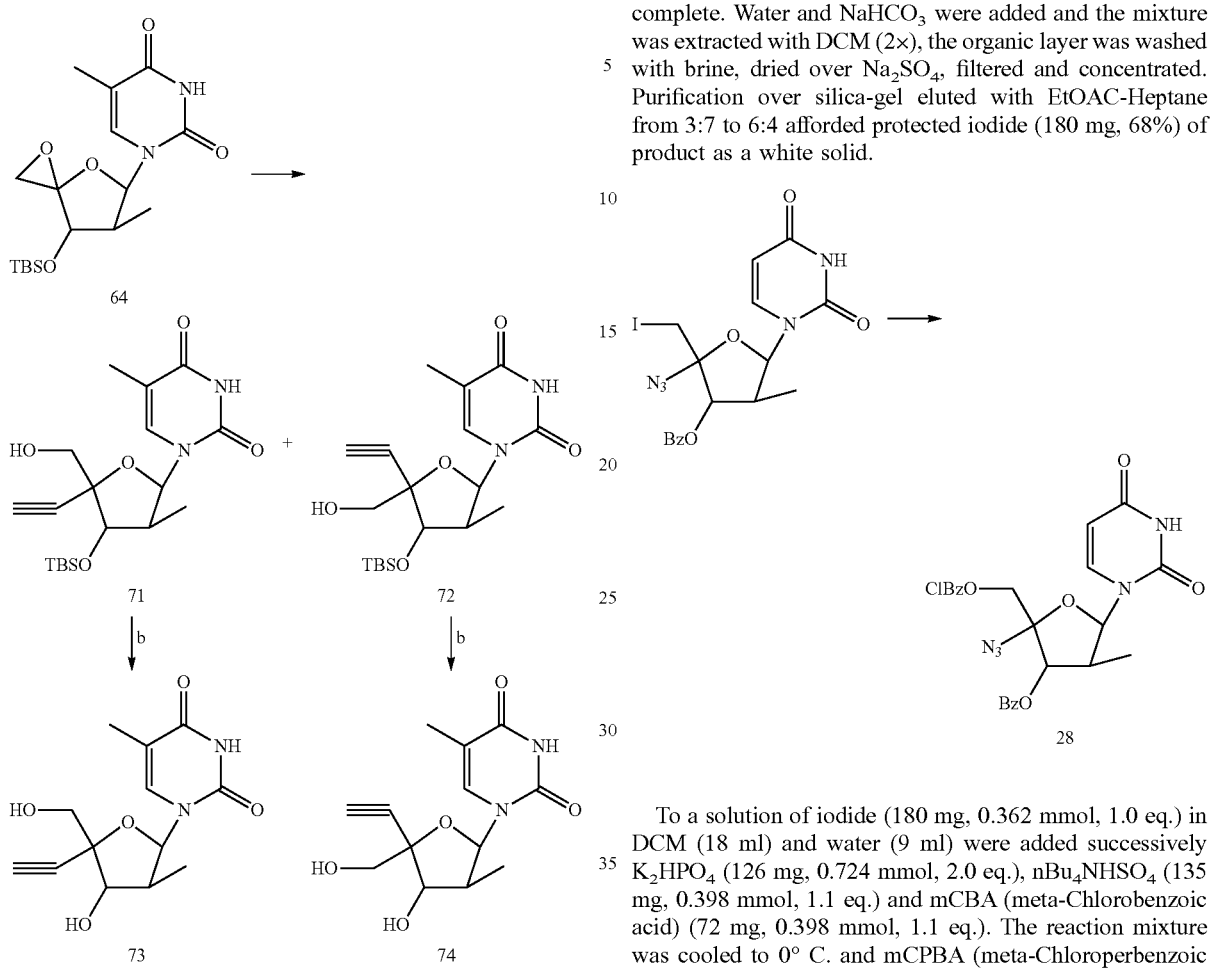

Reagents and conditions: a) (allyl)₃Al; b) NH₄F.

Experiment Details

Synthesis of Compound 28

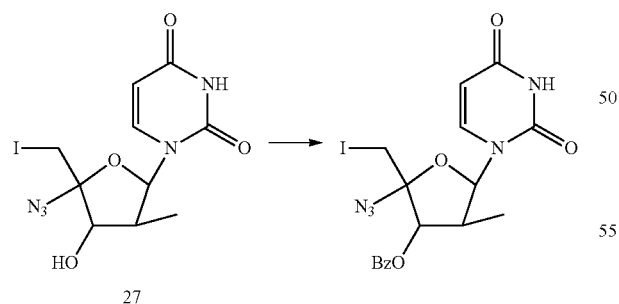

Compound 27 was prepared from starting nucleoside, 2'-C-methyl-2'-deoxyuridine, by treatment with $I_2/Ph_3P$ and elimination catalyzed by NaOMe followed by azido-iodination with $NCl/NaN_3$.

To a solution of the alcohol (203.7 mg 0.53 mmol, 1.0 eq.) in dichloromethane (DCM) was added triethylamine (TEA) (148 µl, 1.06 mmol, 2.0 eq.) and dimethylaminopyridine (DMAP, catalytic amount). After 5 minutes, benzoyl chloride (BzCl, 68 µl, ~0.58 mmol, 1.1 eq.) was added and the reaction was monitored by LCMS (liquid chromatography-mass spectroscopy). After 10 minutes the reaction was complete. Water and $NaHCO_3$ were added and the mixture was extracted with DCM (2×), the organic layer was washed with brine, dried over $Na_2SO_4$, filtered and concentrated. Purification over silica-gel eluted with EtOAC-Heptane from 3:7 to 6:4 afforded protected iodide (180 mg, 68%) of product as a white solid.

To a solution of iodide (180 mg, 0.362 mmol, 1.0 eq.) in DCM (18 ml) and water (9 ml) were added successively $K_2HPO_4$ (126 mg, 0.724 mmol, 2.0 eq.), $nBu_4NHSO_4$ (135 mg, 0.398 mmol, 1.1 eq.) and mCBA (meta-Chlorobenzoic acid) (72 mg, 0.398 mmol, 1.1 eq.). The reaction mixture was cooled to 0° C. and mCPBA (meta-Chloroperbenzoic acid) 77% (243 mg, 1.086 mmol, 3.0 eq.) was added and the reaction was left to reach room temperature. After 14 hours LCMS indicated completion of the reaction. Saturated aqueous $NaHCO_3$ and $Na_2SO_3$ were added to the reaction mixture and the mixture was extracted with EtOAc (100 ml). The organic layer was washed with brine and dried over $Na_2SO_4$, filtered and concentrated. The residue was purified by FCC over silica-gel, eluted with EtOAc—Heptane from 7:3 to 5:5 to yield 145 mg (76%) of product 28 as a white solid.

Synthesis of Compound 26

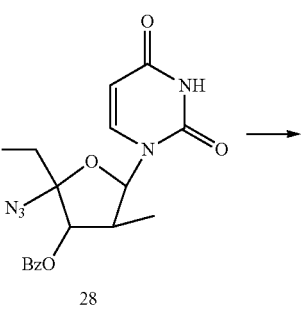

28

-continued

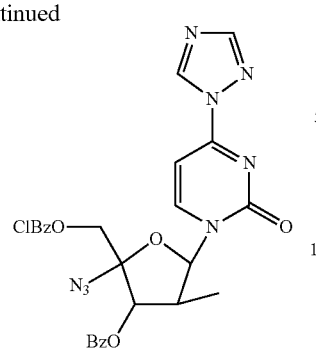

A mixture of POCl$_3$ (94 μl, 1.009 mmol, 4.0 eq.) and triazole (331 mg, 4.793 mmol, 19.0 eq.) in dry MeCN (5 ml) was stirred at 0° C. for 5 minutes followed by a slow addition of TEA (0.74 ml). The resulting mixture was left at 0° C. for 1 hour and then a solution of the uridine (28, 163 mg, 0.252 mmol, 1.0 eq.) in dry MeCN (5 ml) was added. The reaction mixture was stirred at room temperature for 14 hours then filtered through a pad of celite and the solid was washed with 3 ml of MeCN. EtOAc was added (70 ml) and the solution was washed with saturated aqueous NaHCO$_3$, water, brine, and then the solution was concentrated. The residue was co-evaporated with dioxane (20 ml). The residue was used in the next step without purification.

To a solution of the triazole (159 mg) in MeOH (5 ml) was added sodium methoxide (~240 μl, 25% wt. in MeOH, 4.0 eq.). After 30 minutes, LCMS showed the reaction was complete. To the reaction mixture was added HCl (1.1 ml, 1N, 4.0 eq.) and the mixture was concentrated. The residue was purified over silica gel, eluted with DCM-MeOH from 1% to 6% to yield 44 mg (54%) of the product as an oil.

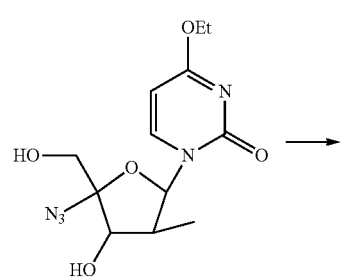

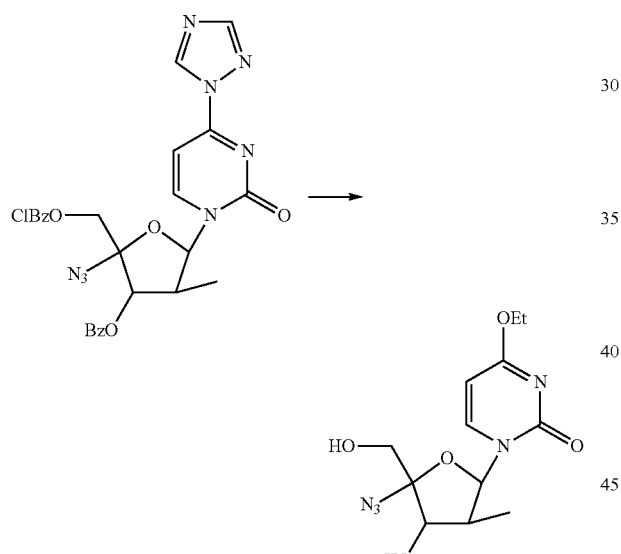

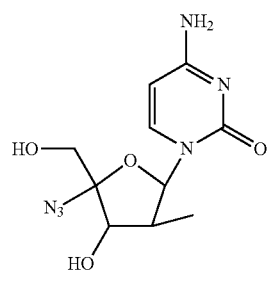

26

The methoxy compound (40 mg, 135 mmol, 1.0 eq.) was dissolved in 0.5N ammonia in dioxane (5 ml). The reaction mixture was heated to 120° C. in a microwave (250 W, 150 PSI) for 3 hours. Progress of the reaction was followed by LCMS. Upon completion of the reaction the solvent was removed and the residue was purified over silica gel eluted with DCM-EtOH from 95:5 to 80:20 to yield 16.8 mg of the desired product 26 as a syrup.

The products listed below are prepared using a similar procedure described above.

| Product | H-NMR data of products | MS | Starting material |
|---|---|---|---|
| ![structure 29] 29 | (360 MHz, CD3OD): 1.33 (d, J = 25.2 Hz, 3H), 3.80 (m, 2H), 4.13 (d, J = 21.6 Hz, 1H), 5.94 (d, J = 7.2 Hz, 1H), 6.53 (d, J = 10.8 Hz, 1H), 8.08 (d, J = 6.1 Hz, 1H). | M + 1 = 301.13 (calc 300.10) for C10H13FN6O4) | ![starting material] |

| Product | H-NMR data of products | MS | Starting material |
|---|---|---|---|
| 30 | (360 MHz, CD3OD): 3.80 (m, 2H), 4.57 (dd, J = 3.6, 21.6 Hz, 1H), 5 (dd, J = 3.6, 50.4 Hz, 1H), 5.94 (d, J = 7.2 Hz, 1H), 6.16 (d, J = 21.6 Hz, 1H), 7.93 (d, J = 7.2 Hz, 1H). | M + 1 = 2871.0 (calc 286.08) for C9H11FN6O4 | |
| 31 | (360 MHz, CD3OD): 1.39 (d, J = 22.3 Hz, 1H), 3.80 (m, 1H), 4.20 (d, 25.2 Hz, 1H), 5.74 (d, J = 7.2 Hz, 1H), 6.40 (d, J = 14.4 Hz, 1H), 7.95 (d, J = 8.2 Hz, 1H). | M + 1 = 302.12 (calc 301.08) for C10H12FN5O5 | |
| 32 | (360 MHz, CD3OD): 3.76 (m, 2H), 4.59 (dd, J = 3.6, 21.6 Hz, 1H), 5.22 (dd, J = 3.6, 54.0 Hz, 1H), 5.70 (d, J = 10.8 Hz, 1H), 6.16 (dd, J = 1.4, 18.0 Hz, 1H), 7.85 (d, J = 8.2 Hz, 1H). | M + 1 = 288.10 (calc 287.07) for C9H10FN5O5 | |
| 33 | (400 MHz, CD3OD): 3.90 (dd, J = 12.4 Hz, 2H), 4.50 (t, 12.8 Hz, 1H), 5.93 (d, J = 7.6 Hz, 1H), 6.40 (br. S, 1H), 7.71 (d, J = 7.6 Hz, 1H). | M + 1 = 305.10 (calc 304.07) for C9H10F2N6O4 | |

| Product | H-NMR data of products | MS | Starting material |
|---|---|---|---|
| 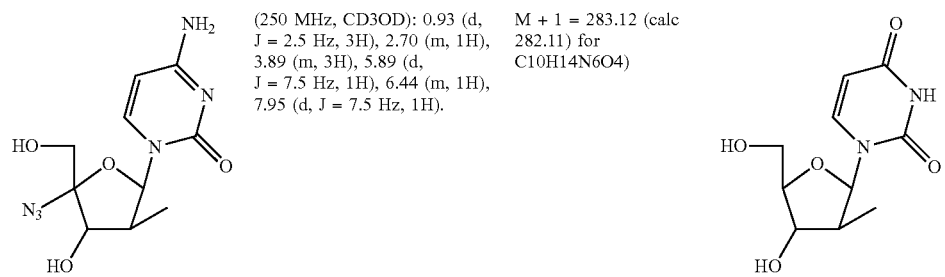
34 | (400 MHz, DMSO-d6): 4.52 (m, 1H), 5.75 (d, = 8.0 Hz, 1H), 5.86 (t, J = 6.0 Hz, 1H), 6.20 (t, J = 7.61 Jz, 1H), 6.78 (d, 6.8 Hz, 1H), 7.68 (d, J = 8.0 Hz, 1H), 11.66 (s, 1H). | M + 1 = 306.05 (calc 305.06) for C9H9F2N5O5 | |
| 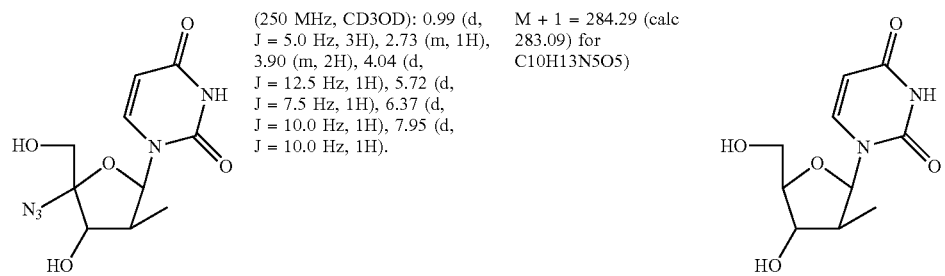
35 | (250 MHz, CD3OD): 0.93 (d, J = 2.5 Hz, 3H), 2.70 (m, 1H), 3.89 (m, 3H), 5.89 (d, J = 7.5 Hz, 1H), 6.44 (m, 1H), 7.95 (d, J = 7.5 Hz, 1H). | M + 1 = 283.12 (calc 282.11) for C10H14N6O4 | |
| 36 | (250 MHz, CD3OD): 0.99 (d, J = 5.0 Hz, 3H), 2.73 (m, 1H), 3.90 (m, 2H), 4.04 (d, J = 12.5 Hz, 1H), 5.72 (d, J = 7.5 Hz, 1H), 6.37 (d, J = 10.0 Hz, 1H), 7.95 (d, J = 10.0 Hz, 1H). | M + 1 = 284.29 (calc 283.09) for C10H13N5O5 | |
| 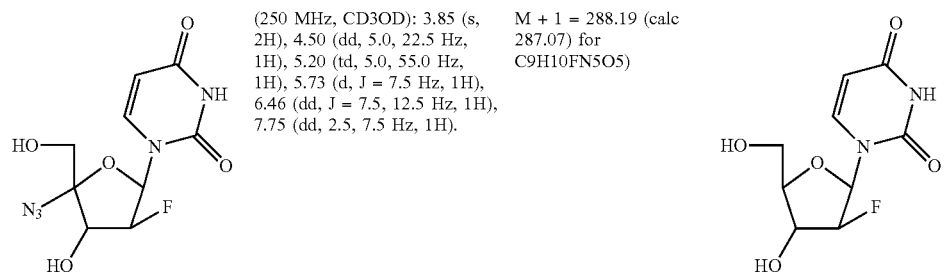
37 | (250 MHz, CD3OD): 3.85 (s, 2H), 4.50 (dd, 5.0, 22.5 Hz, 1H), 5.20 (td, 5.0, 55.0 Hz, 1H), 5.73 (d, J = 7.5 Hz, 1H), 6.46 (dd, J = 7.5, 12.5 Hz, 1H), 7.75 (dd, 2.5, 7.5 Hz, 1H). | M + 1 = 288.19 (calc 287.07) for C9H10FN5O5 | |

| Product | H-NMR data of products | MS | Starting material |
|---|---|---|---|
| 38 | (250 MHz, CD3OD): 3.85 (s, 2H), 4.49 (dd, 5.0, 22.5 Hz, 1H), 5.22 (td, 2.5, 57.5 Hz, 1H), 5.93 (d, J = 7.5 Hz, 1H), 6.49 (dd, J = 5.0, 12.5 Hz, 1H), 7.76 (d, 7.5 Hz, 1H). | M + 1 = 287.12 (calc 286.08) for C9H11FN6O4 | |
| 39 | (250 MHz, CD3OD): 0.96 (d, J = 7.5 Hz, 3H), 2.70 (m, 1H), 3.84 (dd, J = 12.5 Hz, 1H), 4.03 (d, J = 10.0 Hz, 1H), 6.37 (d, J = 7.5 Hz, 1H), 8.25 (7.5 Hz, 1H). | M + 1 = 301.16 (calc 300.10) for C10H13FN6O4 | |
| 40 | (250 MHz, CD3OD): 1.02 (d, J = 7.5 Hz, 3H), 2.71 (m, 1H), 3.92 (dd, 12.5 Hz, 1H), 4.07 (d, J = 10.0 Hz, 1H), 6.34 (d, J = 7.5 Hz, 1H), 8.30 (J = 7.5 Hz, 1H). | M + Na = 323.90 (calc 324.08 for C10H12FN5O5Na) | |
| 41 | (450 MHz, CDCl3): 0.97 (d, J = 7.2 Hz, 3H), 1.86 (d, J = 1.2 Hz, 3H), 2.08 (d, 0H), 2.19 (t, 0H), 2.68 (m, 1H), 3.84 (d, J = 12 Hz, 1H), 3.92 (d, J = 12 Hz, 1H), 4.07 (d, J = 11.2 Hz, 1H), 6.33 (d, J = 7.6 Hz, 1H), 7.83 (s, 1H). | M + 1 = 298.10 (calcd 297.11 for C11H15N5O5 | |

Synthesis of Compound 43

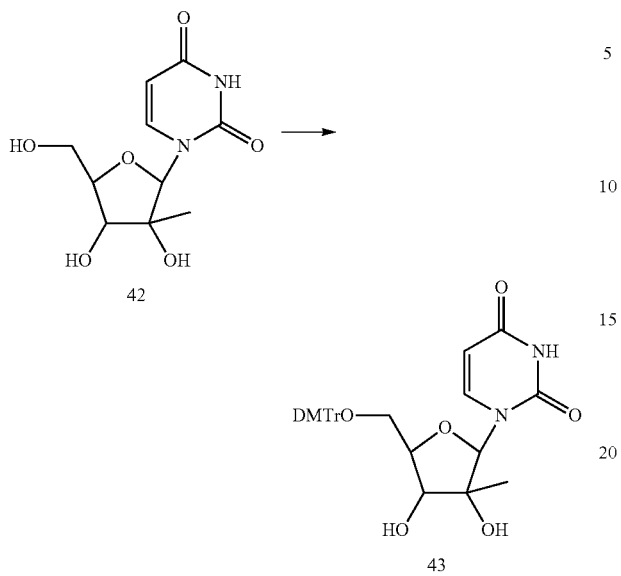

To a solution of compound 42 (1.1 g, 4.26 mmol) in anhydrous pyridine (50 mL) was added DMTrCl (2.17 g, 6.39 mmol) at rt. The mixture was stirred for 5 h, diluted with EtOAc (100 mL), washed with water (25 ml×4), and dried over sodium sulfate. After filtration and concentration, the residue was co-evaporated with toluene (30 mL) and purified by flash column chromatography (MeOH in $CH_2Cl_2$ 0 to 5%) to give 43 (1.9 g, 80%). $^1$H NMR ($CDCl_3$) δ (ppm) 9.94 (s, 1H, NH), 8.17 (d, 1H, J=8.0 Hz, H-6), 7.40-7.24 (m, 9H, aromatic), 6.84 (m, 4H, aromatic), 6.08 (s, 1H, H-1'), 5.28 (dd, 1H, J=2.0, 8.4 Hz, H-5), 4.80 (s, 1H, HO), 4.11-4.01 (m, 2H, H-3' and 4'), 3.79 (s, 6H, $(OCH_3)\times2$), 3.61 (dd, 1H, J=2.4, 11.6 Hz, H-5'), 3.55 (dd, 1H, J=2.4, 11.2 Hz, H-5"), 2.87 (d, 1H, J=9.2 Hz, HO), 1.32 (s, 3H, $CH_3$).

Synthesis of Compound 44

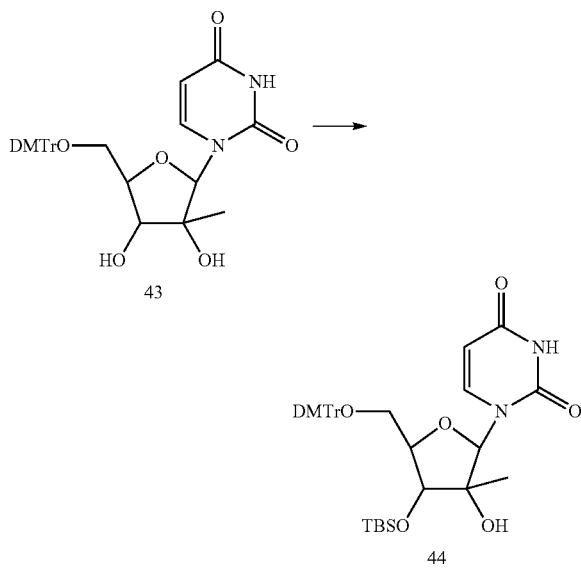

To a solution of 43 (1.9 g, 3.39 mmol) and imidazole (0.69 g, 10.17 mmol) in anhydrous $CH_2Cl_2$ (20 mL) was added TBSCl (0.77 g, 5.08 mmol) at rt. The resulting mixture was stirred at rt for 48 h. Additional imidazole (0.69 g) and TBSCl (0.77 g) were added. Then the mixture was stirred at rt for 72 h, diluted with $CH_2Cl_2$ (80 mL), washed with water (40 mL×2), and dried over sodium sulfate. After filtration and concentration, the residue was purified by flash silica gel column chromatography (0-20-35% EtOAc in hexanes) to give compound 44 (2 g, 87%) as a white solid. $^1$H NMR ($CDCl_3$) δ (ppm) 8.34 (s, 1H, NH), 8.16 (d, 1H, J=8.4 Hz, H-6), 7.32-7.17 (m, 9H, aromatic), 6.85 (m, 4H, aromatic), 6.13 (s, 1H, H-1'), 5.08 (dd, 1H, J=2.4, 8.0 Hz, H-5), 4.19 (d, 1H, J=8.4 Hz, H-3'), 4.01 (m, 1H, H-4'), 3.87 (dd, 1H, J=2.0, 10.8 Hz, H-5'), 3.80 (s, 6H, $(OCH_3)\times2$), 3.32 (dd, 1H, J=2.0, 10.8 Hz, H-5"), 1.19 (s, 3H, $CH_3$), 0.79 (s, 9H, $C(CH_3)_3$), 0.07 (s, 3H, $CH_3Si$), −0.30 (s, 3H, $CH_3Si$).

Synthesis of Compound 45

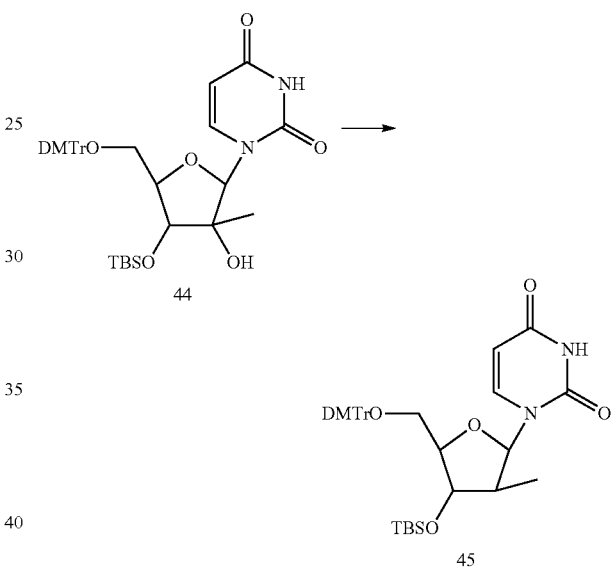

To a solution of 44 (2.0 g, 2.96 mmol), DAMP (2.17 g, 17.78 mmol), and triethylamine (2.48 mL, 17.78 mmol) in acetonitrile (40 mL) was added methyl chlorooxoacetate (1.64 mL, 17.78 mmol) dropwise under ice-water bath. The resulting mixture was stirred at rt for 1 h, diluted with EtOAc (125 mL), washed with brine (30 mL×4), and dried over sodium sulfate. After filtration and concentration, the residue was co-evaporated with toluene (20 mL×2) and dried under high vacuum for 10 min. Then the residue was dissolved in anhydrous toluene (40 mL) and bubbled with nitrogen gas for 10 min, to which TMSsilylhydride (5.49 mL, 17.78 mmol) and then AIBN (1.46 g, 8.89 mmol) were added. The resulting mixture was refluxed in preheated oil bath at 120° C. for 1.5 h and concentrated under reduced pressure. The residue was purified by flash column chromatography (0-20-35% EtOAc in hexanes) to give compound 45 (1.3 g, 67%) as a white solid. $^1$H NMR ($CDCl_3$) δ (ppm) 8.15 (d, 1H, J=8.4 Hz, H-6), 8.02 (s, 1H, NH), 7.34-7.20 (m, 9H, aromatic), 6.84 (m, 4H, aromatic), 6.30 (d, 1H, J=7.6 Hz, H-1'), 5.11 (dd, 1H, J=2.4, 8.4 Hz, H-5), 4.14 (d, 1H, J=8.0 Hz, H-3'), 3.83-3.74 (m, 8H, H-4', 5' and $(CH_3O)_2$), 3.33 (dd, 1H, J=2.4, 10.8 Hz, H-5"), 2.54 (m, 1H, H-2'), 0.98 (d, 3H, J=6.8 Hz, $CH_3$), 0.76 (d, 9H, $C(CH_3)_3$), 0.04 (s, 3H, $CH_3Si$), −0.28 (s, 3H, $CH_3Si$).

Synthesis of Compound 46

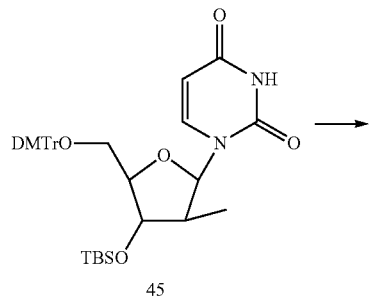

To a solution of compound 45 (1.3 g, 1.97 mmol) in anhydrous $CH_2Cl_2$ (10 mL) was added TFA (0.3 mL, 3.95 mmol) under ice-water bath. The resulting mixture was stirred at rt for 1 h, diluted with $CH_2Cl_2$ (100 mL), washed with sat.$NaHCO_3$ (30 mL×2), and dried over sodium sulfate. After filtration and concentration, the residue was purified by silica gel column chromatography (EtOAc:Hexanes=1:1) to give compound 46 (600 mg, 85%) as a white solid.

Synthesis of Compound 47

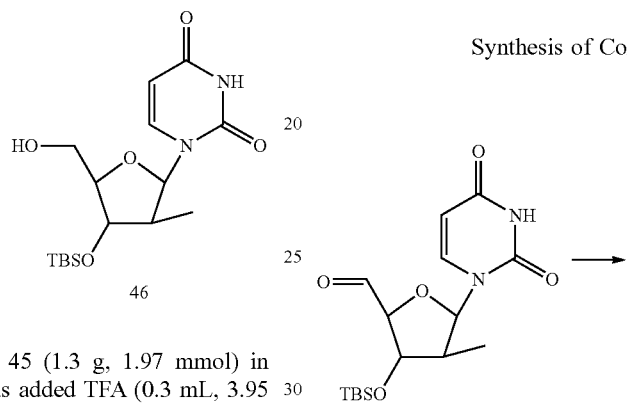

To a solution of compound 46 (3 g, 8.46 mmol) in anhydrous $CH_2Cl_2$ (30 mL) was added 15% Dess-Martin periodinane in $CH_2Cl_2$ (36 mL, 12.73 mmol) dropwise at 0° C. The reaction mixture was stirred at 0° C. for 3 h, diluted with $CH_2Cl_2$ (150 mL), washed with sodium bicarbonate solution (50 mL×3) and then with saturated solution of sodium thiosulfate (50 mL×3), and the organic layer dried over sodium sulfate. After filtration and concentration, the residue was purified by silica gel column chromatography (MeOH:$CH_2Cl_2$=1:20) to give compound 47. $^1H$ NMR (CDCl$_3$) δ (ppm) 9.79 (s, 1H, H-5'), 8.86 (s, 1H, NH), 8.26 (d, 1H, J=7.2 Hz, H-6), 6.15 (d, 1H, J=6.0 Hz, H-1'), 5.77 (d, 1H, J=8.0 Hz, H-5), 4.40 (d, 1H, J=3.6 Hz, H-4'), 4.26 (t, 1H, J=3.6 Hz, H-3'), 2.70 (m, 1H, H-2'), 0.92 (s, 9H, C(CH$_3$)$_3$), 0.76 (d, 3H, J=7.6 Hz, CH$_3$), 0.14 (s, 3H, CH$_3$Si), 0.13 (s, 3H, CH$_3$Si).

Synthesis of Compound 48

The compound 47 obtained was then dissolved in dioxane (100 mL) and 37% formaldehyde (3 mL, 36.96 mmol) was added. To the obtained solution was added 2N sodium hydroxide (5 mL, 10 mmol) dropwise at rt. The resulting reaction mixture was stirred at rt for 15 h and cooled. Then sodium borohydride (890 mg, 23.53 mmol) was added portionwise. The resulting mixture was stirred at rt for 6 h and AcOH-pyridine solution (2.5:7.5 mL) and water (100 mL) were added under ice-water. The mixture was then extracted with $CH_2Cl_2$ (50 mL×4) and the organic layer dried over sodium sulfate. After filtration and concentration, the residue was purified silica gel column chromatography (MeOH:$CH_2Cl_2$=1:40 to 1:20) to give compound 48 (2.1 g, 64%) as a white solid. $^1H$ NMR (CD$_3$OD) δ (ppm) 8.30 (d, 1H, J=8.0 Hz, H-6), 6.31 (d, 1H, J=8.0 Hz, H-1'), 5.68 (d, 1H, J=8.0 Hz, H-5), 4.29 (d, 1H, J=9.6 Hz, H-3'), 3.86 (d, 1H, J=12.0 Hz, CH-4'), 3.78 (d, 1H, J=12.0 Hz, CH-4'), 3.54 (d, 1H, J=12.0 Hz, CH-4'), 3.45 (d, 1H, J=12.0 Hz, CH-4'), 2.83 (m, 1H, H-2'), 0.98-0.88 (m, 12H, CH$_3$-2' and C(CH$_3$)$_3$), 0.15 (s, 3H, CH$_3$Si), 0.13 (s, 3H, CH$_3$Si).

Synthesis of Compound 49

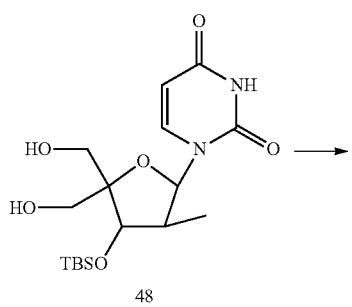

To a solution of compound 48 (1.4 g, 3.62 mmol) in CH$_2$Cl$_2$-THF (46:10 mL) was added Dess-Martin periodinane (1.8 g, 4.24 mmol) at 0° C. in one portion. The mixture was stirred at 0° C. for 2 h. After temperature was raised to 10° C., the mixture was stirred for 1 h and sodium thiosulfate (1.0 g) was added. Then the mixture was stirred for 30 min and added onto top of a silica gel column, which was then eluted with CH$_2$Cl$_2$ and CH$_2$Cl$_2$-EtOAc (3:1) to give compound 49 (a mixture of desired α/β=2) as a white solid (900 mg, 64%).

Synthesis of Compound 50

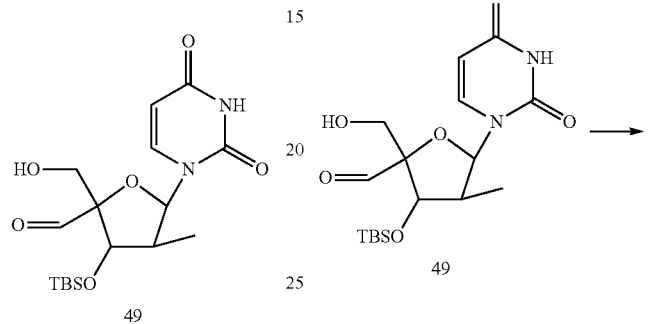

To a solution of compound 49 (500 mg, 1.30 mmol) and imidazole (530 mg, 7.8 mmol) in CH$_2$Cl$_2$ (20 mL) was added TBSCl (590 mg, 3.90 mmol) at rt. The resulting mixture was stirred for 3 h, diluted with CH$_2$Cl$_2$, washed with water, and dried over sodium sulfate. After filtration and concentration, the residue was separated by flash column chromatography (EtOAc 0 to 25% in hexanes) to give compound 50 (270 mg, 40%).

Synthesis of Compound 51

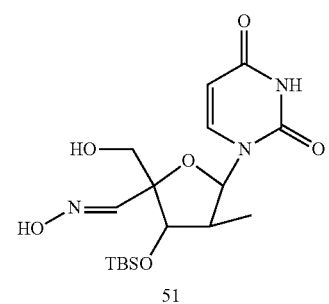

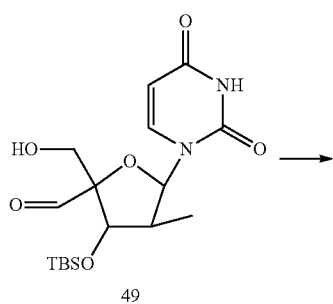

To a solution of compound 48 (220 mg, 0.57 mmol) in anhydrous CH$_2$Cl$_2$-THF (10 mL:2 mL) was added Dess-Martin periodinane (300 mg, 0.71 mmol) in one portion at 0° C. The resulting reaction mixture was stirred for 2 h and sodium thiosulfate (390 mg) was added. The mixture was stirred for 15 min at 0° C., then poured onto top of a short silica gel column, and eluted with CH$_2$Cl$_2$-EtOAc (1:1) thoroughly. The fractions were combined and concentrated in vacuo to a residue, which was then dissolved in pyridine (10 mL) and NH$_2$OH—HCl (300 mg) added. The resulting mixture was stirred at rt for 15 h and concentrated in vacuo. The residue obtained was purified by silica gel column chromatography (MeOH:CH$_2$Cl$_2$=1:40 to 1:20) to give compound 51 (107 mg, 47%) along with 4'-β-isomer (53 mg, 18%) as white solids. $^1$H NMR (CD$_3$OD) δ (ppm) 8.20 (d, 1H, J=8.0 Hz, H-6), 7.4 (s, 1H, HC=N), 6.31 (d, 1H, J=8.0 Hz, H-1'), 5.70 (d, 1H, J=8.0 Hz, H-5), 4.32 (d, 1H, J=10.0 Hz, H-3'), 3.84 (s, 2H, H-5'), 2.64 (m, 1H, H-2'), 0.94 (d, 3H, J=7.2 Hz, CH$_3$), 0.92 (s, 9H, C(CH$_3$)$_3$), 0.17 (s, 3H, CH$_3$Si), 0.13 (s, 3H, CH$_3$Si); $^1$H NMR (CD$_3$OD) for minor isomer δ (ppm) 7.71 (d, 1H, J=8.0 Hz, H-6), 7.55 (s, 1H, HC=N), 6.29 (d, 1H, J=7.6 Hz, H-1'), 5.70 (d, 1H, J=8.0 Hz, H-5), 4.37 (d, 1H, J=8.0 Hz, H-3'), 3.92 (d, 1H, J=12.4 Hz, H-5'), 3.73 (d, 1H, J=12.4 Hz, H-5"), 2.86 (m, 1H, H-2'), 0.93-0.88 (m, 12H, CH$_3$-2' and C(CH$_3$)$_3$), 0.12 (s, 3H, CH$_3$Si), 0.10 (s, 3H, CH$_3$Si).

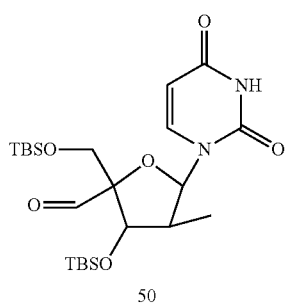

Synthesis of Compound 52

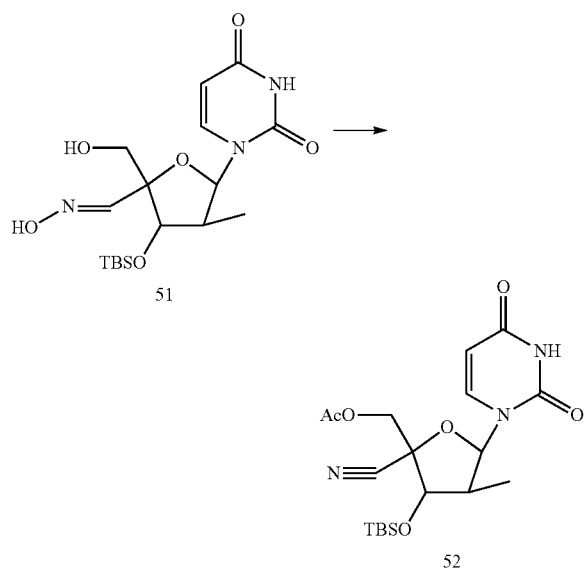

A mixture of compound 51 (160 mg, 0.40 mmol) and sodium acetate (123 mg, 1.5 mmol) in acetic anhydride (5 mL) was heated at 120° C. for 3 h and concentrated in vacuo. The obtained residue was chromatographed with a silica gel column by eluting with MeOH—CH$_2$Cl$_2$ (1:40) to give compound 52 (97 mg, 57%) as a white solid. $^1$H NMR (CDCl$_3$) δ (ppm) 10.03 (s, 1H, NH), 7.26 (d, 1H, J=8.0 Hz, H-6), 6.17 (bs, 1H, H-1'), 5.78 (d, 1H, J=8.0 Hz, H-5), 4.52 (d, 1H, J=12.4 Hz, H-5'), 4.42 (d, 1H, J=12.4 Hz, H-5"), 4.19 (bs, 1H, H-3'), 2.86 (m, 1H, H-2'), 2.17 (s, 3H, CH$_3$CO), 1.03 (d, 1H, J=7.2, CH$_3$), 0.95 (s, 9H, C(CH$_3$)$_3$), 0.15 (s, 6H, CH$_3$Si).

Synthesis of Compound 53

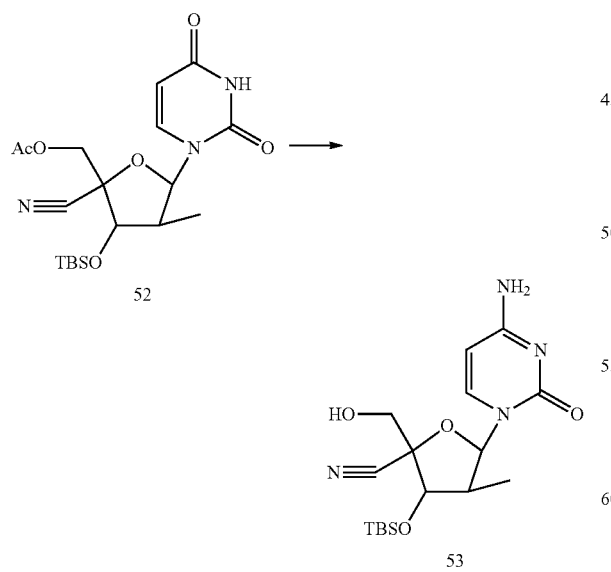

To a solution of compound 52 (200 mg, 0.47 mmol) in anhydrous CH$_3$CN (4 mL) containing triethylamine (0.20 mL, 1.42 mmol) and N-methylpiperidine (0.11 mL, 0.94 mmol) was added TsCl (270 mg, 1.42 mmol) at rt. The resulting mixture was stirred at rt for 1 h and then 29% NH$_4$OH (4 mL) was added under water bath. The resulting mixture was stirred at rt for 2 h and concentrated under 35° C. The obtained residue was purified by silica gel column chromatography (MeOH:CH$_2$Cl$_2$=1:10 to 1:4) to give compound 53 (160 mg, 89%) as a syrup.

Synthesis of Compound 54

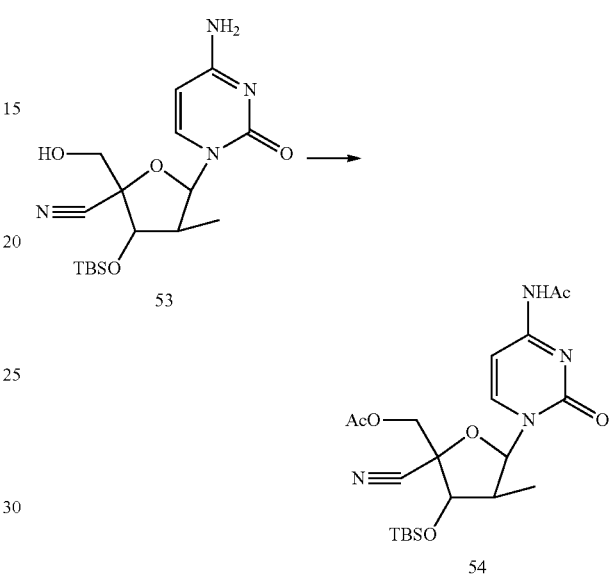

A solution of compound 53 (160 mg, 0.42 mmol) and TEAF (200 mg, 1.34 mmol) in MeOH-THF (2:4 mL) was stirred at rt for 15 h and heated at 60° C. for 4 h. After concentration, the residue was purified by silica gel column chromatography (MeOH:CH$_2$Cl$_2$=1:10 to 1:4) to give crude compound 55 (100 mg, crude, contaminated by TEAF), which was then dissolved in anhydrous pyridine, then treated with acetic anhydride, stirred at rt for 3 h, and concentrated in vacuo. The obtained residue was purified by silica gel column chromatography (MeOH:CH$_2$Cl$_2$=1:40) to give compound 54 as a syrup which was used in next reaction. $^1$H NMR (CD$_3$OD) δ (ppm) 7.97 (d, 1H, J=7.6 Hz, H-6), 7.46 (d, 1H, J=7.6 Hz, H-5), 6.23 (bs, 1H, H-1'), 5.52 (bs, 1H, H-3'), 4.65 (d, 1H, J=12.0 Hz, H-5'), 4.62 (d, 1H, J=12.0 Hz, H-5"), 3.11 (m, 1H, H-2'), 2.19 (s, 3H, CH$_3$CO), 2.19 (s, 3H, CH$_3$CO), 2.12 (s, 3H, CH$_3$CO), 0.97 (d, 3H, J=7.2 Hz, CH$_3$); MSES (M+1):393.

Synthesis of Compound 55

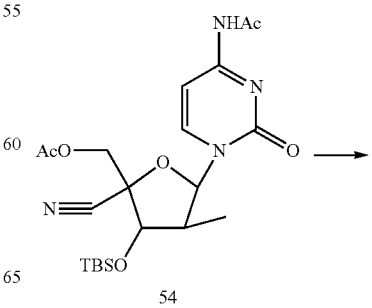

Synthesis of Compound 57

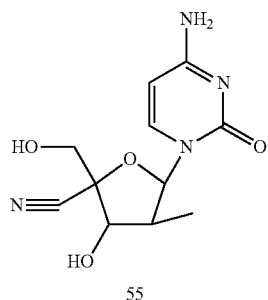

55

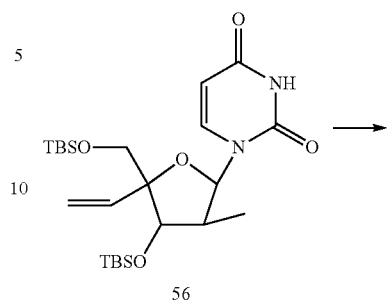

56

Compound 54 was dissolved in 7M ammonia in methanol (5 mL), stirred in a sealed flask for 15 h, and concentrated in vacuo. The obtained residue was chromatographed with silica gel column by eluting with MeOH—CH$_2$Cl$_2$ (1:4) to give compound 55 (30 mg, 27% from 53) as a white solid. UV($\lambda_{max}$) 273 nm (MeOH); $^1$H NMR (CD$_3$OD) δ (ppm) 7.85 (d, 1H, J=7.8 Hz, H-6), 6.40 (bs, 1H, H-1'), 5.88 (d, 1H, J=7.6 Hz, H-5), 4.10 (d, 1H, J=9.6 Hz, H-3'), 4.00 (d, 1H, J=12.4 Hz, H-5'), 3.92 (d, 1H, J=12.4 Hz, H-5"), 2.75 (m, 1H, H-2'), 0.95 (d, 3H, J=3.2 Hz, CH$_3$); MSES (M+1): 267.

Synthesis of Compound 56

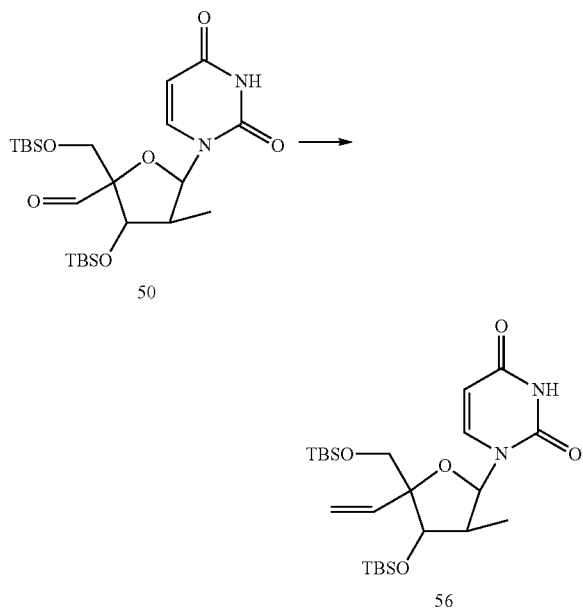

To a suspension of methyltriphenylphosphonium bromide in THF (2 mL) was added n-BuLi (2.2 M in hexanes, 0.24 mL, 0.528 mmol) in anhydrous THF (2 mL) at −78° C. The mixture was stirred at 0° C. for 1 h and compound 50 (60 mg, 0.12 mmol) in anhydrous THF (2 mL) was added. The mixture was then stirred at rt for 1 h, neutralized with saturated aqueous ammonium chloride solution, diluted with EtOAc, washed with brine, and dried over sodium sulfate. After filtration and concentration, the residue was purified by silica gel column chromatography (MeOH:CH$_2$Cl$_2$=1:40) to give compound 56 as a white solid (45 mg, 75%).

57

To a solution of compound 56 (100 mg, 0.20 mmol) in anhydrous CH$_3$CN (2 mL) containing triethylamine (0.08 mL, 0.6 mmol) and N-methylpiperidine (0.05 mL, 0.40 mmol) was added TsCl (120 mg, 0.6 mmol) at rt. The resulting mixture was stirred at rt for 1 h and then 29% NH$_4$OH (2 mL) was added under water bath. The resulting mixture was stirred at rt for 2 h and concentrated in vacuo under 35° C. The obtained residue was purified by silica gel column chromatography (MeOH:CH$_2$Cl$_2$=1:10 to 1:4) to give a protected cytidine intermediate (70 mg, 70%) as a syrup. A mixture of the intermediate (70 mg, 0.14 mmol) and ammonium fluoride (100 mg, 2.82 mmol) in methanol (10 mL) was refluxed for 6 h and another 15 h after adding additional ammonium fluoride (100 mg, 2.82 mmol). After concentration in vacuo, the residue was purified by silica gel column chromatography (MeOH:CH$_2$Cl$_2$=1:10 to 1:4) to give compound 57 (28.6 mg, 77%). UV($\lambda_{max}$) 273 nm (MeOH); $^1$H NMR (CD$_3$OD) δ (ppm) 8.28 (d, 1H, J=7.2 Hz, H-6), 6.28 (d, 1H, J=7.6 Hz, H-1'), 5.99 (dd, 1H, J=11.2, 17.2 Hz, H—C=C), 5.91 (d, 1H, J=7.6 Hz, H-5), 5.49 (dd, 1H, J=2.0, 17.2 Hz, H—C=C), 5.32 (dd, 1H, J=2.0, 10.8 Hz, H—C=C), 4.06 (d, 1H, J=10.8 Hz, H-3'), 3.72 (d, 1H, J=12.0 Hz, H-5'), 3.55 (d, 1H, J=12.0 Hz, H-5"), 2.45 (m, 1H, H-2'), 0.87 (d, 3H, J=6.8 Hz, CH$_3$); MSES: 268 (M+1), 535 (2M+1).

Synthesis of Compound 58

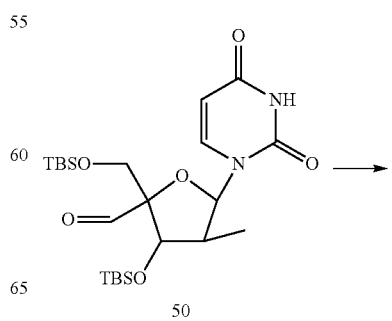

50

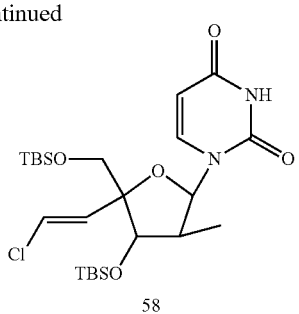

58

To a suspension of chloromethyltriphenylphosphonium chloride (390 mg, 1.12 mmol) in THF (3 mL) was added n-BuLi (2.2 M in hexanes, 0.51 mL, 1.12 mmol) at −78° C. The mixture was stirred at 0° C. for 1 h and compound 50 (140 mg, 0.28 mmol) in anhydrous THF (3 mL) was added. The resulting mixture was stirred at rt for 3 h, neutralized with saturated ammonium chloride, diluted with EtOAc, washed with brine, and dried over sodium sulfate. After filtration and concentration, the residue was purified by silica gel column chromatography (MeOH:CH$_2$Cl$_2$=1:40) to give compound 58 as a white solid (140 mg, 94%).

Synthesis of Compound 59

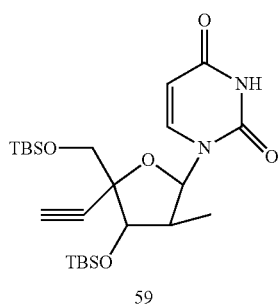

58

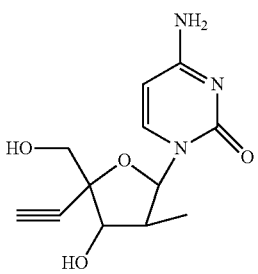

59

To a solution of compound 58 (200 mg, 0.38 mmol) in anhydrous THF (10 mL) was added n-BuLi (2.8 mL 1.6 M in hexanes, 4.52 mmol) dropwise at −78° C. The mixture was then stirred at −78° C. for 2 h, neutralized with saturated ammonium chloride solution (10 mL), diluted with EtOAc (50 mL), washed with brine (15 mL×3), and dried over sodium sulfate. After filtration and concentration, the residue was purified by silica gel column chromatography (hexanes: EtOAc=4:1) to give compound 59 (180 mg, 97%) as a white solid.); $^1$H NMR (CDCl$_3$) δ (ppm) 9.21 (bs, 1H, NH), 8.05 (d, 1H, J=8.4 Hz, H-6), 6.24 (d, 1H, J=7.6 Hz, H-1'), 5.94 (dd, 1H, J=11.2, 17.6 Hz, H—C≡C), 5.70 (dd, 1H, J=2.0, 8.0 Hz, H—C≡C), 5.52 (dd, 1H, J=1.2, 17.2 Hz, H—C≡C), 5.32 (d, 1H, J=8.4 Hz, H-5), 4.16 (d, 1H, J=10.4 Hz, H-3'), 3.64 (d, 1H, J=11.2 Hz, H-5'), 3.57 (d, 1H, J=11.6 Hz, H-5"), 2.48 (m, 1H, H-2'), 0.95 (s, 9H, C(CH$_3$)$_3$), 0.91 and 0.90 (m, 12H, C(CH$_3$)$_3$ and CH$_3$-2'), 0.12-0.10 (4s, 12H, CH$_3$Si).

Synthesis of Compound 60

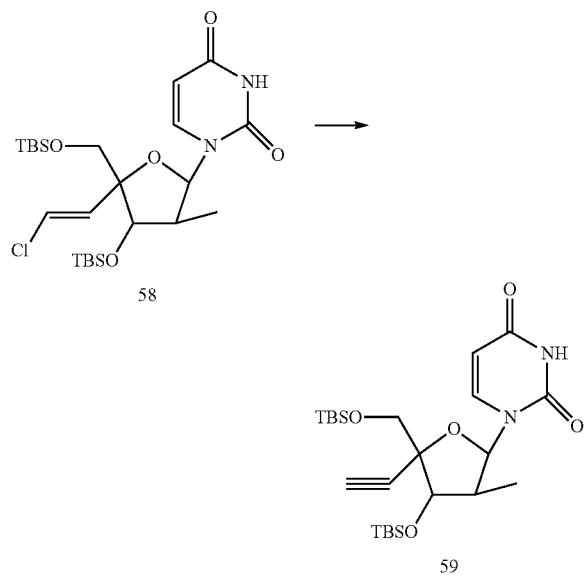

To a solution of compound 59 (100 mg, 0.20 mmol) in anhydrous CH$_3$CN (3 mL) containing triethylamine (0.08 mL, 0.6 mmol) and N-methylpiperidine (0.05 mL, 0.40 mmol) was added TsCl (120 mg, 0.61 mmol) at rt. The resulting mixture was stirred at rt for 1 h and then 29% NH$_4$OH (2 mL) was added under water bath. The resulting mixture was stirred at rt for 2 h and concentrated in vacuo under 35° C. The obtained residue was purified by silica gel column chromatography (MeOH:CH$_2$Cl$_2$=1:20 to 1:10) to give a cytidine intermediate (70 mg, 70%) as a syrup. A mixture of the intermediate (70 mg, 0.14 mmol) and ammonium fluoride (260 mg, 7.09 mmol) was heated at 90° C. in a sealed flask for 15 h and concentrated in vacuo. The residue was purified by silica gel column chromatography (MeOH:CH$_2$Cl$_2$=1:4) to give compound 60 (31.2 mg, 85%) as a white solid. UV(λ$_{max}$) 273 nm (MeOH); $^1$H NMR (CD$_3$OD) δ (ppm) 8.05 (d, 1H, J=7.6 Hz, H-6), 6.31 (d, 1H, J=8.0 Hz, H-1'), 5.89 (d, 1H, J=7.6 Hz, H-5), 3.95 (d, 1H, J=10.8 Hz, H-3'), 3.88 (d, 1H, J=12.4 Hz, H-5'), 3.79 (d, 1H, J=12.4 Hz, H-5"), 3.06 (s, 1H, H—C≡C), 2.75 (m, 1H, H-2'), 0.915 (d, 3H, J=6.8 Hz, CH$_3$).

Synthesis of Compound 61

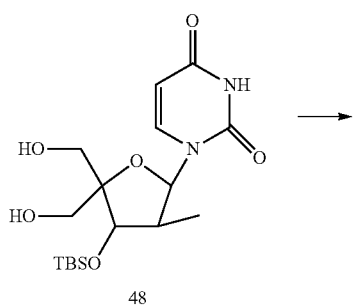

48

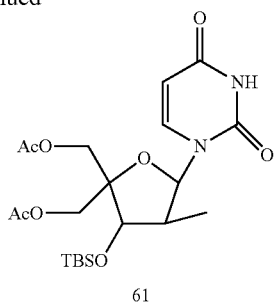

61

To a solution of compound 48 (220 mg, 0.57 mmol) in anhydrous pyridine (4 mL) was added acetic anhydride (0.27 mL, 2.85 mmol) at rt. The resulting mixture was stirred at rt for 5 h and concentrated in vacuo. The resulting mixture was purified by silica gel column chromatography (MeOH:CH$_2$Cl$_2$=1:40) to give compound 61 (220 mg, 82%) as a white solid. $^1$H NMR (CDCl$_3$) δ (ppm) 9.80 (bs, 1H, NH), 7.62 (d, 1H, J=8.0 Hz, H-6), 6.26 (d, 1H, J=7.2 Hz, H-1'), 5.74 (d, 1H, J=8.4 Hz, H-5), 4.53 (d, 1H, J=12.4 Hz, HC-4'), 4.35 (d, 1H, J=12.0 Hz, H-5'), 4.24 (d, 1H, J=12.0 Hz, H-5"), 4.05 (d, 1H, J=7.2 Hz, H-3'), 3.99 (d, 1H, J=12.0 Hz, HC-4'), 2.82 (m, 1H, H-2"), 2.15 (s, 3H, CH$_3$CO), 2.12 (s, 3H, CH$_3$CO), 0.96 (d, 3H, J=7.2 Hz, CH$_3$), 0.90 (s, 9H, C(CH$_3$)$_3$), 0.11 (s, 3H, CH$_3$Si), 0.08 (s, 3H, CH$_3$Si); MSES (M+1):266

Synthesis of Compound 62

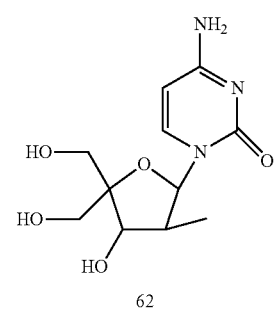

61

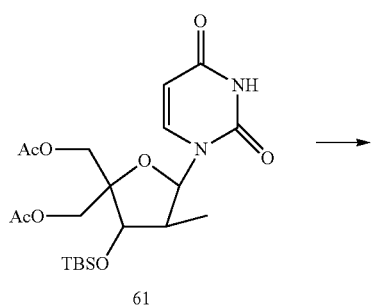

62

To a solution of compound 61 (220 mg, 0.47 mmol) in anhydrous acetonitrile (5 mL) containing triethylamine (0.19 mL, 1.40 mmol) and N-methylpiperidine (0.11 mL, 0.93 mmol) was added TsCl (270 mg, 1.40 mmol) at rt. The resulting mixture was stirred at rt for 1 h and 29% NH$_4$OH aqueous solution was added. Then mixture was stirred at rt for 15 h and concentrated in vacuo. The residue was purified by silica gel column chromatography (MeOH:CH$_2$Cl$_2$=1:40) to give a cytidine intermediate (120 mg, 67%) as a white solid. A mixture of the intermediate (60 mg, 0.156 mmol) and ammonium fluoride (100 mg) in methanol (5 mL) was heated at 90° C. for 15 h and concentrated in vacuo. The residue obtained was purified by silica gel column chromatography (MeOH:CH$_2$Cl$_2$=1:10 to 1:4) to give compound 62 (10 mg, 24%) as a white solid. UV(λ$_{max}$) 273 nm (MeOH); $^1$H NMR (D$_2$O) δ (ppm) 8.08 (d, 1H, J=7.6 Hz, H-6), 6.32 (d, 1H, J=8.4 Hz, H-1'), 6.09 (d, 1H, J=7.6 Hz, H-5), 4.09 (d, 1H, J=10.4 Hz, H-3'), 3.83 (d, 1H, J=12.8 Hz, CH-4'), 3.77 (d, 1H, J=12.4 Hz, CH-4'), 3.72 (d, 1H, J=12.4 Hz, CH-4'), 3.60 (d, 1H, J=12.4 Hz, CH-4'), 2.87 (m, 1H, H-2'), 0.87 (d, 3H, J=6.8 Hz, CH$_3$).

Synthesis of Compound 64

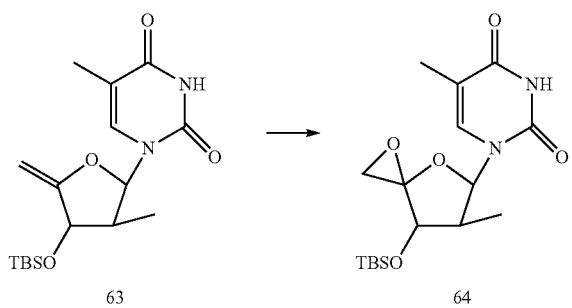 [SMILES: C=C1OC(n2cc(C)c(=O)[nH]c2=O)C(C)C1O[Si](C)(C)C(C)(C)C ; Cc1cn(C2OC3(CO3)C(O[Si](C)(C)C(C)(C)C)C2C)c(=O)[nH]c1=O]

63    64

To a solution of substrate 63 (150 mg, 0.43 mmol) in CH$_2$Cl$_2$ (9 mL) was added cold solution of DMDO (11.33 mL, 1.8 eq, 0.79 mmol, from 0.07 M in acetone) at −30° C. and stirred for 1 h under argon atmosphere. The solvents were evaporated and the residue was dried in vacuo with vigorous stirring at 0° C., and dried for additional 5 min. A viscous solid 64 was formed and used for next step with out purification (~90%).

Synthesis of Compound 67

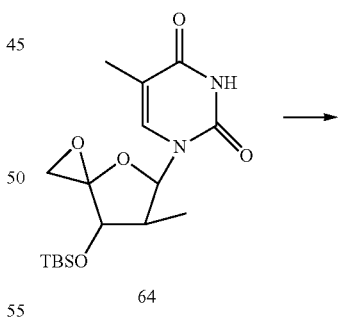

64

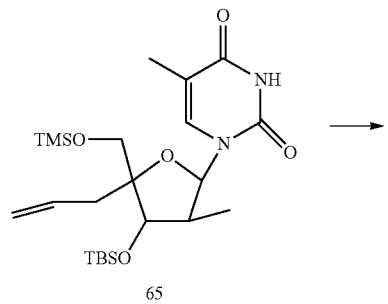

65

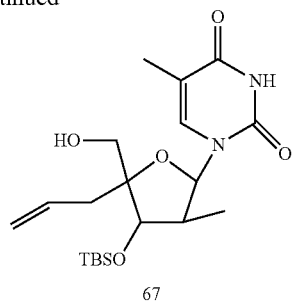

67

To the cold solution of epoxide 64 (150 mg, 0.41 mmol) in CH$_2$Cl$_2$ (10 mL) at −30° C. were added TMS-CH$_2$CH=CH$_2$ (90 mg, 146 uL, 1.22 mmol) followed by SnCl$_4$ (1.22 mL of 1 M solution in CH$_2$Cl$_2$, 1.22 mmol) at once under argon atmosphere. The reaction mixture was stirred at −30° C. for 6 h and at room temperature for 2 h. The reaction was quenched with sat Na$_2$HCO$_3$ solution, the reaction mixture was filtered through a celite pad. The filtrate was partitioned between CH$_2$Cl$_2$/H$_2$O. The organic layer was separated, dried (Na$_2$SO$_4$) and concentrated to dryness. The crude product was treated with NH$_3$/MeOH (5 mL, 7 N) for 15 h at room temperature. The solvent was removed in vacuo. The residue was purified by silica gel chromatography, eluting with 10-40% ethyl acetate/hexane to afford compound 67 as colorless foam (85 mg, 76%). Mass calcd: 410.22. Found: 411.10 (M$^+$+H); $^1$H NMR (CDCl$_3$) δ 8.52 (s, NH), 7.76 (s, H), 6.19 (s, H), 5.89 (m, H), 5.15 (d, H, J=4 Hz), 5.11 (s, H), 4.25 (d, H, J=9.2 Hz), 3.86 (d, H, J=11.2 Hz), 3.53 (dd, H, J=11.6 Hz, 3.2 Hz), 2.28 (m, H), 2.39 (dd, H, J=15.2 Hz, 6.8 Hz), 2.12 (dd, H, J=14.4 Hz, 8.4 Hz), 1.90 (s, 3H), 0.91 (s, 9H) 0.12 (s, 3H), 0.11 (s, 3H).

Synthesis of Compound 69

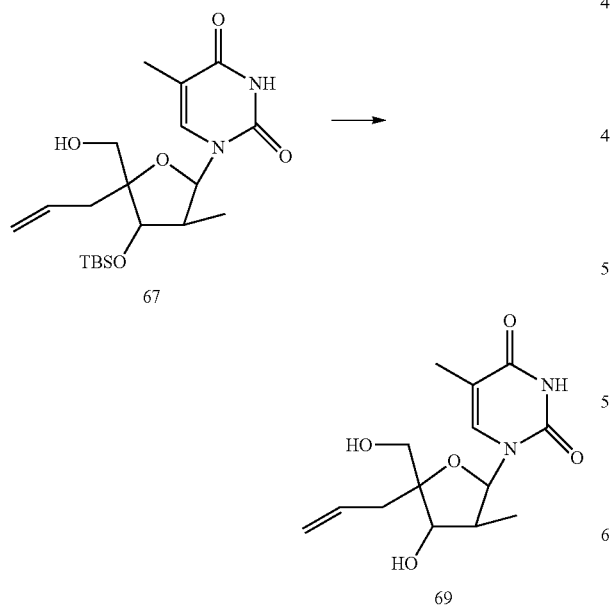

To a well dried mixture of substrate 67 (30 mg, 0.073 mmol), ammonium fluoride (32 mg, 0.73 mmol) was added methanol (3 mL) and refluxed at 85° C. for 12 h. Excess of ammonium fluoride (16 mg, 0.36 mmol) and methanol (2 mL) were added and continued refluxing for additional 24 h. The reaction mixture was filtered through a celite pad and the solvent was removed under reduced pressure. The crude product was purified by silica gel chromatography, eluting with 1-8% MeOH/CH$_2$Cl$_2$ to afford product 69 as colorless solid (19 mg, 88%). Mass calcd: 296.32. Found: 297.20 (M$^+$+H); $^1$H NMR (CDCl$_3$) δ 8.22 (s, H), 6.18 (d, H, J=8.4 Hz), 5.98 (m, H), 5.09 (m, 2H), 4.13 (d, H, J=10.8 Hz), 3.76 (d, H, J=12.4 Hz), 3.55 (d, H, J=12 Hz), 2.66 (m, H), 2.39 (dd, H, J=14.8 Hz, 6.4 Hz), 2.17 (dd, H, J=14.6 Hz, 6.4 Hz), 1.85 (s, 3H), 0.93 (d, 3H, J=6.8 Hz).

Synthesis of Compound 68

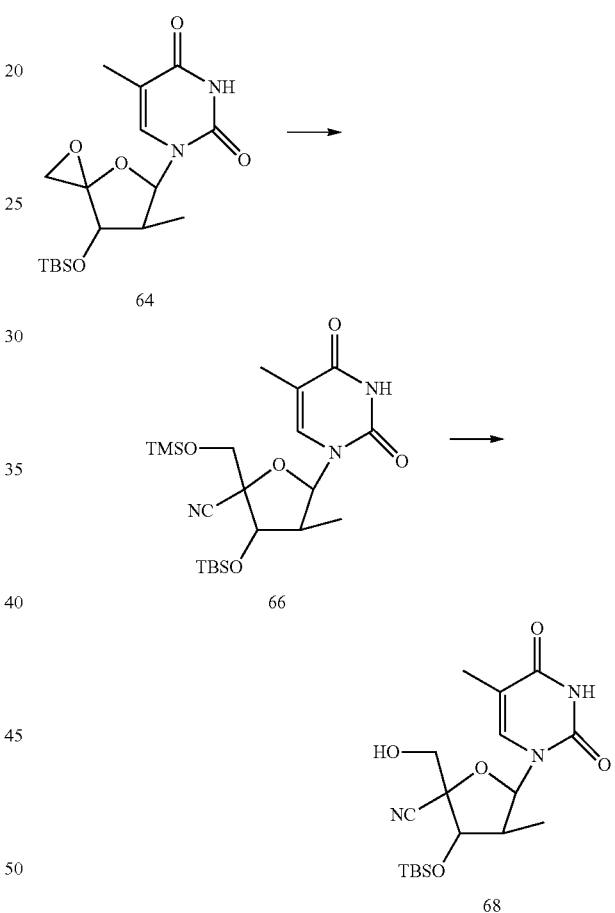

To the cold solution of epoxide 64 (120 mg, 0.33 mmol) in CH$_2$Cl$_2$ (6 mL) at −30° C. was added TMS-CN (60 mg, 0.65 mmol) followed by SnCl$_4$ (0.65 mL, 0.65 mmol from 1 M solution in CH$_2$Cl$_2$) at once under argon atmosphere. The reaction mixture was stirred at −30° C. for 1 h and stirred at room temperature for 15 h. The reaction mixture was quenched with sat Na$_2$HCO$_3$ solution. The reaction mixture was filtered and the filtrate was partitioned between CH$_2$Cl$_2$/H$_2$O. The organic layer was separated, dried (Na$_2$SO$_4$) and concentrated to dryness. The crude product was treated with NH$_3$/MeOH (7N, 5 mL) for 15 h at room temperature. The solvent was removed and the crude product was purified by silica gel chromatography, eluting with 4-30% ethyl acetate/hexane to afford product 68 as colorless solid (72 mg, 56%). Mass calcd: 395.20. Found: 396.30 (M+ +H); $^1$H NMR (CDCl$_3$) δ 8.63 (s, NH), 7.28 (s, H), 6.14 (d, H, J=6.4 Hz), 4.36 (s, H), 4.14 (d, H, J=12 Hz), 3.92 (d, H, J=12.4 Hz), 3.02 (br s, OH), 2.83 (m, H), 1.90 (d, 3H, J=1.2 Hz), 1.02 (d, 3H, J=6.8 Hz), 0.94 (s, 9H), 0.17 (s, 3H), 0.14 (s, 3H).

Synthesis of Compound 70

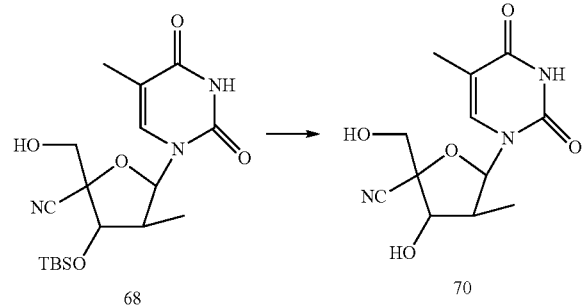 [SMILES: Cc1cn(C2OC(C#N)(CO)C(O[Si](C)(C)C(C)(C)C)C2C)c(=O)[nH]c1=O ; Cc1cn(C2OC(C#N)(CO)C(O)C2C)c(=O)[nH]c1=O]

To a well-dried mixture of substrate 68 (35 mg, 0.09 mmol) and ammonium fluoride (33 mg, 0.73 mmol) was added MeOH (3 mL) and refluxed at 85° C. The reaction completed in 12 h. The solvent was removed and the crude product was dissolved in 20% MeOH/CH$_2$Cl$_2$ solution. The reaction mixture was filtered through a celite pad. The solvent was removed under reduced pressure. The crude product was purified by silica gel chromatography, eluting with 1-8% MeOH/CH$_2$Cl$_2$ to afford product 70 as colorless solid (20 mg, 80%). Mass calcd: 281. 27. Found: 282.20 (M+ +H); $^1$H NMR (CDCl$_3$) δ 7.73 (s, H), 6.34 (d, H, J=6.4 Hz), 4.19 (d, H, J=10.4 Hz), 4.02 (d, H, J=12.4 Hz), 3.92 (d, H, J=12 Hz), 2.73 (m, H), 1.85 (s, 3H), 0.98 (d, 3H, J=6.8 Hz).

Preparation of Triethynyl Aluminum

To a solution of AlCl$_3$ (1 g, 7.5 mmol) in CH$_2$Cl$_2$ (7.5 mL) was added ethynyl magnesium chloride (37.5 mL from 0.6 M, in THF, 22.5 mmol) under Ar at at 0° C. The reaction mixture was warmed to RT and stirred for over night. The resulting dark brown solution (0.14 M) was used for next step.

Synthesis of Compounds 71 and 72

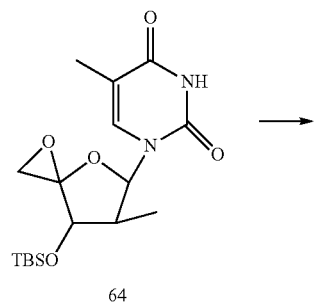

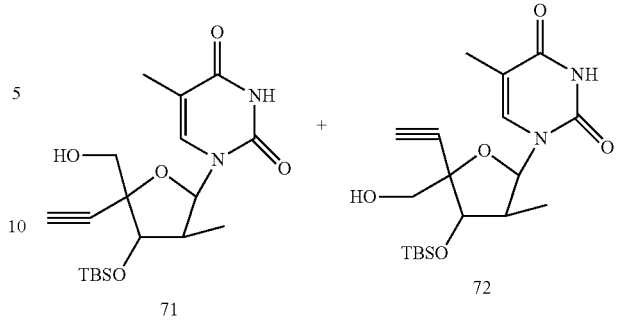

To the cold solution of epoxide 64 (80 mg, 0.22 mmol) in CH$_2$Cl$_2$ (6 mL) at −30° C. was added triethynyl aluminum (5.2 mL from 0.14 M stock solution in CH$_2$Cl$_2$/THF, 0.56 mmol) at once under argon atmosphere and stirred at −30° C. for 6 h. The reaction was quenched with saturated NH$_4$Cl solution and filtered through a celite pad. The filtrate was partitioned between CH$_2$Cl$_2$/H$_2$O. The organic layer was separated and dried (Na$_2$SO$_4$). The solvent was removed and the crude product was purified by silica gel chromatography, eluting with 5-30% ethyl acetate/hexane to afford products 71 and 72 as semi solid (57 mg, over all 67%). Mass calcd: 394.20. Found: 395.40 (M+ +H).

Isomer 71: $^1$H NMR (CDCl$_3$): δ 9.02 (s, NH), 7.58 (s, H), 6.31 (s H), 4.10 (d, H, J=12.0 Hz), 3.99 (d, H, J=12.6 Hz), 3.71 (d, H, J=12.3 Hz), 2.81 (m, H), 1.91 (s, 3H), 1.01 (s, 3H), 0.97 (s, 9H), 0.17 (s, 3H), 0.12 (s, 3H).

Isomer 72: δ 8.34 (s, NH), 7.43 (s, H), 6.33 (d, H, J=7.2 Hz), 4.23 (d, H, J=7.2 Hz), 3.91 (dd, H, J=12.4 Hz, 4.8 Hz), 3.78 (dd, H, J=12.0 Hz, 9.2 Hz), 2.79 (m, H), 1.95 (s, 3H), 0.98 (d, H, J=7.6 Hz), 0.93 (s, 9H), 0.18 (s, 3H), 0.14 (s, 3H).

Synthesis of Compound 73

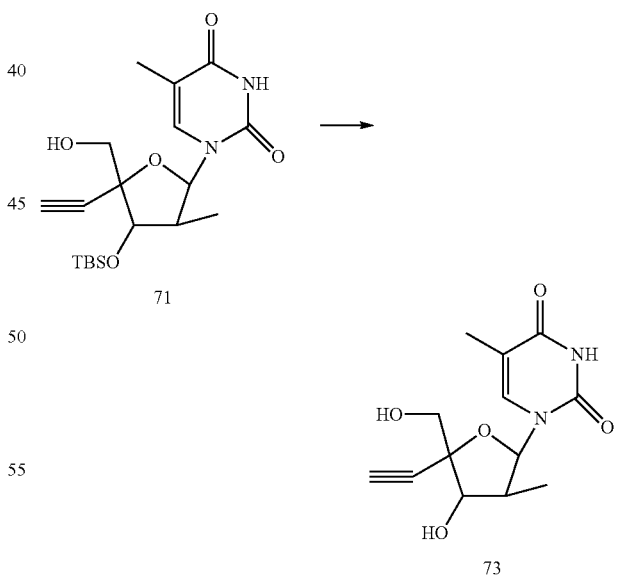

To a well dried mixture of substrate 71 (20 mg, 0.46 mmol) and ammonium fluoride (17 mg, 4.56 mmol) was added MeOH (3 mL) and refluxed at 85° C. Reaction completed in 12 h, the solvent was removed by reduced pressure and the crude product was dissolved in 20% MeOH/CH$_2$Cl$_2$ solution. The reaction mixture was filtered through a celite pad.

The solvent was removed under reduced pressure and the crude product was purified by silica gel chromatography, eluting with 1-8% MeOH/CH$_2$Cl$_2$ to afford product 73 as colorless solid (12 mg, 94%). Mass calcd: 280.30. Found: 281.20 (M$^+$+H); $^1$H NMR (CDCl$_3$) δ 7.94 (s, H), 6.23 (d, H, J=8 Hz), 4.03 (d, H, J=10.8 Hz), 3.90 (d, H, J=12.4 Hz), 3.80 (d, H, J=12.4 Hz), 3.05 (s, H), 2.75 (m, H), 1.85 (d, 3H, J=1.2 Hz), 0.95 (d, 3H, J=7.2 Hz).

Synthesis of Compound 74

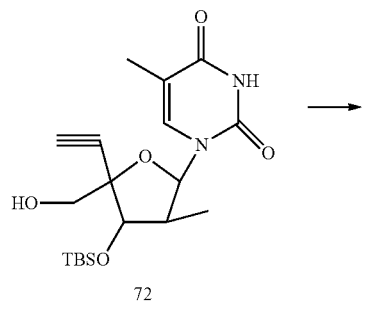

72

To a well-dried mixture of substrate 72 (10 mg, 0.03 mmol) and ammonium fluoride (10 mg, 0.3 mmol) was added MeOH (2 mL) and refluxed at 85° C. The reaction completed in 12 h and the solvent was removed under reduced pressure. The crude product was dissolved in 20% MeOH/CH$_2$Cl$_2$ solution. The reaction mixture was filtered through a celite pad. The solvent was removed and the crude product was purified by silica gel chromatography, eluting with 1-8% MeOH/CH$_2$Cl$_2$ to afford product 74 as colorless solid (8 mg, 91%). Mass calcd: 280.30. Found: 281.2 (M$^+$+H); $^1$H NMR (CDCl$_3$) δ 7.58 (s, H), 6.30 (d, H, J=8.4 Hz), 4.16 (d, H, J=12.2 Hz), 3.89 (d, H, J=12.8 Hz), 3.71 (d, H, J=12.7 Hz), 3.28 (s, H), 2.85 (s, H), 1.90 (d, 3H, J=1.3 Hz), 0.96 (d, 3H, J=7.0).

In a similar manner, but using the appropriate sugar and pyrimidine or purine bases, the following nucleosides of formula as indicated can be prepared.

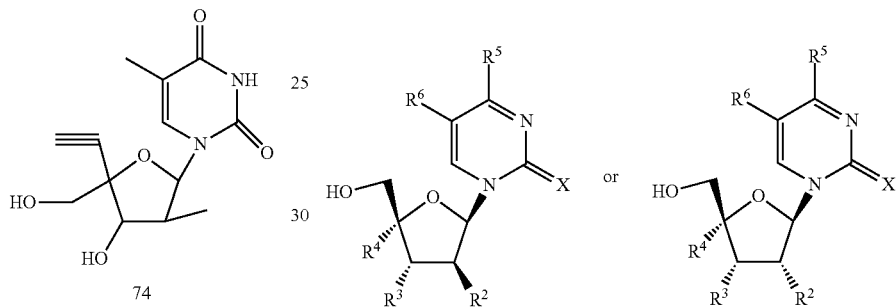

74

| R$^2$ | R$^3$ | R$^4$ | R$^5$ | X | R$^6$ |
|---|---|---|---|---|---|
| CH$_3$ | OH | N$_3$ | NH$_2$, NH—NH$_2$, NH—OH, OH, SH, | O, S | H, CH$_3$, F, Cl, Br, I, NO$_2$, CH═CH$_2$, CH═CHBr, CH═CHCl, C≡CH, CN, NH$_2$, CH$_2$OH |
| CH$_3$ | OH | C≡CH | NH$_2$, NH—NH$_2$, NH—OH, OH, SH, | O, S | H, CH$_3$, F, Cl, Br, I, NO$_2$, CH═CH$_2$, CH═CHBr, CH═CHCl, C≡CH, CN, NH$_2$, CH$_2$OH |
| CH$_3$ | OH | CH═CH$_2$ | NH$_2$, NH—NH$_2$, NH—OH, OH, SH, | O, S | H, CH$_3$, F, Cl, Br, I, NO$_2$, CH═CH$_2$, CH═CHBr, CH═CHCl, C≡CH, CN, NH$_2$, CH$_2$OH |
| CH$_3$ | OH | CN | NH$_2$, NH—NH$_2$, NH—OH, OH, SH, | O, S | H, CH$_3$, F, Cl, Br, I, NO$_2$, CH═CH$_2$, CH═CHBr, CH═CHCl, C≡CH, CN, NH$_2$, CH$_2$OH |
| CH$_3$ | OH | OMe | NH$_2$, NH—NH$_2$, NH—OH, OH, SH, | O, S | H, CH$_3$, F, Cl, Br, I, NO$_2$, CH═CH$_2$, CH═CHBr, CH═CHCl, C≡CH, CN, NH$_2$, CH$_2$OH |
| CH$_3$ | OH | F | NH$_2$, NH—NH$_2$, NH—OH, OH, SH, | O, S | H, CH$_3$, F, Cl, Br, I, NO$_2$, CH═CH$_2$, CH═CHBr, CH═CHCl, C≡CH, CN, NH$_2$, CH$_2$OH |
| CH$_3$ | OH | Me | NH$_2$, NH—NH$_2$, NH—OH, OH, SH, | O, S | H, CH$_3$, F, Cl, Br, I, NO$_2$, CH═CH$_2$, CH═CHBr, CH═CHCl, C≡CH, CN, NH$_2$, CH$_2$OH |
| CH═CH$_2$ | OH | C≡CH | NH$_2$, NH—NH$_2$, NH—OH, OH, SH, | O, S | H, CH$_3$, F, Cl, Br, I, NO$_2$, CH═CH$_2$, CH═CHBr, CH═CHCl, C≡CH, CN, NH$_2$, CH$_2$OH |
| CH═CH$_2$ | OH | CN | NH$_2$, NH—NH$_2$, NH—OH, OH, SH, | O, S | H, CH$_3$, F, Cl, Br, I, NO$_2$, CH═CH$_2$, CH═CHBr, |

| $R^2$ | $R^3$ | $R^4$ | $R^5$ | X | $R^6$ |
|---|---|---|---|---|---|
| | | | | | CH=CHCl, C≡CH, CN, NH₂, CH₂OH |
| CH=CH₂ | OH | F | NH₂, NH—NH₂, NH—OH, OH, SH, | O, S | H, CH₃, F, Cl, Br, I, NO₂, CH=CH₂, CH=CHBr, CH=CHCl, C≡CH, CN, NH₂, CH₂OH |
| CH=CH₂ | OH | Me | NH₂, NH—NH₂, NH—OH, OH, SH, | O, S | H, CH₃, F, Cl, Br, I, NO₂, CH=CH₂, CH=CHBr, CH=CHCl, C≡CH, CN, NH₂, CH₂OH |
| CH=CH₂ | OH | N₃ | NH₂, NH—NH₂, NH—OH, OH, SH, | O, S | H, CH₃, F, Cl, Br, I, NO₂, CH=CH₂, CH=CHBr, CH=CHCl, C≡CH, CN, NH₂, CH₂OH |
| C≡CH | OH | C≡CH | NH₂, NH—NH₂, NH—OH, OH, SH, | O, S | H, CH₃, F, Cl, Br, I, NO₂, CH=CH₂, CH=CHBr, CH=CHCl, C≡CH, CN, NH₂, CH₂OH |
| C≡CH | OH | CN | NH₂, NH—NH₂, NH—OH, OH, SH, | O, S | H, CH₃, F, Cl, Br, I, NO₂, CH=CH₂, CH=CHBr, CH=CHCl, C≡CH, CN, NH₂, CH₂OH |
| C≡CH | OH | N₃ | NH₂, NH—NH₂, NH—OH, OH, SH, | O, S | H, CH₃, F, Cl, Br, I, NO₂, CH=CH₂, CH=CHBr, CH=CHCl, C≡CH, CN, NH₂, CH₂OH |
| C≡CH | OH | OMe | NH₂, NH—NH₂, NH—OH, OH, SH, | O, S | H, CH₃, F, Cl, Br, I, NO₂, CH=CH₂, CH=CHBr, CH=CHCl, C≡CH, CN, NH₂, CH₂OH |
| CH₂F | OH | C≡CH | NH₂, NH—NH₂, NH—OH, OH, SH, | O, S | H, CH₃, F, Cl, Br, I, NO₂, CH=CH₂, CH=CHBr, CH=CHCl, C≡CH, CN, NH₂, CH₂OH |
| CH₂F | OH | CN | NH₂, NH—NH₂, NH—OH, OH, SH, | O, S | H, CH₃, F, Cl, Br, I, NO₂, CH=CH₂, CH=CHBr, CH=CHCl, C≡CH, CN, NH₂, CH₂OH |
| CH₂F | OH | N₃ | NH₂, NH—NH₂, NH—OH, OH, SH, | O, S | H, CH₃, F, Cl, Br, I, NO₂, CH=CH₂, CH=CHBr, CH=CHCl, C≡CH, CN, NH₂, CH₂OH |
| CH₂F | OH | CH=CH₂ | NH₂, NH—NH₂, NH—OH, OH, SH, | O, S | H, CH₃, F, Cl, Br, I, NO₂, CH=CH₂, CH=CHBr, CH=CHCl, C≡CH, CN, NH₂, CH₂OH |
| CN | OH | C≡CH | NH₂, NH—NH₂, NH—OH, OH, SH, | O, S | H, CH₃, F, Cl, Br, I, NO₂, CH=CH₂, CH=CHBr, CH=CHCl, C≡CH, CN, NH₂, CH₂OH |
| CN | OH | CN | NH₂, NH—NH₂, NH—OH, OH, SH, | O, S | H, CH₃, F, Cl, Br, I, NO₂, CH=CH₂, CH=CHBr, CH=CHCl, C≡CH, CN, NH₂, CH₂OH |
| CN | OH | N₃ | NH₂, NH—NH₂, NH—OH, OH, SH, | O, S | H, CH₃, F, Cl, Br, I, NO₂, CH=CH₂, CH=CHBr, CH=CHCl, C≡CH, CN, NH₂, CH₂OH |
| CN | OH | CH=CH₂ | NH₂, NH—NH₂, NH—OH, OH, SH, | O, S | H, CH₃, F, Cl, Br, I, NO₂, CH=CH₂, CH=CHBr, CH=CHCl, C≡CH, CN, NH₂, CH₂OH |
| CH₂CH₃ | OH | N₃ | NH₂, NH—NH₂, NH—OH, OH, SH, | O, S | H, CH₃, F, Cl, Br, I, NO₂, CH=CH₂, CH=CHBr, CH=CHCl, C≡CH, CN, NH₂, CH₂OH |
| CF₃ | OH | N₃ | NH₂, NH—NH₂, NH—OH, OH, SH, | O, S | H, CH₃, F, Cl, Br, I, NO₂, CH=CH₂, CH=CHBr, CH=CHCl, C≡CH, CN, NH₂, CH₂OH |

109

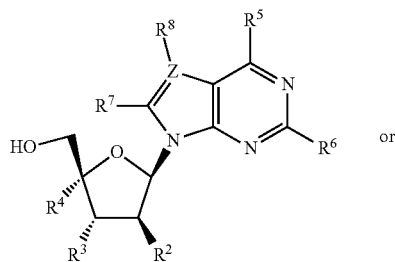

or

110

-continued

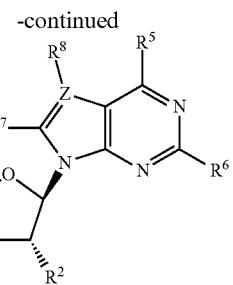

| R² | R³ | R⁴ | R⁶ | R⁵ | Z | R⁸ | R⁷ |
|---|---|---|---|---|---|---|---|
| CH₃ | OH | N₃ | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₃ | OH | N₃ | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CH₃ | OH | N₃ | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₃ | OH | N₃ | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CH₃ | OH | C≡CH | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₃ | OH | C≡CH | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CH₃ | OH | C≡CH | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₃ | OH | C≡CH | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CH₃ | OH | CH=CH₂ | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |

-continued

| R² | R³ | R⁴ | R⁶ | R⁵ | Z | R⁸ | R⁷ |
|---|---|---|---|---|---|---|---|
| CH₃ | OH | CH=CH₂ | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CH₃ | OH | CH=CH₂ | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₃ | OH | CH=CH₂ | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CH₃ | OH | CN | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₃ | OH | CN | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CH₃ | OH | CN | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₃ | OH | CN | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CH₃ | OH | OMe | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₃ | OH | OMe | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CH₃ | OH | OMe | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₃ | OH | OMe | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |

-continued

| R² | R³ | R⁴ | R⁶ | R⁵ | Z | R⁸ | R⁷ |
|---|---|---|---|---|---|---|---|
| CH₃ | OH | F | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₃ | OH | F | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CH₃ | OH | F | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₃ | OH | F | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CH₃ | OH | Me | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₃ | OH | Me | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CH₃ | OH | Me | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH₃ | OH | Me | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CH=CH₂ | OH | C≡CH | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | N | — | H |
| CH=CH₂ | OH | C≡CH | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |
| CH=CH₂ | OH | C≡CH | NH₂ | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | N | — | H |

-continued

| R² | R³ | R⁴ | R⁶ | R⁵ | Z | R⁸ | R⁷ |
|---|---|---|---|---|---|---|---|
| CH=CH₂ | OH | C≡CH | NH₂ | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | C | H, F, Cl, Br, I, NO₂, CH=CH₂, C≡CH, CN, COOH, CONH₂, COOMe | H |
| CH=CH₂ | OH | CN | H | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | N | — | H |
| CH=CH₂ | OH | CN | H | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | C | H, F, Cl, Br, I, NO₂, CH=CH₂, C≡CH, CN, COOH, COOMe | H |
| CH=CH₂ | OH | CN | NH₂ | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | N | — | H |
| CH=CH₂ | OH | CN | NH₂ | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | C | H, F, Cl, Br, I, NO₂, CH=CH₂, C≡CH, CN, COOH, CONH₂, COOMe | H |
| CH=CH₂ | OH | F | H | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | N | — | H |
| CH=CH₂ | OH | F | H | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | C | H, F, Cl, Br, I, NO₂, CH=CH₂, C≡CH, CN, COOH, CONH₂, COOMe | H |
| CH=CH₂ | OH | F | NH₂ | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | N | — | H |
| CH=CH₂ | OH | F | NH₂ | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | C | H, F, Cl, Br, I, NO₂, CH=CH₂, C≡CH, CN, COOH, CONH₂, COOMe | H |
| CH=CH₂ | OH | Me | H | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | N | — | H |
| CH=CH₂ | OH | Me | H | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | C | H, F, Cl, Br, I, NO₂, CH=CH₂, C≡CH, CN, COOH, CONH₂, COOMe | H |

-continued

| $R^2$ | $R^3$ | $R^4$ | $R^6$ | $R^5$ | Z | $R^8$ | $R^7$ |
|---|---|---|---|---|---|---|---|
| CH=CH$_2$ | OH | Me | NH$_2$ | F, Cl, Br, I, OH, OMe, OEt, OBn, SH, SMe, SEt, O-acetyl NH$_2$, NH—Me, NH—Et, NH-propyl, heterocycle, NH-cyclopropyl, NH-acetyl, NH-cyclobutyl, NH-t-butyl, Azetidine, N,N—Me$_2$, N,N—Et$_2$, | N | — | H |
| CH=CH$_2$ | OH | Me | NH$_2$ | F, Cl, Br, I, OH, OMe, OEt, OBn, SH, SMe, SEt, O-acetyl NH$_2$, NH—Me, NH—Et, NH-propyl, heterocycle, NH-cyclopropyl, NH-acetyl, NH-cyclobutyl, NH-t-butyl, Azetidine, N,N—Me$_2$, N,N—Et$_2$, | C | H, F, Cl, Br, I, NO$_2$, CH=CH$_2$, C≡CH, CN, COOH, CONH$_2$, COOMe | H |
| CH=CH$_2$ | OH | N$_3$ | H | F, Cl, Br, I, OH, OMe, OEt, OBn, SH, SMe, SEt, O-acetyl NH$_2$, NH—Me, NH—Et, NH-propyl, heterocycle, NH-cyclopropyl, NH-acetyl, NH-cyclobutyl, NH-t-butyl, Azetidine, N,N—Me$_2$, N,N—Et$_2$, | N | — | H |
| CH=CH$_2$ | OH | N$_3$ | H | F, Cl, Br, I, OH, OMe, OEt, OBn, SH, SMe, SEt, O-acetyl NH$_2$, NH—Me, NH—Et, NH-propyl, heterocycle, NH-cyclopropyl, NH-acetyl, NH-cyclobutyl, NH-t-butyl, Azetidine, N,N—Me$_2$, N,N—Et$_2$, | C | H, F, Cl, Br, I, NO$_2$, CH=CH$_2$, C≡CH, CN, COOH, CONH$_2$, COOMe | H |
| CH=CH$_2$ | OH | N$_3$ | NH$_2$ | F, Cl, Br, I, OH, OMe, OEt, OBn, SH, SMe, SEt, O-acetyl NH$_2$, NH—Me, NH—Et, NH-propyl, heterocycle, NH-cyclopropyl, NH-acetyl, NH-cyclobutyl, NH-t-butyl, Azetidine, N,N—Me$_2$, N,N—Et$_2$, | N | — | H |
| CH=CH$_2$ | OH | N$_3$ | NH$_2$ | F, Cl, Br, I, OH, OMe, OEt, OBn, SH, SMe, SEt, O-acetyl NH$_2$, NH—Me, NH—Et, NH-propyl, heterocycle, NH-cyclopropyl, NH-acetyl, NH-cyclobutyl, NH-t-butyl, Azetidine, N,N—Me$_2$, N,N—Et$_2$, | C | H, F, Cl, Br, I, NO$_2$, CH=CH$_2$, C≡CH, CN, COOH, CONH$_2$, COOMe | H |
| C≡CH | OH | C≡CH | H | F, Cl, Br, I, OH, OMe, OEt, OBn, SH, SMe, SEt, O-acetyl NH$_2$, NH—Me, NH—Et, NH-propyl, heterocycle, NH-cyclopropyl, NH-acetyl, NH-cyclobutyl, NH-t-butyl, Azetidine, N,N—Me$_2$, N,N—Et$_2$, | N | — | H |
| C≡CH | OH | C≡CH | H | F, Cl, Br, I, OH, OMe, OEt, OBn, SH, SMe, SEt, O-acetyl NH$_2$, NH—Me, NH—Et, NH-propyl, heterocycle, NH-cyclopropyl, NH-acetyl, NH-cyclobutyl, NH-t-butyl, Azetidine, N,N—Me$_2$, N,N—Et$_2$, | C | H, F, Cl, Br, I, NO$_2$, CH=CH$_2$, C≡CH, CN, COOH, CONH$_2$, COOMe | H |
| C≡CH | OH | C≡CH | NH$_2$ | F, Cl, Br, I, OH, OMe, OEt, OBn, SH, SMe, SEt, O-acetyl NH$_2$, NH—Me, NH—Et, NH-propyl, heterocycle, NH-cyclopropyl, NH-acetyl, NH-cyclobutyl, NH-t-butyl, Azetidine, N,N—Me$_2$, N,N—Et$_2$, | N | — | H |
| C≡CH | OH | C≡CH | NH$_2$ | F, Cl, Br, I, OH, OMe, OEt, OBn, SH, SMe, SEt, O-acetyl NH$_2$, NH—Me, NH—Et, NH-propyl, heterocycle, NH-cyclopropyl, NH-acetyl, NH-cyclobutyl, NH-t-butyl, Azetidine, N,N—Me$_2$, N,N—Et$_2$, | C | H, F, Cl, Br, I, NO$_2$, CH=CH$_2$, C≡CH, CN, COOH, CONH$_2$, COOMe | H |
| C≡CH | OH | CN | H | NH$_2$, NH—Me, NH—Et, NH-propyl, heterocycle, NH-cyclopropyl, NH-acetyl, NH-cyclobutyl, NH-t-butyl, Azetidine, N,N—Me$_2$, N,N—Et$_2$, | N | — | H |

| R² | R³ | R⁴ | R⁶ | R⁵ | Z | R⁸ | R⁷ |
|---|---|---|---|---|---|---|---|
| C≡CH | OH | CN | H | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | C | H, F, Cl, Br, I, NO₂, CH=CH₂, C≡CH, CN, COOH, CONH₂, COOMe | H |
| C≡CH | OH | CN | NH₂ | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | N | — | H |
| C≡CH | OH | CN | NH₂ | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | C | H, F, Cl, Br, I, NO₂, CH=CH₂, C≡CH, CN, COOH, CONH₂, COOMe | H |
| C≡CH | OH | N₃ | H | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | N | — | H |
| C≡CH | OH | N₃ | H | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | C | H, F, Cl, Br, I, NO₂, CH=CH₂, C≡CH, CN, COOH, CONH₂, COOMe | H |
| C≡CH | OH | N₃ | NH₂ | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | N | — | H |
| C≡CH | OH | N₃ | NH₂ | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | C | H, F, Cl, Br, I, NO₂, CH=CH₂, C≡CH, CN, COOH, CONH₂, COOMe | H |
| C≡CH | OH | OMe | H | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | N | — | H |
| C≡CH | OH | OMe | H | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | C | H, F, Cl, Br, I, NO₂, CH=CH₂, C≡CH, CN, COOH, CONH₂, COOMe | H |
| C≡CH | OH | OMe | NH₂ | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | N | — | H |
| C≡CH | OH | OMe | NH₂ | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | C | H, F, Cl, Br, I, NO₂, CH=CH₂, C≡CH, CN, COOH, CONH₂, COOMe | H |

-continued

| $R^2$ | $R^3$ | $R^4$ | $R^6$ | $R^5$ | Z | $R^8$ | $R^7$ |
|---|---|---|---|---|---|---|---|
| $CH_2F$ | OH | C≡CH | H | F, Cl, Br, I, OH, OMe, OEt, OBn, SH, SMe, SEt, O-acetyl $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, | N | — | H |
| $CH_2F$ | OH | C≡CH | H | F, Cl, Br, I, OH, OMe, OEt, OBn, SH, SMe, SEt, O-acetyl $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, | C | H, F, Cl, Br, I, $NO_2$, $CH=CH_2$, C≡CH, CN, COOH, $CONH_2$, COOMe | H |
| $CH_2F$ | OH | C≡CH | $NH_2$ | F, Cl, Br, I, OH, OMe, OEt, OBn, SH, SMe, SEt, O-acetyl $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, | N | — | H |
| $CH_2F$ | OH | C≡CH | $NH_2$ | F, Cl, Br, I, OH, OMe, OEt, OBn, SH, SMe, SEt, O-acetyl $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, | C | H, F, Cl, Br, I, $NO_2$, $CH=CH_2$, C≡CH, CN, COOH, $CONH_2$, COOMe | H |
| $CH_2F$ | OH | CN | H | F, Cl, Br, I, OH, OMe, OEt, OBn, SH, SMe, SEt, O-acetyl $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, | N | — | H |
| $CH_2F$ | OH | CN | H | F, Cl, Br, I, OH, OMe, OEt, OBn, SH, SMe, SEt, O-acetyl $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, | C | H, F, Cl, Br, I, $NO_2$, $CH=CH_2$, C≡CH, CN, COOH, $CONH_2$, COOMe | H |
| $CH_2F$ | OH | CN | $NH_2$ | F, Cl, Br, I, OH, OMe, OEt, OBn, SH, SMe, SEt, O-acetyl $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, | N | — | H |
| $CH_2F$ | OH | CN | $NH_2$ | F, Cl, Br, I, OH, OMe, OEt, OBn, SH, SMe, SEt, O-acetyl $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, | C | H, F, Cl, Br, I, $NO_2$, $CH=CH_2$, C≡CH, CN, COOH, $CONH_2$, COOMe | H |
| $CH_2F$ | OH | $N_3$ | H | F, Cl, Br, I, OH, OMe, OEt, OBn, SH, SMe, SEt, O-acetyl $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, | N | — | H |
| $CH_2F$ | OH | $N_3$ | H | F, Cl, Br, I, OH, OMe, OEt, OBn, SH, SMe, SEt, O-acetyl $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, | C | H, F, Cl, Br, I, $NO_2$, $CH=CH_2$, C≡CH, CN, COOH, $CONH_2$, COOMe | H |
| $CH_2F$ | OH | $N_3$ | $NH_2$ | $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, | N | — | H |

-continued

| $R^2$ | $R^3$ | $R^4$ | $R^6$ | $R^5$ | Z | $R^8$ | $R^7$ |
|---|---|---|---|---|---|---|---|
| $CH_2F$ | OH | $N_3$ | $NH_2$ | F, Cl, Br, I, OH, OMe, OEt, OBn, SH, SMe, SEt, O-acetyl $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, | C | H, F, Cl, Br, I, $NO_2$, $CH=CH_2$, $C\equiv CH$, CN, COOH, $CONH_2$, COOMe | H |
| $CH_2F$ | OH | $CH=CH_2$ | H | F, Cl, Br, I, OH, OMe, OEt, OBn, SH, SMe, SEt, O-acetyl $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, | N | — | H |
| $CH_2F$ | OH | $CH=CH_2$ | H | F, Cl, Br, I, OH, OMe, OEt, OBn, SH, SMe, SEt, O-acetyl $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, | C | H, F, Cl, Br, I, $NO_2$, $CH=CH_2$, $C\equiv CH$, CN, COOH, $CONH_2$, COOMe | H |
| $CH_2F$ | OH | $CH=CH_2$ | $NH_2$ | F, Cl, Br, I, OH, OMe, OEt, OBn, SH, SMe, SEt, O-acetyl $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, | N | — | H |
| $CH_2F$ | OH | $CH=CH_2$ | $NH_2$ | F, Cl, Br, I, OH, OMe, OEt, OBn, SH, SMe, SEt, O-acetyl $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, | C | H, F, Cl, Br, I, $NO_2$, $CH=CH_2$, $C\equiv CH$, CN, COOH, $CONH_2$, COOMe | H |
| CN | OH | $C\equiv CH$ | H | F, Cl, Br, I, OH, OMe, OEt, OBn, SH, SMe, SEt, O-acetyl $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, | N | — | H |
| CN | OH | $C\equiv CH$ | H | F, Cl, Br, I, OH, OMe, OEt, OBn, SH, SMe, SEt, O-acetyl $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, | C | H, F, Cl, Br, I, $NO_2$, $CH=CH_2$, $C\equiv CH$, CN, COOH, $CONH_2$, COOMe | H |
| CN | OH | $C\equiv CH$ | $NH_2$ | F, Cl, Br, I, OH, OMe, OEt, OBn, SH, SMe, SEt, O-acetyl $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, | N | — | H |
| CN | OH | $C\equiv CH$ | $NH_2$ | F, Cl, Br, I, OH, OMe, OEt, OBn, SH, SMe, SEt, O-acetyl $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, | C | H, F, Cl, Br, I, $NO_2$, $CH=CH_2$, $C\equiv CH$, CN, COOH, $CONH_2$, COOMe | H |
| CN | OH | CN | H | F, Cl, Br, I, OH, OMe, OEt, OBn, SH, SMe, SEt, O-acetyl $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, | N | — | H |
| CN | OH | CN | H | F, Cl, Br, I, OH, OMe, OEt, OBn, SH, SMe, SEt, O-acetyl $NH_2$, NH—Me, NH—Et, NH-propyl, heterocycle, NH-cyclopropyl, NH-acetyl, NH-cyclobutyl, NH-t-butyl, Azetidine, N,N—$Me_2$, N,N—$Et_2$, | C | H, F, Cl, Br, I, $NO_2$, $CH=CH_2$, $C\equiv CH$, CN, COOH, $CONH_2$, COOMe | H |

-continued

| R² | R³ | R⁴ | R⁶ | R⁵ | Z | R⁸ | R⁷ |
|---|---|---|---|---|---|---|---|
| CN | OH | CN | NH₂ | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | N | — | H |
| CN | OH | CN | NH₂ | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | C | H, F, Cl, Br, I, NO₂, CH=CH₂, C≡CH, CN, COOH, CONH₂, COOMe | H |
| CN | OH | N₃ | H | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | N | — | H |
| CN | OH | N₃ | H | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | C | H, F, Cl, Br, I, NO₂, CH=CH₂, C≡CH, CN, COOH, CONH₂, COOMe | H |
| CN | OH | N₃ | NH₂ | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | N | — | H |
| CN | OH | N₃ | NH₂ | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | C | H, F, Cl, Br, I, NO₂, CH=CH₂, C≡CH, CN, COOH, CONH₂, COOMe | H |
| CN | OH | CH=CH₂ | H | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | N | — | H |
| CN | OH | CH=CH₂ | H | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | C | H, F, Cl, Br, I, NO₂, CH=CH₂, C≡CH, CN, COOH, CONH₂, COOMe | H |
| CN | OH | CH=CH₂ | NH₂ | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | N | — | H |
| CN | OH | CH=CH₂ | NH₂ | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | C | H, F, Cl, Br, I, NO₂, CH=CH₂, C≡CH, CN, COOH, CONH₂, COOMe | H |
| CH₂CH₃ | OH | N₃ | H | NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | N | — | H |

-continued

| R² | R³ | R⁴ | R⁶ | R⁵ | Z | R⁸ | R⁷ |
|---|---|---|---|---|---|---|---|
| CH₂CH₃ | OH | N₃ | H | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | C | H, F, Cl, Br, I, NO₂, CH=CH₂, C≡CH, CN, COOH, CONH₂, COOMe | H |
| CH₂CH₃ | OH | N₃ | NH₂ | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | N | — | H |
| CH₂CH₃ | OH | N₃ | NH₂ | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | C | H, F, Cl, Br, I, NO₂, CH=CH₂, C≡CH, CN, COOH, CONH₂, COOMe | H |
| CF₃ | OH | N₃ | H | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | N | — | H |
| CF₃ | OH | N₃ | H | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | C | H, F, Cl, Br, I, NO₂, CH=CH₂, C≡CH, CN, COOH, CONH₂, COOMe | H |
| CF₃ | OH | N₃ | NH₂ | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, | N | — | H |
| CF₃ | OH | N₃ | NH₂ | F, Cl, Br, I, OH, OMe, OEt, OBn, SH, SMe, SEt, O-acetyl NH₂, NH—Me, NH—Et, NH-propyl, heterocycle, NH-cyclopropyl, NH-acetyl, NH-cyclobutyl, NH-t-butyl, Azetidine, N,N—Me₂, N,N—Et₂, F, Cl, Br, I, OH, OMe, OEt, OBn, SH, SMe, SEt, O-acetyl | C | H, F, Cl, Br, I, NO₂, CH=CH₂, C≡CH, CN, COOH, CONH₂, COOMe | H |

Biological Assays

HBV AD38 Assay

The materials required for the assay comprise the following:
The HepG2-AD38 cell line.
The culture medium for HepG2-AD38 comprises DMEM-F/12, 10% fetal bovine serum, 100 IU/ml/100 ug/ml of Penicillin/streptomycin, 50 µg/ml kanamycin, 0.3 µg/ml tetracycline, and 200 µg/ml G418.
The assay medium for HepG2-AD38 comprises DMEM-F/12, 10% fetal bovine serum, 100 IU/ml/100 µg/ml of penicillin/streptomycin, 50 µg/ml kanamycin, and 200 µg/ml G418
Further materials comprise Phosphate buffered saline (PBS), Biocoated 96 well plates, DNeasy 96 tissue kit (Qiagen), QIAvac 96 vacuum manifold, Micro amp optical 96 well reaction plates (Applied Biosystems), Micro amp optical caps (Applied Biosystems), Taqman Universal PCR Master Mix (Applied Biosystems), and a 7700 Sequence detector (Applied Biosystems), The primers and probes for HBV DNA comprise the 1125 nM forward primer (GGA CCC CTG CTC GTG TTA CA), the 1125 nM reverse primer (GAG AGA AGT CCA CCA CGA GTC TAG A), and the 250 nM probe (FAM-TGT TGA CAA GAA TCC TCA CAA TAC CAC).

HBV Cell Assay:

Seed 5×10⁴ cells/well in 200 µl of culture medium in a 96 well biocoated plate and incubate the plate at 37° C. with 5% CO₂. After 2 days, remove carefully the supernatant, wash the cell layer with 200 µl of PBS and renew with 200 µl of assay medium with or without test compounds at 10 µM or in dose response with ratio 1:3 starting at 10 µM (all samples should be tested in duplicate). Let cells grow for 5 more days. At day 7, collect 180 µl of the supernatant per well in a blue rack (included in the DNeasy 96 tissue kit). Store at −80° C. or directly go to next step.

Extraction of Viral HBV DNA from Cell Supernatant:

Thaw the samples in the blue rack. Prepare a Proteinase K/Buffer ATL working solution (2 ml of Proteinase K+18 ml Buffer ATL) and transfer 180 ul on the top of the supernatant in each tube of the blue rack. Seal the tubes properly using the caps provided and mix by inverting the rack upside down a few times. Centrifuge up to 3000 rpm to collect any solution from the caps. Incubate at 55° C. for 15 minutes. Centrifuge up to 3000 rpm again. Carefully remove the caps and add 410 ul of Buffer AL/E to each sample. Seal the tubes using new caps, shake the rack vigorously up and down for 15 seconds and centrifuge up to 3000 rpm. Place the DNeasy 96 plate on top of QIAvac 96 vacuum manifold. Transfer the supernatant from step 8 to the DNeasy 96 plate. Apply the vacuum for a few seconds. Carefully add 500 µl of Buffer AW1 to each well. Apply the vacuum for about 1 minute. Carefully add 500 µl of Buffer AW2 to each well. Apply the vacuum for about 1 minute, flick the plate in the sink, strike the bottom side of the DNeasy 96 plate on a stack of paper towels, apply the vacuum again for 10 minutes. Heat up 10 ml of Buffer AE for a few minutes at 70° C. Place the DNeasy 96 plate on top of a rack of elution microtubes RS. To elute the DNA, add 100 µl of preheated Buffer AE to each well, apply the vacuum for 1 minute.

HBV Real Time PCR:

Prepare the HBV primers+probe mix for 200 wells (total 1500 µl) comprising 45 µl of primer 1 (100 µM), 45 µl of primer 2 (100 µM), 20 µl of probe (50 µM), and 1390 µl of nuclease free water. Select an optical 96 well reaction plate. Make the reaction mix for 100 wells comprising 1000 µl of Universal PCR Master Mix, 750 ul of HBV primers+probe mix, and 250 µl of nuclease free water. Aliquot 20 µl of the reaction mix per well. Add 5 µl per well of HBV DNA from each sample. Cover the wells with optical caps. Centrifuge for a few seconds to force all the reagents to the bottom and to eliminate the bubbles. Place the plate in the 7700 Sequence detector. Select the reporter for FAM and the volume setting for 25 µl. Start the machine and let it go 1 hour and 56 minutes. Calculate the dCt and the reduction in viral load for each test compound.

HCV Replicon Assay

HCV replicon RNA-containing Huh 7 cells (clone A cells; Apath, LLC, St. Louis, Mo.) were kept at exponential growth in Dulbecco's modified Eagle's medium (high glucose) containing 10% fetal bovine serum, 4 mM L-glutamine and 1 mM sodium pyruvate, 1× nonessential amino acids, and G418 (1,000 µg/ml). Antiviral assays were performed in the same medium without G418. Cells were seeded in a 96-well plate at 1,500 cells per well, and test compounds were added immediately after seeding. Incubation time 4 days. At the end of the incubation step, total cellular RNA was isolated (RNeasy 96 kit; Qiagen). Replicon RNA and an internal control (TaqMan rRNA control reagents; Applied Biosystems) were amplified in a single-step multiplex RT-PCR protocol as recommended by the manufacturer. The HCV primers and probe were designed with Primer Express software (Applied Biosystems) and covered highly conserved 5'-untranslated region (UTR) sequences (sense, 5'-AGCCATGGCGTTAGTA(T)GAGTGT-3', and antisense, 5'-TTCCGCAGACCAC-TATGG-3'; probe, 5'-FAM-CCTCCAGGAC-CCCCCCTCCC-TAMRA-3').

To express the antiviral effectiveness of a compound, the threshold RT-PCR cycle of the test compound was subtracted from the average threshold RT-PCR cycle of the no-drug control (ΔCtHCV). A ΔCt of 3.3 equals a 1-log 10 reduction (equal to the 90% effective concentration [$EC_{90}$]) in replicon RNA levels. The cytotoxicity of the test compound could also be expressed by calculating the ΔCtrRNA values. The ΔΔCt specificity parameter could then be introduced (ΔCtHCV−ΔCtrRNA), in which the levels of HCV RNA are normalized for the rRNA levels and calibrated against the no-drug control.

HIV Activity

HIV screen: Primary Screening of PSI compounds are tested for antiviral HIV activity at 50 µM. The cells used are P4CCR5luc cells; they are human HIV indicator cells, which are derived from Hela cells, express CD4, CXCR4, CCR5, luciferase, and a beta-gal gene under the control of HIV-1 LTR. P4CCR5 luc cells are cultivated in DMEM, 10% FBS, Penicillin, Streptomycin, and G418 at 500 µg/ml. 100 µl of P4 CCR5-luc cells are plated at 10,000 cells per well in 96 well Opaque Assay plates and incubated overnight at 37° C. The next day, the media is aspirated from the plates and replaced by 100 µl of compound freshly diluted into media at 2×50 uM, in triplicate, for 4 hours at 37° C. The cells are then infected with 100 ul NL43 virus at 5 ng of p24 per well, in the presence of 2×20 ug/ml of DEAE-Dextran for 40-42 hours. Non infected, infected no drug and AZT controls are always present in triplicate on each plate. After infection the beta-gal is quantitated using the Galacto-Star kit from Applied Biosystems using the manufacturer instructions and the luminescence measured using a Victor apparatus from Perkin-Elmer. Results are represented as percentage inhibition compare to untreated cells. The assays are performed in 2 to 3 independent experiments.

HIV-Titration of PSI Activity to Determine $EC_{50}$ on P4 CCR-Luc Cells.

P4 CCR5-luc cells are plated at 10,000 cells per well (100 µl) in 96 well Opaque Assay plates and incubated overnight at 37° C. The next day, the media is aspirated from the plates and replaced by 100 ul of compound freshly diluted into appropriate media (DMEM, 10% FBS, G418 500 µg/ml, penicillin/streptomycin) at 2× final concentrations in 5 fold dilutions, usually from 2×100 µM to 2×0.032 uM, in triplicate, for 4 hours at 37° C. The cells are then infected with 100 ul NL43 wild type or mutant virus, at 5 ng to 20 ng of p24 per well, in the presence of 2×20 ug/ml of DEAE-Dextran, for 40-42 hours. Non infected and infected no drug controls are always present in 12plicate on each plate. An AZT control is tested in parallel for each experiment. After infection, the beta-gal is quantitated in the cell lysate using the Galacto-Star kit from Applied Biosystems and the luminescence measured using a Victor apparatus from Perkin-Elmer. The $EC_{50}$ (Effective Concentration) is calculated using a Microsoft® Excel® spreadsheet that calculates the concentration necessary to inhibit the 50% of the infection. The assay is performed in at least 2 independent experiments.

Toxicity

Luciferase Assay

P4 CCR5-luc cells are plated at 10,000 cells per well (100 ul) in 96 well Opaque Assay plates and incubated overnight at 37° C. The next day, the media is aspirated from the plates and replaced by 200 ul of compound freshly diluted into media in 5 fold dilutions from 100 µM to 0.0062 µM. After 4 days of incubation at 37° C., the luciferase activity is measured in the cell lysate using the Bright Glow kit from Promega and the luminescence measured using a Victor apparatus from Perkin-Elmer.

MTS Assays

Human cells lines Huh 7 and HepG2 (liver), BxPC3 (pancreatic) and CEM (lymphoid) are used for the MTS assays in 96 wells plates. Drugs are freshly diluted in media at 2×100 µM, 50 µM, 25 µM, 10 µM, 5 µM, 1 µM and 50 µl is dispensed in triplicate in the plates. The wells at the periphery of the plate contain 100 ul of media only and will be the blank controls. A replicate control with no drug is always performed in each plate. 50 µl of cells are added to the plate, at 2000 cells per well for Huh 7, HepG2 and PxPC3, and 5000 cells per well for CEM cells. No cells are added at the periphery of the plate. The media used for Huh 7, HepG2 and BxPC3 cells is DMEM with 10% FBS, and Penicillin/streptomycin, and RPMI with 10% FBS, and Penicillin/streptomycin for CEM cells. After 8 days of incubation at 37° C., 20 µl of MTS dye from the CellTiter 96 Aqueous One Solution Cell Proliferation Assay kit from Promega is added to each well and the plate incubated for 2 h at 37° C. The absorbance is then read at 490 nm using the microplate reader E1800 from Biotek. The signal is calculated by subtracting the absorbance measured in the blank controls. The $CC_{50}$ (Cytotoxic Concentration) value is then determined by comparing the signal obtained with the no-drug cell control with the treated cells and calculating the concentration of drug necessary to inhibit 50% of the signal in the wells treated with drugs.

Biological Results

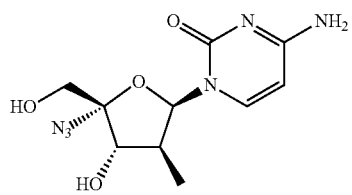 [SMILES: C[C@@H]1[C@H](n2ccc(N)nc2=O)O[C@@](CO)(N=[N+]=[N-])[C@H]1O]

Antiviral Activity

| | |
|---|---|
| Screen HIV P4 Cells % Inhibition at 50 µM | 100.11 |
| HIV Inhibition P4 Cells $EC_{50}$ (µM) | 0.18 |
| Screen HCV Clone A Cells $-\log_{10}$ at 50 µM (HCV:Rbz) | {−1.4:−0.59} |
| HCV Inhibition Clone A cells $EC_{90}$ (µM) | 7.85 |
| HCV Inhibition S282T Cells $EC_{90}$ (µM) | 73.08 |
| HBV Inhibition $EC_{90}$ (µM) | 1.62 |

Cytotoxicity ($CC_{50}$ µM)

| | |
|---|---|
| P4 Cells | >100 |
| CEM | 400 |
| BxPC3 | 400 |
| HepG2 | 300 |
| PBMC | >100 |
| Huh 7 | >100 |

The present application claims priority to U.S. provisional patent application 60/989,296, filed Nov. 20, 2007, the contents of which are incorporated by reference in its entirety.

We claim:

1. A compound selected from

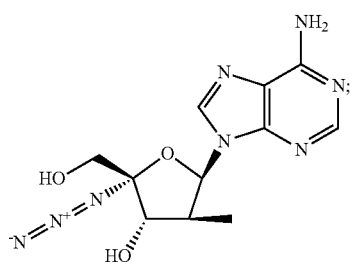

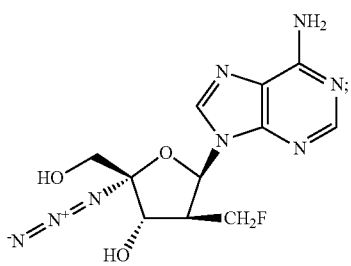

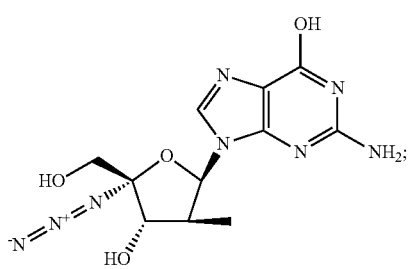

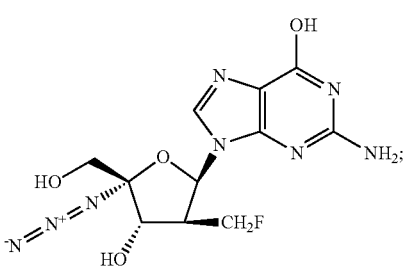

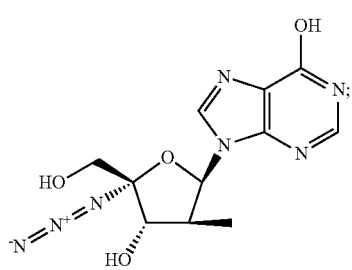

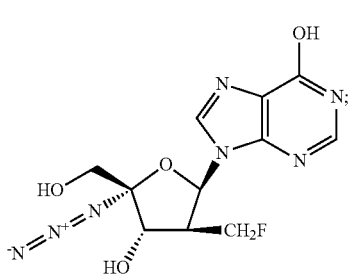

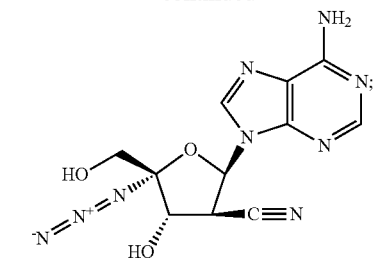
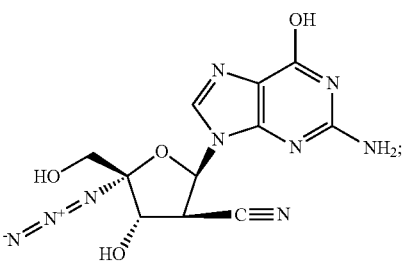
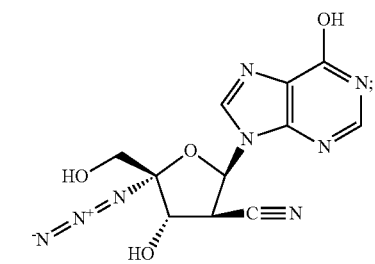
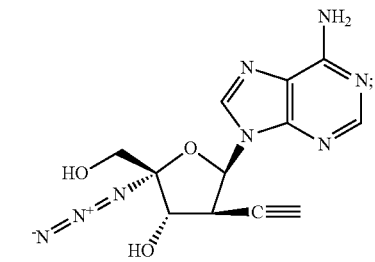
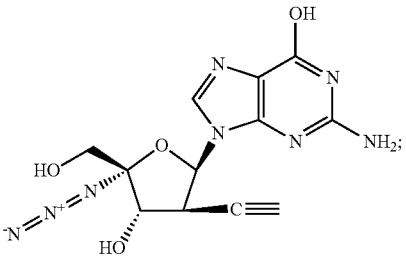
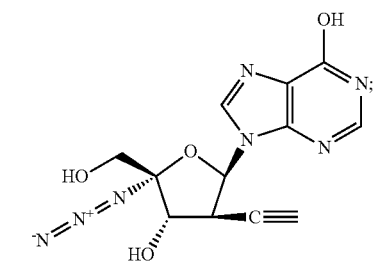
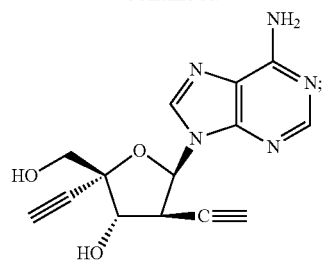
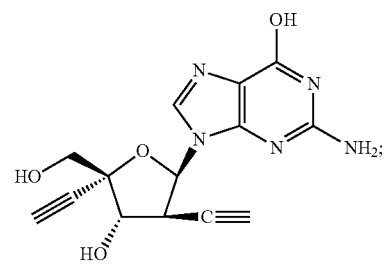
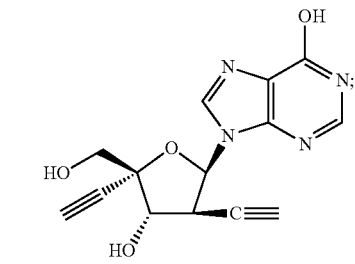
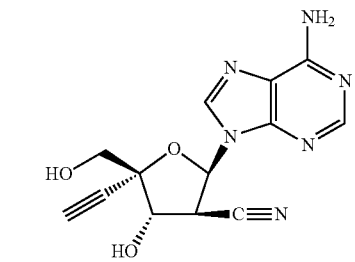
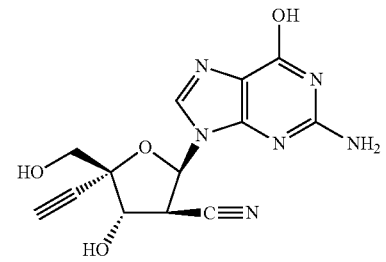
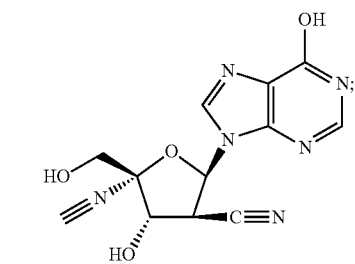

-continued
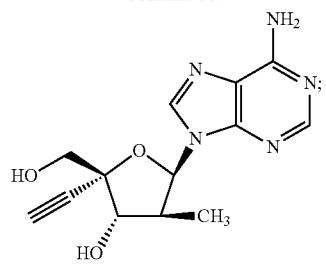
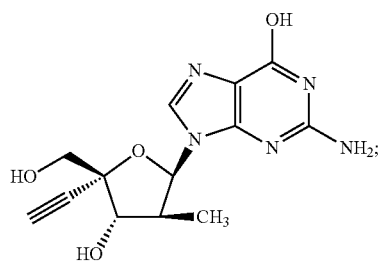
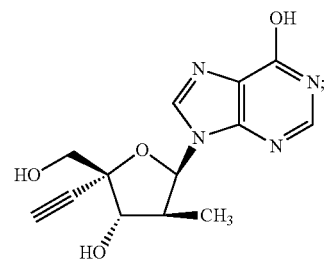
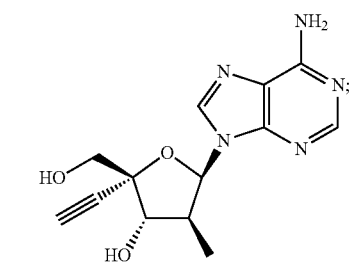
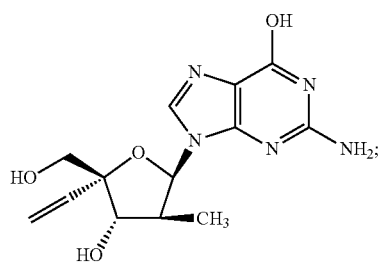
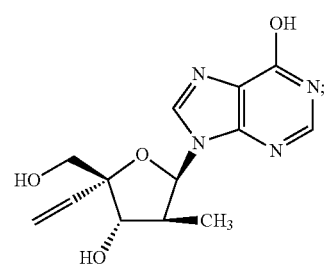
-continued
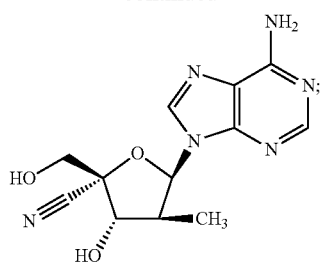
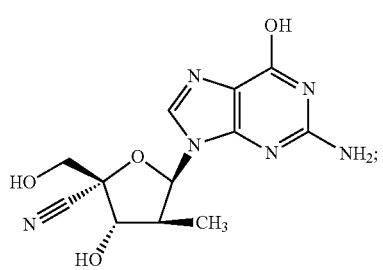
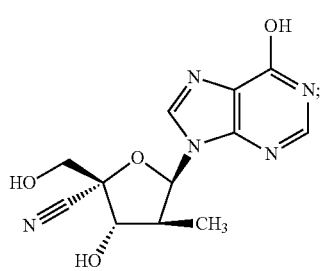
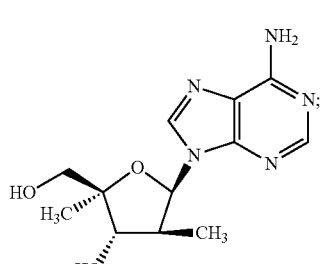
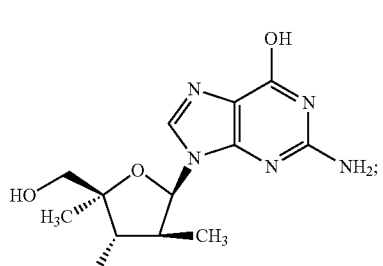
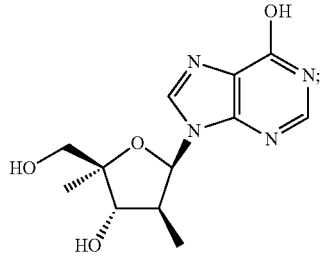

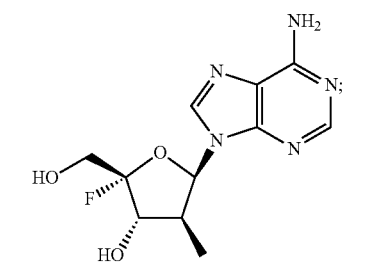
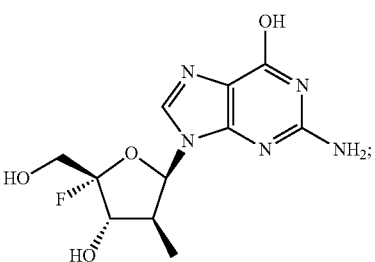
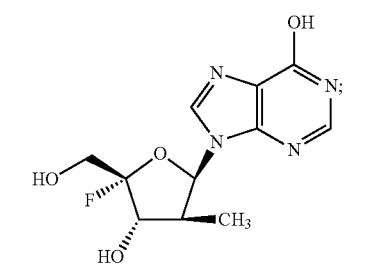
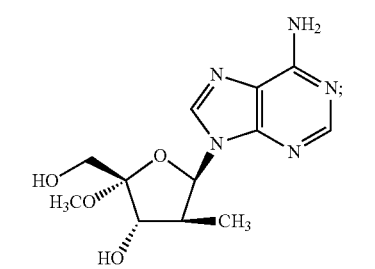
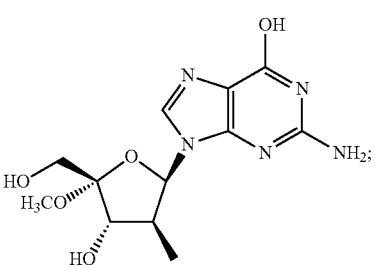
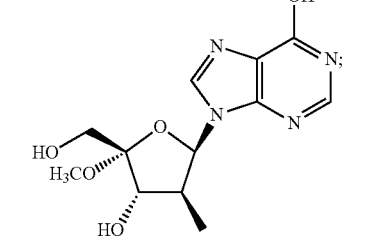
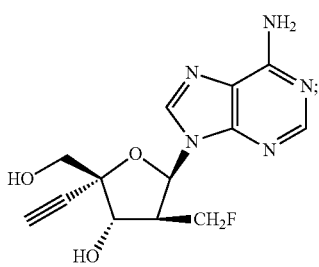
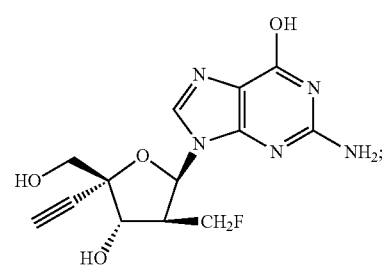
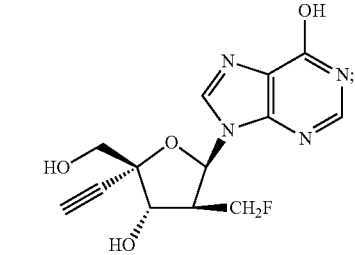
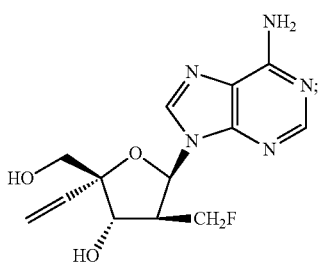
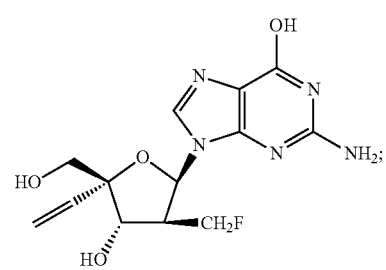
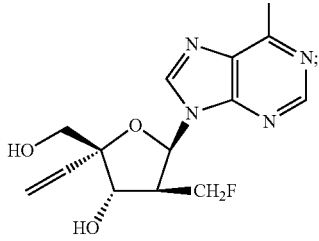

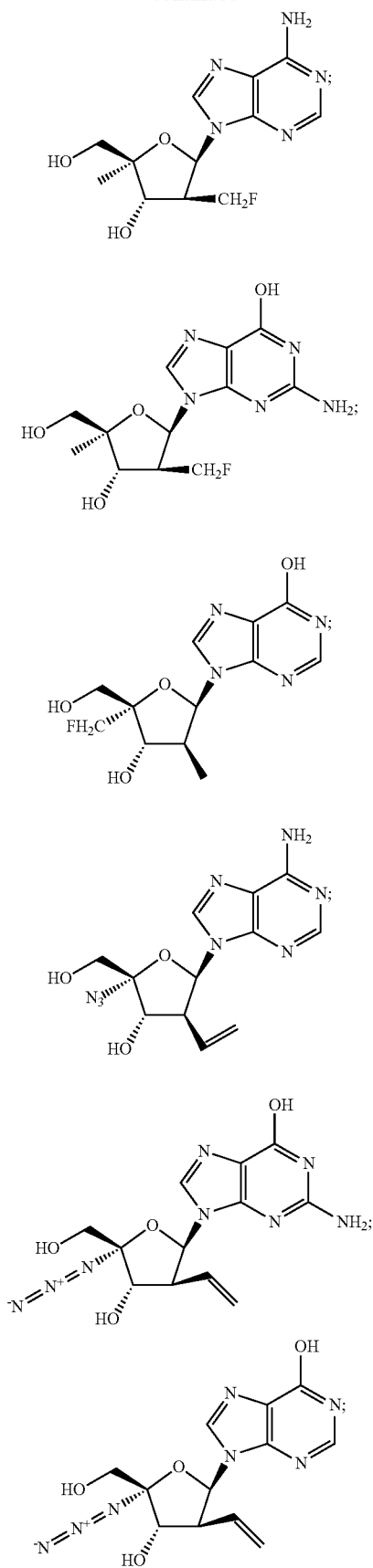
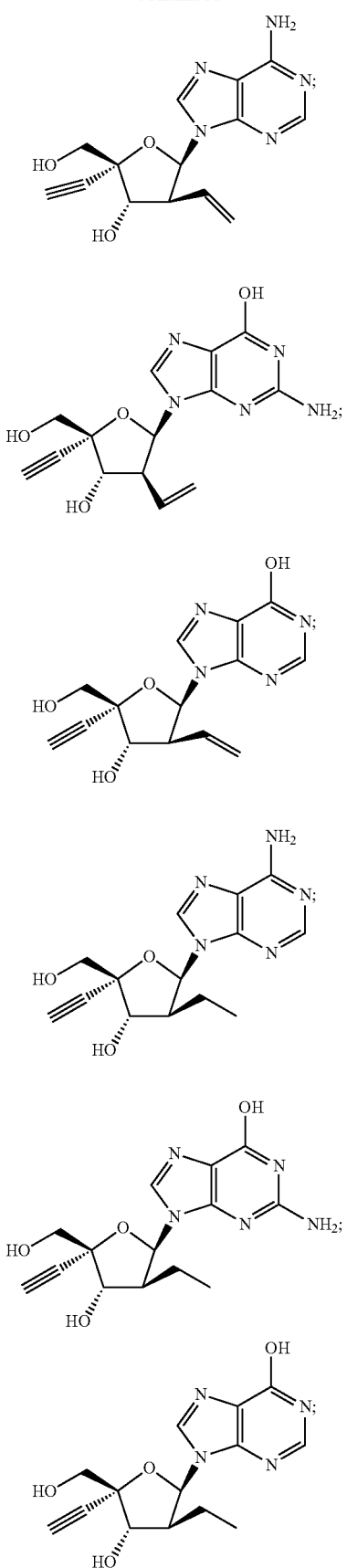

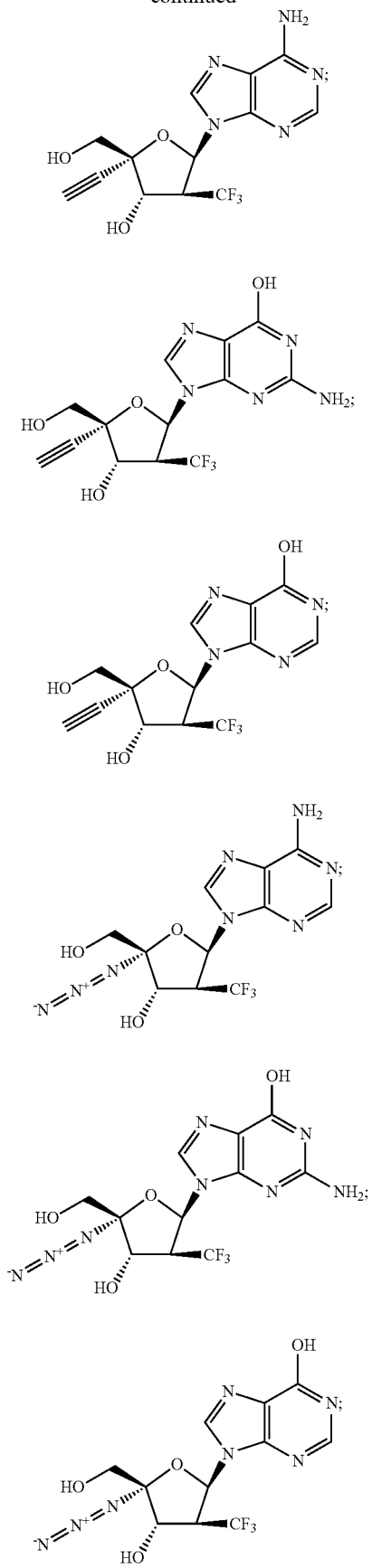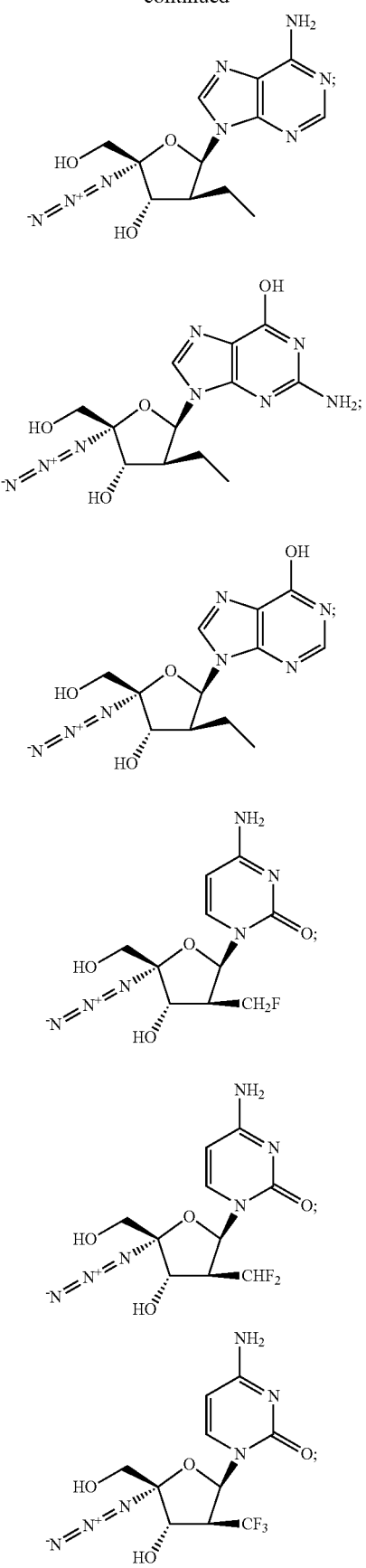

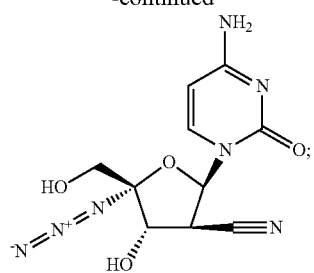
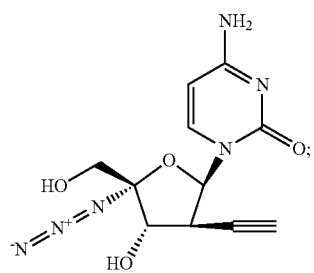
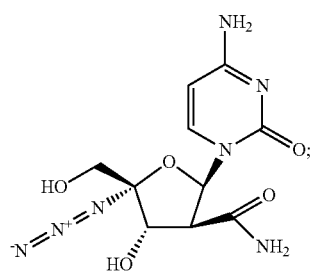
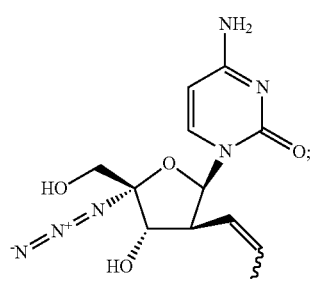
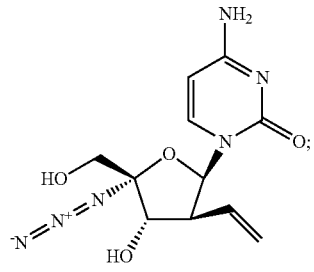
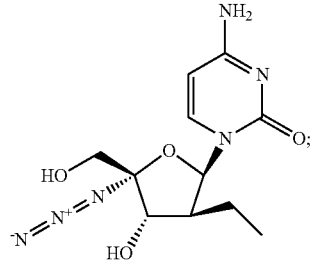
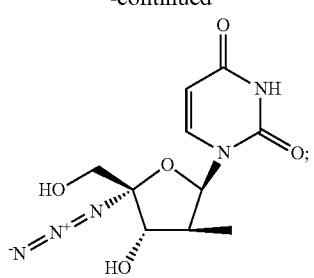
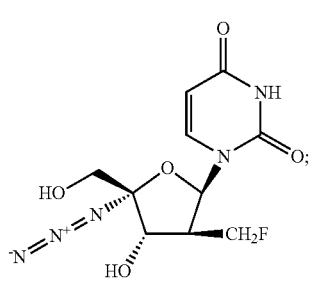
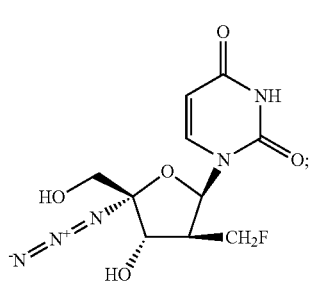
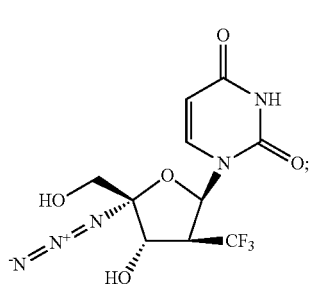
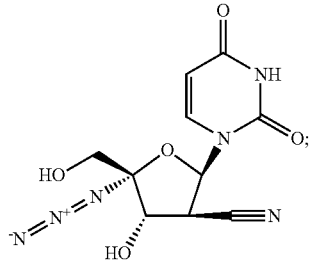
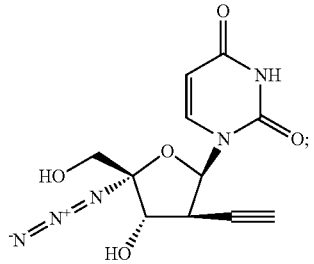

147
-continued
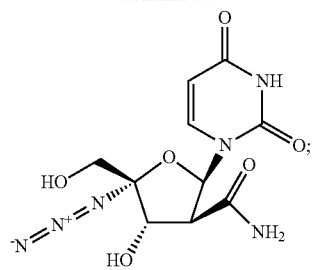
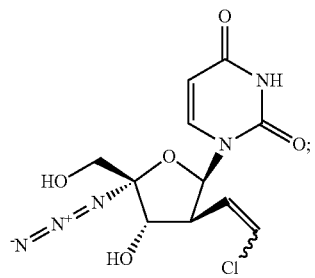
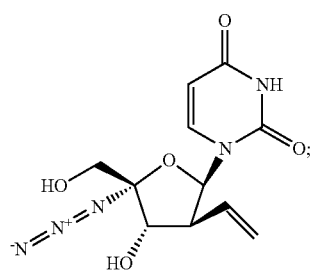
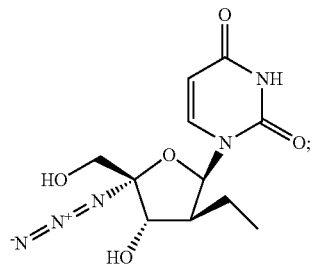
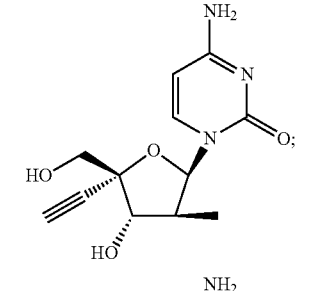
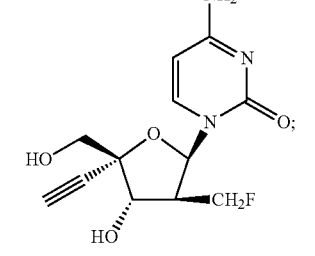
148
-continued
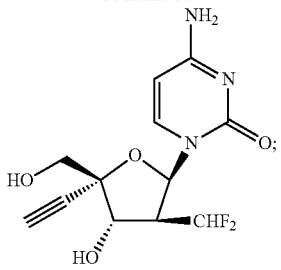
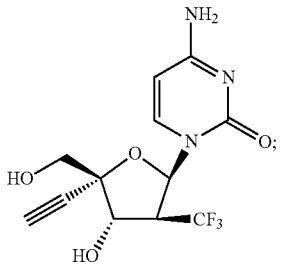
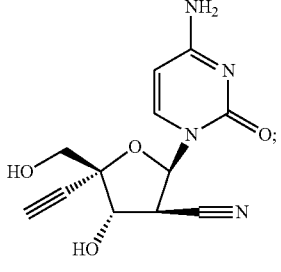
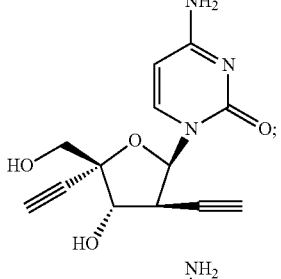
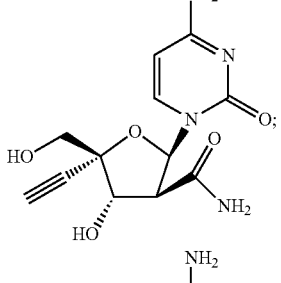
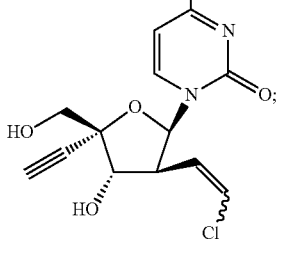

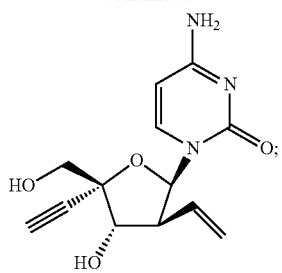
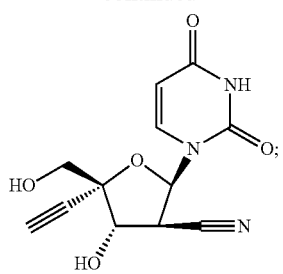
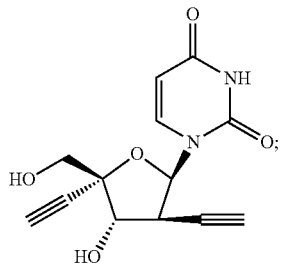
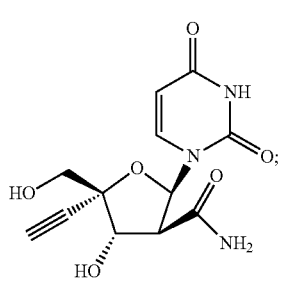
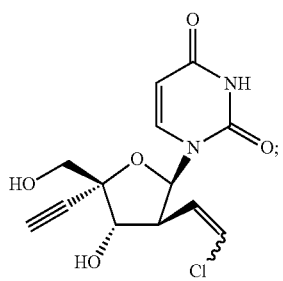
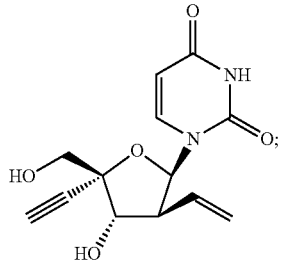
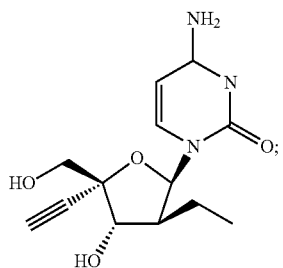

-continued
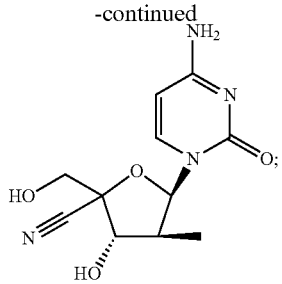
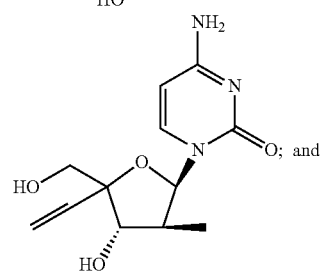
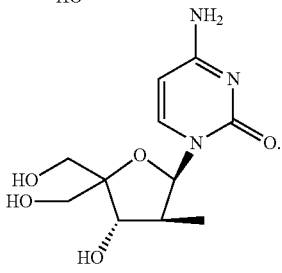
* * * * *